United States Patent
Shafer

(10) Patent No.: US 11,667,971 B2
(45) Date of Patent: Jun. 6, 2023

(54) PROBE:ANTIPROBE COMPOSITIONS FOR HIGH SPECIFICITY DNA OR RNA DETECTION

(71) Applicant: David A. Shafer, Atlanta, GA (US)

(72) Inventor: David A. Shafer, Atlanta, GA (US)

(*) Notice: Subject to any disclaimer, the term of this patent is extended or adjusted under 35 U.S.C. 154(b) by 0 days.

(21) Appl. No.: 14/216,413

(22) Filed: Mar. 17, 2014

(65) Prior Publication Data

US 2014/0287410 A1   Sep. 25, 2014

Related U.S. Application Data

(63) Continuation-in-part of application No. PCT/US2012/055620, filed on Sep. 14, 2012.

(60) Provisional application No. 61/534,925, filed on Sep. 15, 2011.

(51) Int. Cl.
*C07H 21/02* (2006.01)
*C12Q 1/6876* (2018.01)
*C12Q 1/6832* (2018.01)

(52) U.S. Cl.
CPC ......... *C12Q 1/6876* (2013.01); *C12Q 1/6832* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| 5,780,233 A * | 7/1998 | Guo ............ C12Q 1/6827 435/6.1 |
| 5,925,517 A | 7/1999 | Tyagi et al. |
| 2002/0001844 A1* | 1/2002 | Frutos ............ C07H 21/00 436/6 |
| 2009/0209434 A1 | 8/2009 | Shafer |
| 2011/0129824 A1 | 6/2011 | Dagland et al. |

FOREIGN PATENT DOCUMENTS

WO    2010130877 A2    11/2010

OTHER PUBLICATIONS

Taqman from Wikipedia, the free encyclopedia. Printed on Jun. 7, 2018.*

(Continued)

*Primary Examiner* — Frank W Lu
(74) *Attorney, Agent, or Firm* — Benjamin Aaron Adler

(57) ABSTRACT

Probe systems and methods are provided for detecting nucleic acid targets using labeled polynucleotide probes and antiprobes that interact together and with complementary targets. These interactions result in signaling changes that indicate target frequency and provide error-checking functions that facilitate single base discrimination. These probe:antiprobe compositions enable real-time PCR detection, end-point detection and microarray detection of microbial species, drug resistant mutants, and cancer related variants. The probe:antiprobe may be an internal probe between two primers or may be a primer-probe. The probe also may be modified by introducing a base mismatch to increase thermodynamic discrimination of a correct versus incorrect target differing by a single base. Probe systems also are provided for use in methods of increasing target amplification and detecting specific single base variants.

16 Claims, 20 Drawing Sheets

Specification includes a Sequence Listing.

(56) References Cited

OTHER PUBLICATIONS

Förster resonance energy transfer from Wikipedia, the free encyclopedia. Printed on Apr. 6, 2020.*
Dulkeith et al., Gold Nanoparticles Quench Fluorescence by Phase Induced Radiative Rate Suppression . Nano Lett., 5, 585-589, 2005.*
Hwang, Single-Labeled Oligonucleotides Showing Fluorescence Changes upon Hybridization with Target Nucleic Acids. Molecules, 23(1), 124, 2018.*
Li Qingge et al., A new class of homogeneous nucleic acid probes based on specific displacement hybridization, Nucleic Acids Research, Oxford University Press, vol. 30, No. 2, Jan. 15, 2002, p. E5, Fig. 1.
Jun Watanabe et al., Use of a competitive probe in assay design for genotyping of the UGT1A1*28 microsatellite polymorphism by the smart amplification process, Biotechniques, vol. 43, No. 4, Oct. 1, 2007, pp. 479-484, Fig. 5.

* cited by examiner

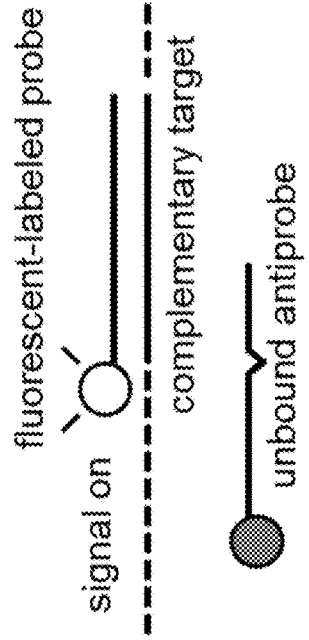
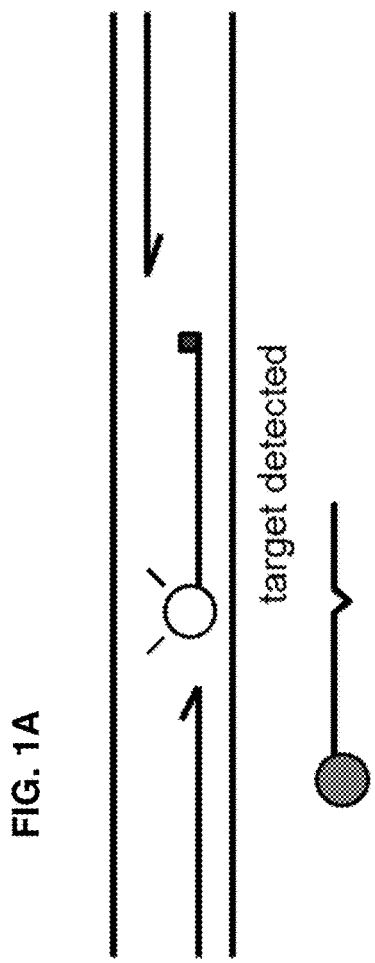
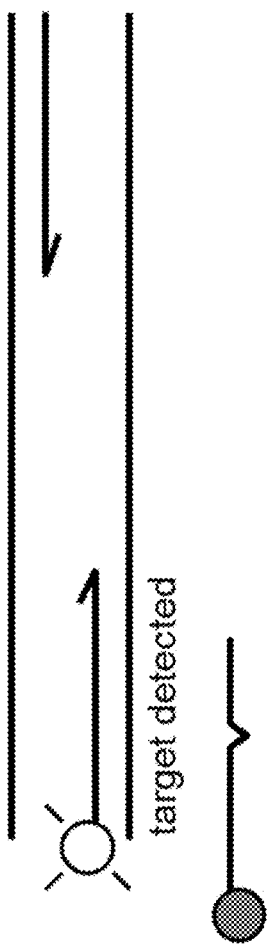
FIG. 1A
FIG. 1B
FIG. 1C

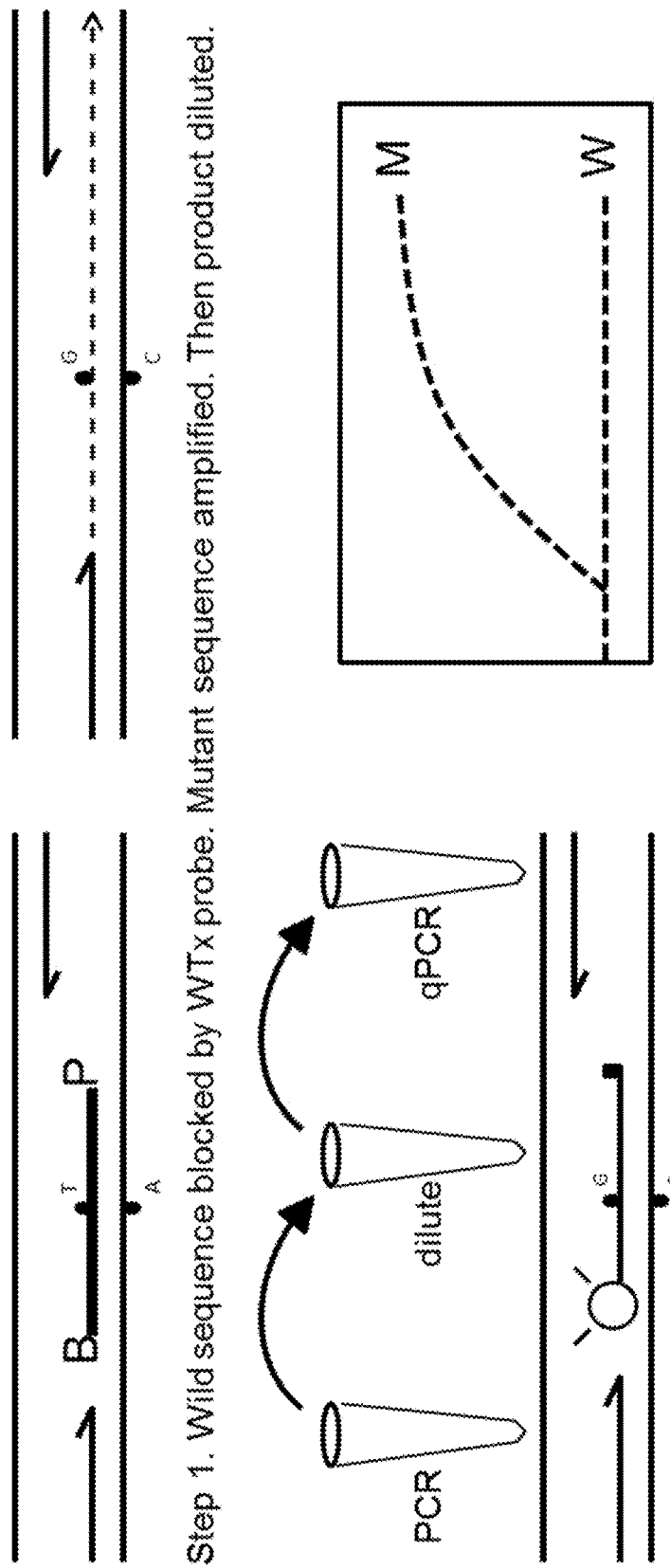
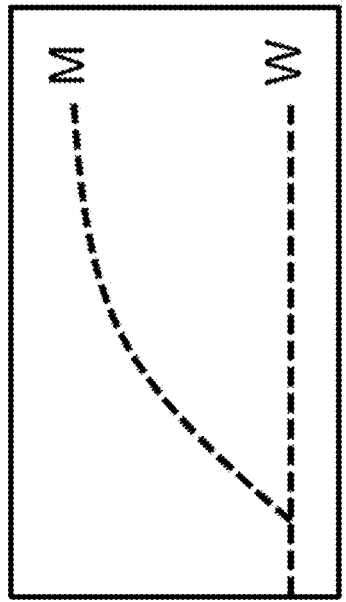
FIG. 3A
FIG. 3B

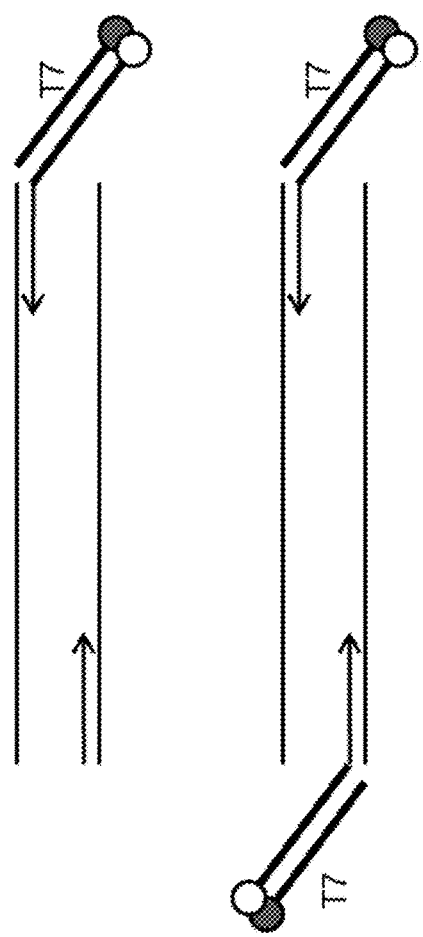
FIG. 4A
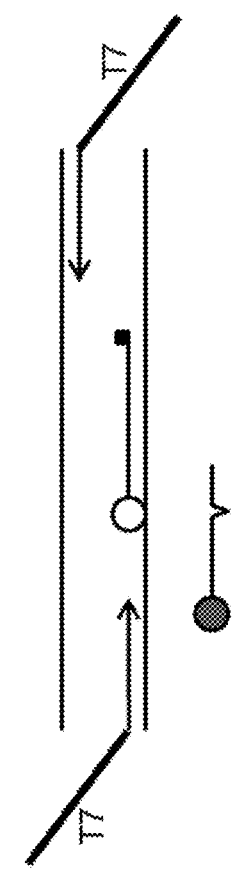
FIG. 4B
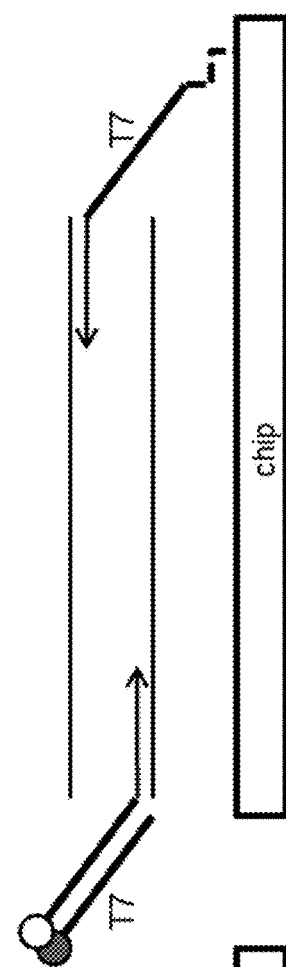
FIG. 4C
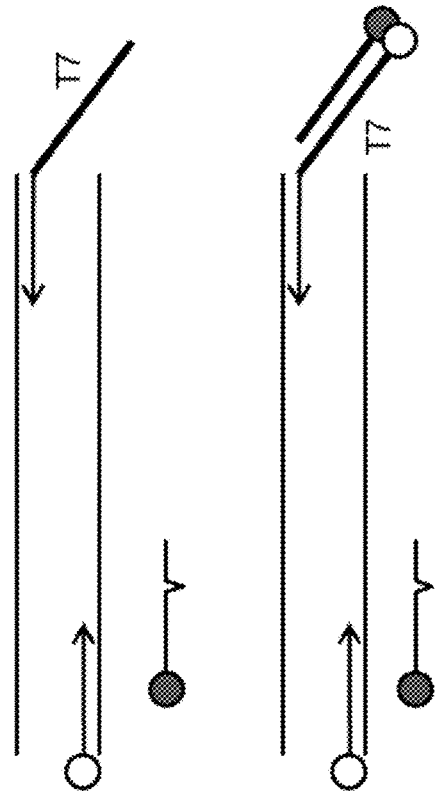
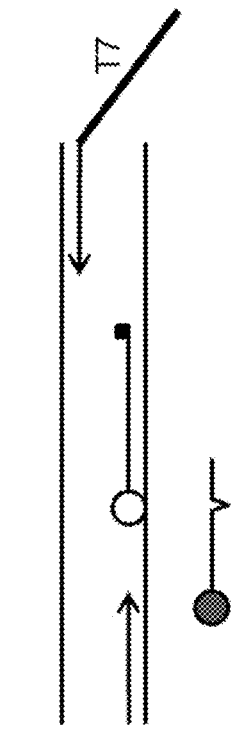

(SEQ ID NO.: 1)

(SEQ ID NO.: 1)
(SEQ ID NO.: 2)

(SEQ ID NO.: 1)
(SEQ ID NO.: 59)

VKORC1 SNP site
Probe: WildTarget duplex
Maximum Tm & ΔG

Probe:Antiprobe duplex
Tm & ΔG reduced
Tm: -6.2 °C
ΔG: -2.4 kcal/mol

Probe:Variant Target duplex
Tm & ΔG reduced further
Tm: -5.7 °C
ΔG: -2.1 kcal/mol 5'-Label-CGCACCCGGCCAATG-Phos-3'
3'-Quencher- GCGTGGGCCG TTAC-5'
                       \C/

C\
5'-label- CGCACC  GGCCAATG-Phos-3'
ACTCGGTGGGCCGTGGACCGGTTACCAACAA

5'-TGAAAACACCGCAGCATGTCAAGATCACAGATTTTGGGCGGGCCAAAACTGCTGGGTGC  SEQ ID NO.: 60   MUTANT
3'-ACTTTTGTCCGCTCCGTACAGTTCTAGTGTCTAAAACCCGCCCGGTTTTGACGACCCACG  SEQ ID NO.: 61

GGAAGAGAAAGAATACCATGCAGAA-3' SEQ ID NO.: 11
CCTTCTCTTTCTTATGGTACGTCTT-5' SEQ ID NO.: 12

Reverse primer SEQ ID NO.: 12

EGFR Forward primer SEQ ID NO.: 11

5'-TGAAAACACCGCAGCATGTCAAGATCACAGATTTTGGGCTGGCCAAAACTGCTGGGTGC  SEQ ID NO.: 62   WILD
3'-ACTTTTGTCCGCTCCGTACAGTTCTAGTGTCTAAAACCCGACCGGTTTTGACGACCCACG  SEQ ID NO.: 63

GGAAGAGAAAGAATACCATGCAGAA-3' SEQ ID NO.: 11
CCTTCTCTTTCTTATGGTACGTCTT-5' SEQ ID NO.: 12

Reverse primer SEQ ID NO.: 12

FIG. 7A

SEQUENCE LISTING

<160> NUMBER OF SEQ ID NOS: 98

<210> SEQ ID NO 1
<211> LENGTH: 15
<212> TYPE: DNA
<213> ORGANISM: Artificial Sequence
<220> FEATURE:
<223> OTHER INFORMATION: VK-1639G-Probe
<220> FEATURE:
<221> NAME/KEY: misc_feature
<222> LOCATION: (1)..(1)
<223> OTHER INFORMATION: 5'-FAM label

<400> SEQUENCE: 1
cgcacccggc caatg                                                  15

<210> SEQ ID NO 2
<211> LENGTH: 15

-continued

```
<212> TYPE: DNA
<213> ORGANISM: Artificial Sequence
<220> FEATURE:
<223> OTHER INFORMATION: VK-1639G-Antiprobe
<220> FEATURE:
<221> NAME/KEY: misc_feature
<222> LOCATION: (15)..(15)
<223> OTHER INFORMATION: 3'-BHQ1 label attached

<400> SEQUENCE: 2
cattcgccgg gtgcg                                                    15

<210> SEQ ID NO 3
<211> LENGTH: 14
<212> TYPE: DNA
<213> ORGANISM: Artificial Sequence
<220> FEATURE:
<223> OTHER INFORMATION: VK-1639A-Probe
<220> FEATURE:
<221> NAME/KEY: misc_feature
<222> LOCATION: (1)..(1)
<223> OTHER INFORMATION: 5'-FAM label attached

<400> SEQUENCE: 3
attggccagg tgcg                                                     14

<210> SEQ ID NO 4
<211> LENGTH: 14
<212> TYPE: DNA
<213> ORGANISM: Artificial Sequence
<220> FEATURE:
<223> OTHER INFORMATION: VK-1639A-Antiprobe
<220> FEATURE:
<221> NAME/KEY: misc_feature
<222> LOCATION: (14)..(14)
<223> OTHER INFORMATION: 3'-BHQ1 label attached

<400> SEQUENCE: 4
cgcacctggc ctat                                                     14

<210> SEQ ID NO 5
<211> LENGTH: 20
<212> TYPE: DNA
<213> ORGANISM: Artificial Sequence
<220> FEATURE:
<223> OTHER INFORMATION: VK-Forward primer

<400> SEQUENCE: 5
cctctgggaa gtcaagcaag                                               20

<210> SEQ ID NO 6
<211> LENGTH: 23
<212> TYPE: DNA
<213> ORGANISM: Artificial Sequence
<220> FEATURE:
<223> OTHER INFORMATION: VK-Reverse primer

<400> SEQUENCE: 6
aaatgctagg attataggcg tga                                           23

<210> SEQ ID NO 7
<211> LENGTH: 23
<212> TYPE: DNA
<213> ORGANISM: Artificial Sequence
<220> FEATURE:
<223> OTHER INFORMATION: EGFR variant 858R probe
<220> FEATURE:
<221> NAME/KEY: misc_feature
<222> LOCATION: (1)..(1)
```

```
<223> OTHER INFORMATION: 5'-FAM label attached

<400> SEQUENCE: 7
cagattttgg ccgggccaaa ctg                                              23

<210> SEQ ID NO 8
<211> LENGTH: 23
<212> TYPE: DNA
<213> ORGANISM: Artificial Sequence
<220> FEATURE:
<223> OTHER INFORMATION: EGFR variant 858R antiprobe
<220> FEATURE:
<221> NAME/KEY: misc_feature
<222> LOCATION: (23)..(23)
<223> OTHER INFORMATION: 3'-BHQ1 label attached

<400> SEQUENCE: 8
cagtttggcc cgcccaatat ctg                                              23

<210> SEQ ID NO 9
<211> LENGTH: 23
<212> TYPE: DNA
<213> ORGANISM: Artificial Sequence
<220> FEATURE:
<223> OTHER INFORMATION: EGFR wild 858L probe
<220> FEATURE:
<221> NAME/KEY: misc_feature
<222> LOCATION: (1)..(1)
<223> OTHER INFORMATION: 5'-CalRed610 label attached

<400> SEQUENCE: 9
cagattttgg gctgaccaaa ctg                                              23

<210> SEQ ID NO 10
<211> LENGTH: 23
<212> TYPE: DNA
<213> ORGANISM: Artificial Sequence
<220> FEATURE:
<223> OTHER INFORMATION: EGFR wild 858L antiprobe
<220> FEATURE:
<221> NAME/KEY: misc_feature
<222> LOCATION: (23)..(23)
<223> OTHER INFORMATION: 3'-BHQ2 label attached

<400> SEQUENCE: 10
cagtttggcc agcccataat ctg                                              23

<210> SEQ ID NO 11
<211> LENGTH: 19
<212> TYPE: DNA
<213> ORGANISM: Artificial Sequence
<220> FEATURE:
<223> OTHER INFORMATION: EGFR Forward PCR primer-F2

<400> SEQUENCE: 11
gaaaacaccg cagcatgtc                                                   19

<210> SEQ ID NO 12
<211> LENGTH: 23
<212> TYPE: DNA
<213> ORGANISM: Artificial Sequence
<220> FEATURE:
<223> OTHER INFORMATION: EGFR Reverse PCR primer-R2

<400> SEQUENCE: 12
ctgcatggta ttctttctct tcc                                              23
```

```
<210> SEQ ID NO 13
<211> LENGTH: 19
<212> TYPE: DNA
<213> ORGANISM: Artificial Sequence
<220> FEATURE:
<223> OTHER INFORMATION: Mutant O157 uidA probe
<220> FEATURE:
<221> NAME/KEY: misc_feature
<222> LOCATION: (1)..(1)
<223> OTHER INFORMATION: 5'-FAM label attached

<400> SEQUENCE: 13
caccaacgct gctcaattc                                                19

<210> SEQ ID NO 14
<211> LENGTH: 19
<212> TYPE: DNA
<213> ORGANISM: Artificial Sequence
<220> FEATURE:
<223> OTHER INFORMATION: Mutant antiprobe
<220> FEATURE:
<221> NAME/KEY: misc_feature
<222> LOCATION: (19)..(19)
<223> OTHER INFORMATION: 3'-BHQ1 label attached

<400> SEQUENCE: 14
gaattgagct gcgttggtg                                                19

<210> SEQ ID NO 15
<211> LENGTH: 21
<212> TYPE: DNA
<213> ORGANISM: Artificial Sequence
<220> FEATURE:
<223> OTHER INFORMATION: uidA-Forward PCR primer

<400> SEQUENCE: 15
cagtctggat cgcgaaaact g                                             21

<210> SEQ ID NO 16
<211> LENGTH: 22
<212> TYPE: DNA
<213> ORGANISM: Artificial Sequence
<220> FEATURE:
<223> OTHER INFORMATION: uidA-Reverse PCR primer

<400> SEQUENCE: 16
accagacgtt gcccacataa tt                                            22

<210> SEQ ID NO 17
<211> LENGTH: 22
<212> TYPE: DNA
<213> ORGANISM: Artificial Sequence
<220> FEATURE:
<223> OTHER INFORMATION: Gram positive-specific probe
<220> FEATURE:
<221> NAME/KEY: misc_feature
<222> LOCATION: (1)..(1)
<223> OTHER INFORMATION: 5'-FAM label attached

<400> SEQUENCE: 17
aaggggcttg atgatttgac gt                                            22

<210> SEQ ID NO 18
<211> LENGTH: 22
<212> TYPE: DNA
<213> ORGANISM: Artificial Sequence
<220> FEATURE:
<223> OTHER INFORMATION: Gram positive-specific antiprobe
<220> FEATURE:
```

-continued

```
<221> NAME/KEY: misc_feature
<222> LOCATION: (22)..(22)
<223> OTHER INFORMATION: 3'-BHQ1 label attached

<400> SEQUENCE: 18
acgtcaaatc ttcatgcccc tt                                              22

<210> SEQ ID NO 19
<211> LENGTH: 19
<212> TYPE: DNA
<213> ORGANISM: Artificial Sequence
<220> FEATURE:
<223> OTHER INFORMATION: Gram negative-specific probe
<220> FEATURE:
<221> NAME/KEY: misc_feature
<222> LOCATION: (1)..(1)
<223> OTHER INFORMATION: 5'-CalRed610 label attached

<400> SEQUENCE: 19
aagggccatg atgacttga                                                  19

<210> SEQ ID NO 20
<211> LENGTH: 19
<212> TYPE: DNA
<213> ORGANISM: Artificial Sequence
<220> FEATURE:
<223> OTHER INFORMATION: Gram negative-specific antiprobe
<220> FEATURE:
<221> NAME/KEY: misc_feature
<222> LOCATION: (19)..(19)
<223> OTHER INFORMATION: 3'-BHQ2 label attached

<400> SEQUENCE: 20
tcaagtcttc atggcccctt                                                 19

<210> SEQ ID NO 21
<211> LENGTH: 18
<212> TYPE: DNA
<213> ORGANISM: Artificial Sequence
<220> FEATURE:
<223> OTHER INFORMATION: Forward PCR primer

<400> SEQUENCE: 21
tcccgcaacg agcgcaac                                                   18

<210> SEQ ID NO 22
<211> LENGTH: 21
<212> TYPE: DNA
<213> ORGANISM: Artificial Sequence
<220> FEATURE:
<223> OTHER INFORMATION: Reverse PCR primer

<400> SEQUENCE: 22
cagccattgt agcacgtgtg t                                               21

<210> SEQ ID NO 23
<211> LENGTH: 21
<212> TYPE: DNA
<213> ORGANISM: Artificial Sequence
<220> FEATURE:
<223> OTHER INFORMATION: ZIPR H3 Probe
<220> FEATURE:
<221> NAME/KEY: misc_feature
<222> LOCATION: (1)..(1)
<223> OTHER INFORMATION: 5'-FAM label attached

<400> SEQUENCE: 23
ctggttcaga gttcctcaac a                                               21
```

```
<210> SEQ ID NO 24
<211> LENGTH: 21
<212> TYPE: DNA
<213> ORGANISM: Artificial Sequence
<220> FEATURE:
<223> OTHER INFORMATION: ZIPR H3 antiprobe
<220> FEATURE:
<221> NAME/KEY: misc_feature
<222> LOCATION: (21)..(21)
<223> OTHER INFORMATION: 3'-BHQ1 label attached

<400> SEQUENCE: 24
tgttgatgaa ctctgaacca g                                        21

<210> SEQ ID NO 25
<211> LENGTH: 21
<212> TYPE: DNA
<213> ORGANISM: Artificial Sequence
<220> FEATURE:
<223> OTHER INFORMATION: H3 primer

<400> SEQUENCE: 25
ccatcaagga tctgatgagg a                                        21

<210> SEQ ID NO 26
<211> LENGTH: 23
<212> TYPE: DNA
<213> ORGANISM: Artificial Sequence
<220> FEATURE:
<223> OTHER INFORMATION: FLIP DDS probe
<220> FEATURE:
<221> NAME/KEY: misc_feature
<222> LOCATION: (23)..(23)
<223> OTHER INFORMATION: 3'-FAM label attached

<400> SEQUENCE: 26
taggaccacg ggatgcatgt ctt                                      23

<210> SEQ ID NO 27
<211> LENGTH: 39
<212> TYPE: DNA
<213> ORGANISM: Artificial sequence
<220> FEATURE:
<223> OTHER INFORMATION: FLIP antiprobe/forward primer
<220> FEATURE:
<221> NAME/KEY: misc_feature
<222> LOCATION: (1)..(1)
<223> OTHER INFORMATION: 5'-dT-BHQ1 label attached
<220> FEATURE:
<221> NAME/KEY: misc_feature
<222> LOCATION: (19)..(20)
<223> OTHER INFORMATION: spacer 9 which is a 9 atom triethylene glycol
      chain is inserted between nucleotides 19 and 20

<400> SEQUENCE: 27
aagacatgca tcccgtggtg ggataagcct gggaaactg                     39

<210> SEQ ID NO 28
<211> LENGTH: 20
<212> TYPE: DNA
<213> ORGANISM: Artificial Sequence
<220> FEATURE:
<223> OTHER INFORMATION: Taqman probe
<220> FEATURE:
<221> NAME/KEY: misc_feature
<222> LOCATION: (1)..(1)
<223> OTHER INFORMATION: 5'-FAM label attached
<220> FEATURE:
<221> NAME/KEY: misc_feature
```

```
<222> LOCATION: (20)..(20)
<223> OTHER INFORMATION: 3'-BHQ1 label attached

<400> SEQUENCE: 28
catgtcttgt ggtggaaagc                                              20

<210> SEQ ID NO 29
<211> LENGTH: 20
<212> TYPE: DNA
<213> ORGANISM: Artificial Sequence
<220> FEATURE:
<223> OTHER INFORMATION: Forward PcR primer

<400> SEQUENCE: 29
gggataagcc tgggaaactg                                              20

<210> SEQ ID NO 30
<211> LENGTH: 20
<212> TYPE: DNA
<213> ORGANISM: Artificial Sequence
<220> FEATURE:
<223> OTHER INFORMATION: Reverse PCR primer

<400> SEQUENCE: 30
accccaccaa caagctgata                                              20

<210> SEQ ID NO 31
<211> LENGTH: 38
<212> TYPE: DNA
<213> ORGANISM: Artificial Sequence
<220> FEATURE:
<223> OTHER INFORMATION: GF primer/probe
<220> FEATURE:
<221> NAME/KEY: misc_feature
<222> LOCATION: (1)..(1)
<223> OTHER INFORMATION: 5'-FAM label attached

<400> SEQUENCE: 31
cccctccasa craggagggg gccgctgtcg gggttgac                           38

<210> SEQ ID NO 32
<211> LENGTH: 19
<212> TYPE: DNA
<213> ORGANISM: Artificial Sequence
<220> FEATURE:
<223> OTHER INFORMATION: Reverse primer

<400> SEQUENCE: 32
cacgctcatg tgacagacc                                               19

<210> SEQ ID NO 33
<211> LENGTH: 19
<212> TYPE: DNA
<213> ORGANISM: Artificial Sequence
<220> FEATURE:
<223> OTHER INFORMATION: iDDS probe
<220> FEATURE:
<221> NAME/KEY: misc_feature
<222> LOCATION: (1)..(1)
<223> OTHER INFORMATION: 5'-CalFluorRed610 label attached

<400> SEQUENCE: 33
cggggttgac ccactagcg                                               19

<210> SEQ ID NO 34
<211> LENGTH: 19
<212> TYPE: DNA
```

```
<213> ORGANISM: Artificial Sequence
<220> FEATURE:
<223> OTHER INFORMATION: Antiprobe
<220> FEATURE:
<221> NAME/KEY: misc_feature
<222> LOCATION: (19)..(19)
<223> OTHER INFORMATION: 3'-BHQ2 label attached

<400> SEQUENCE: 34
cgcttgtggg tctaccccg                                                    19

<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35
gctcgtggac ataccgattt                                                   20

<210> SEQ ID NO 36
<211> LENGTH: 21
<212> TYPE: DNA
<213> ORGANISM: Artificial Sequence
<220> FEATURE:
<223> OTHER INFORMATION: inhA iDDS probe
<220> FEATURE:
<221> NAME/KEY: misc_feature
<222> LOCATION: (1)..(1)
<223> OTHER INFORMATION: 5'-CalRed610 label attached

<400> SEQUENCE: 36
ccgacaacct atcgtctcgc c                                                 21

<210> SEQ ID NO 37
<211> LENGTH: 19
<212> TYPE: DNA
<213> ORGANISM: Artificial Sequence
<220> FEATURE:
<223> OTHER INFORMATION: inhA antiprobe
<220> FEATURE:
<221> NAME/KEY: misc_feature
<222> LOCATION: (19)..(19)
<223> OTHER INFORMATION: 3'-BHQ2 label attached

<400> SEQUENCE: 37
cgagacgata ggttgtcgg                                                    19

<210> SEQ ID NO 38
<211> LENGTH: 38
<212> TYPE: DNA
<213> ORGANISM: Artificial Sequence
<220> FEATURE:
<223> OTHER INFORMATION: InhA G-Force primer-probe
<220> FEATURE:
<221> NAME/KEY: misc_feature
<222> LOCATION: (8)..(9)
<223> OTHER INFORMATION: spacer 18 which is an 18 atom hexaethylene
     glycol chain is inserted between nucleotides 8 and 9
<220> FEATURE:
<221> NAME/KEY: misc_feature
<222> LOCATION: (9)..(9)
<223> OTHER INFORMATION: n is a, c, g, or t

<400> SEQUENCE: 38
cccctccana ggaggggtc cggtaaccag gactgaac                                38

<210> SEQ ID NO 39
```

```
<211> LENGTH: 20
<212> TYPE: DNA
<213> ORGANISM: Artificial Sequence
<220> FEATURE:
<223> OTHER INFORMATION: EGFR Outer forward primer-F1

<400> SEQUENCE: 39
agccaggaac gtactggtga                                          20

<210> SEQ ID NO 40
<211> LENGTH: 20
<212> TYPE: DNA
<213> ORGANISM: Artificial Sequence
<220> FEATURE:
<223> OTHER INFORMATION: EGFR Outer reverse primer-R1

<400> SEQUENCE: 40
tgcctccttc tgcatggtat                                          20

<210> SEQ ID NO 41
<211> LENGTH: 27
<212> TYPE: DNA
<213> ORGANISM: Artificial Sequence
<220> FEATURE:
<223> OTHER INFORMATION: Terminator blocking probe
<220> FEATURE:
<221> NAME/KEY: misc_feature
<222> LOCATION: (1)..(1)
<223> OTHER INFORMATION: 5'-biotin attached

<400> SEQUENCE: 41
ctttcccacc aacgcagatc aattcca                                  27

<210> SEQ ID NO 42
<211> LENGTH: 20
<212> TYPE: DNA
<213> ORGANISM: Artificial Sequence
<220> FEATURE:
<223> OTHER INFORMATION: GAPDH-Cy3F1
<220> FEATURE:
<221> NAME/KEY: misc_feature
<222> LOCATION: (1)..(1)
<223> OTHER INFORMATION: 5'-Cy3 label attached

<400> SEQUENCE: 42
gagtcaacgg atttggtcgt                                          20

<210> SEQ ID NO 43
<211> LENGTH: 12
<212> TYPE: DNA
<213> ORGANISM: Artificial Sequence
<220> FEATURE:
<223> OTHER INFORMATION: GAPDH-BHQ2
<220> FEATURE:
<221> NAME/KEY: misc_feature
<222> LOCATION: (12)..(12)
<223> OTHER INFORMATION: 3'-BHQ2 label attached

<400> SEQUENCE: 43
atccgttgac tc                                                  12

<210> SEQ ID NO 44
<211> LENGTH: 51
<212> TYPE: DNA
<213> ORGANISM: Artificial Sequence
<220> FEATURE:
<223> OTHER INFORMATION: GAPDH-T7R1

<400> SEQUENCE: 44
```
aattctaata cgactcacta tagggagaag ggacaagctt cccgttctca g                51

<210> SEQ ID NO 45
<211> LENGTH: 51
<212> TYPE: DNA
<213> ORGANISM: Artificial Sequence
<220> FEATURE:
<223> OTHER INFORMATION: GAPDH-T7F1

<400> SEQUENCE: 45
aattctaata cgactcacta tagggagaag ggagtcaacg gatttggtcg t                51

<210> SEQ ID NO 46
<211> LENGTH: 51
<212> TYPE: DNA
<213> ORGANISM: Artificial Sequence
<220> FEATURE:
<223> OTHER INFORMATION: GAPDH-R1

<400> SEQUENCE: 46
aattctaata cgactcacta tagggagaag ggacaagctt cccgttctca g                51

<210> SEQ ID NO 47
<211> LENGTH: 24
<212> TYPE: DNA
<213> ORGANISM: Artificial Sequence
<220> FEATURE:
<223> OTHER INFORMATION: GDH iDDS probe
<220> FEATURE:
<221> NAME/KEY: misc_feature
<222> LOCATION: (1)..(1)
<223> OTHER INFORMATION: 5'-FAM label attached
<220> FEATURE:
<221> NAME/KEY: misc_feature
<222> LOCATION: (24)..(24)
<223> OTHER INFORMATION: 3'-amino attached

<400> SEQUENCE: 47
ccttcattga cctcaactac atgg                                              24

<210> SEQ ID NO 48
<211> LENGTH: 15
<212> TYPE: DNA
<213> ORGANISM: Artificial Sequence
<220> FEATURE:
<223> OTHER INFORMATION: GDH iDDS antiprobe
<220> FEATURE:
<221> NAME/KEY: misc_feature
<222> LOCATION: (15)..(15)
<223> OTHER INFORMATION: 3'-BHQ1 label attached

<400> SEQUENCE: 48
tgaggtcaat gaagg                                                        15

<210> SEQ ID NO 49
<211> LENGTH: 51
<212> TYPE: DNA
<213> ORGANISM: Artificial Sequence
<220> FEATURE:
<223> OTHER INFORMATION: GDH-R1s
<220> FEATURE:
<221> NAME/KEY: misc_feature
<222> LOCATION: (1)..(1)
<223> OTHER INFORMATION: 5'-amino spacer 18 which is an 18 atom
      hexaethylene glycol chain is attached to nucleotide 1

<400> SEQUENCE: 49
atttctaata cgactcacta tagggagaag ggacaagctt cccgttctca g                51

<210> SEQ ID NO 50
<211> LENGTH: 51
<212> TYPE: DNA
<213> ORGANISM: Artificial Sequence
<220> FEATURE:
<223> OTHER INFORMATION: Rab9-Rls
<220> FEATURE:
<221> NAME/KEY: misc_feature
<222> LOCATION: (1)..(1)
<223> OTHER INFORMATION: 5'-amino spacer 18 which is an 18 atom
      hexaethylene glycol chain is attached to nucleotide 1

<400> SEQUENCE: 50
atttctaata cgactcacta tagggagaag gaaatggtgt cctcaggctt c     51

<210> SEQ ID NO 51
<211> LENGTH: 20
<212> TYPE: DNA
<213> ORGANISM: Artificial Sequence
<220> FEATURE:
<223> OTHER INFORMATION: GDHCy3F1
<220> FEATURE:
<221> NAME/KEY: misc_feature
<222> LOCATION: (1)..(1)
<223> OTHER INFORMATION: 5'-Cy3 attached

<400> SEQUENCE: 51
gagtcaacgg atttggtcgt     20

<210> SEQ ID NO 52
<211> LENGTH: 47
<212> TYPE: DNA
<213> ORGANISM: Artificial Sequence
<220> FEATURE:
<223> OTHER INFORMATION: Rab9-FAM-T7F1
<220> FEATURE:
<221> NAME/KEY: misc_feature
<222> LOCATION: (1)..(1)
<223> OTHER INFORMATION: 5'-FAM label attached

<400> SEQUENCE: 52
aattctaata cgactcacta tagggagaag gcaatggcag gaaaatc     47

<210> SEQ ID NO 53
<211> LENGTH: 20
<212> TYPE: DNA
<213> ORGANISM: Artificial Sequence
<220> FEATURE:
<223> OTHER INFORMATION: Non-specific Rev. Primer

<400> SEQUENCE: 53
cgtaggcttc atcgaggatt     20

<210> SEQ ID NO 54
<211> LENGTH: 22
<212> TYPE: DNA
<213> ORGANISM: Artificial Sequence
<220> FEATURE:
<223> OTHER INFORMATION: Rev. ziPR Wild Only Probe
<220> FEATURE:
<221> NAME/KEY: misc_feature
<222> LOCATION: (1)..(1)
<223> OTHER INFORMATION: 5'-Quasar670

<400> SEQUENCE: 54
tcggagatgt tgcttctctt aa     22

```
<210> SEQ ID NO 55
<211> LENGTH: 22
<212> TYPE: DNA
<213> ORGANISM: Artificial Sequence
<220> FEATURE:
<223> OTHER INFORMATION: Rev. ZIPR wild Only Antiprobe
<220> FEATURE:
<221> NAME/KEY: misc_feature
<222> LOCATION: (22)..(22)
<223> OTHER INFORMATION: 3'-BHQ2 label attached

<400> SEQUENCE: 55
ttaagagatg caacatctcc ga                                              22

<210> SEQ ID NO 56
<211> LENGTH: 20
<212> TYPE: DNA
<213> ORGANISM: Artificial Sequence
<220> FEATURE:
<223> OTHER INFORMATION: For. ZIPR Probe
<220> FEATURE:
<221> NAME/KEY: misc_feature
<222> LOCATION: (1)..(1)
<223> OTHER INFORMATION: 5'-CalRed610 label attached

<400> SEQUENCE: 56
tctggatccc agaaggtgag                                                 20

<210> SEQ ID NO 57
<211> LENGTH: 20
<212> TYPE: DNA
<213> ORGANISM: Artificial Sequence
<220> FEATURE:
<223> OTHER INFORMATION: For. ZIPR Antiprobe
<220> FEATURE:
<221> NAME/KEY: misc_feature
<222> LOCATION: (20)..(20)
<223> OTHER INFORMATION: 3'-BHQ2 label attached

<400> SEQUENCE: 57
ctcaccttct gggttccaga                                                 20

<210> SEQ ID NO 58
<211> LENGTH: 29
<212> TYPE: DNA
<213> ORGANISM: Artificial Sequence
<220> FEATURE:
<223> OTHER INFORMATION: VKORC1 wild target segment

<400> SEQUENCE: 58
actcggtggc gtgggccggt taccaacaa                                       29

<210> SEQ ID NO 59
<211> LENGTH: 29
<212> TYPE: DNA
<213> ORGANISM: Artificial Sequence
<220> FEATURE:
<223> OTHER INFORMATION: vKORC1 variant target segment

<400> SEQUENCE: 59
actcggtggc gtggaccggt taccaacaa                                       29

<210> SEQ ID NO 60
<211> LENGTH: 83
<212> TYPE: DNA
<213> ORGANISM: Artificial Sequence
<220> FEATURE:
<223> OTHER INFORMATION: EGFR bp2535-2616 mutant sense strand
```

-continued

```
<400> SEQUENCE: 60
tgaaaacacc gcagcatgtc aagatcacag attttgggcg ggccaaactg ctgggtgcgg    60
aagagaaaga ataccatgca gaa                                            83

<210> SEQ ID NO 61
<211> LENGTH: 83
<212> TYPE: DNA
<213> ORGANISM: Artificial Sequence
<220> FEATURE:
<223> OTHER INFORMATION: EGFR bp2535-2616 mutant antisense strand

<400> SEQUENCE: 61
ttctgcatgg tattctttct cttccgcacc cagcagtttg gcccgcccaa aatctgtgat    60
cttgacatgc tcgcctgttt tca                                            83

<210> SEQ ID NO 62
<211> LENGTH: 83
<212> TYPE: DNA
<213> ORGANISM: Artificial Sequence
<220> FEATURE:
<223> OTHER INFORMATION: EGFR bp2535-2616 858R wild sense strand

<400> SEQUENCE: 62
tgaaaacacc gcagcatgtc aagatcacag attttgggct ggccaaactg ctgggtgcgg    60
aagagaaaga ataccatgca gaa                                            83

<210> SEQ ID NO 63
<211> LENGTH: 83
<212> TYPE: DNA
<213> ORGANISM: Artificial Sequence
<220> FEATURE:
<223> OTHER INFORMATION: EGFR bp2535-2616 858R wild antisense strand

<400> SEQUENCE: 63
ttctgcatgg tattctttct cttccgcacc cagcagtttg gccagcccaa aatctgtgat    60
cttgacatgc tcgcctgttt tca                                            83

<210> SEQ ID NO 64
<211> LENGTH: 21
<212> TYPE: DNA
<213> ORGANISM: Artificial Sequence
<220> FEATURE:
<223> OTHER INFORMATION: CY2-w-probe

<400> SEQUENCE: 64
cattgaggac cgtgttcaag a                                              21

<210> SEQ ID NO 65
<211> LENGTH: 21
<212> TYPE: DNA
<213> ORGANISM: Artificial Sequence
<220> FEATURE:
<223> OTHER INFORMATION: CY2-w-antiprobe

<400> SEQUENCE: 65
tcttgaacac ggtcctctat g                                              21

<210> SEQ ID NO 66
<211> LENGTH: 23
<212> TYPE: DNA
<213> ORGANISM: Artificial Sequence
<220> FEATURE:
<223> OTHER INFORMATION: CY2-M-probe
```

```
<400> SEQUENCE: 66
ctcttgaaca cagacctcaa tgc                                          23

<210> SEQ ID NO 67
<211> LENGTH: 23
<212> TYPE: DNA
<213> ORGANISM: Artificial sequence
<220> FEATURE:
<223> OTHER INFORMATION: CY2m-antiprobe

<400> SEQUENCE: 67
gcattgagga ctgtgttcat gag                                          23

<210> SEQ ID NO 68
<211> LENGTH: 20
<212> TYPE: DNA
<213> ORGANISM: Artificial Sequence
<220> FEATURE:
<223> OTHER INFORMATION: CY2Fprimer

<400> SEQUENCE: 68
aattttggga tggggaagag                                              20

<210> SEQ ID NO 69
<211> LENGTH: 24
<212> TYPE: DNA
<213> ORGANISM: Artificial Sequence
<220> FEATURE:
<223> OTHER INFORMATION: CY2R-primer

<400> SEQUENCE: 69 gttttttctca actcctccac aagg                                        24

<210> SEQ ID NO 70
<211> LENGTH: 24
<212> TYPE: DNA
<213> ORGANISM: Artificial Sequence
<220> FEATURE:
<223> OTHER INFORMATION: CY3W-probe

<400> SEQUENCE: 70
gagaaggtca atgaatctct ggac                                         24

<210> SEQ ID NO 71
<211> LENGTH: 24
<212> TYPE: DNA
<213> ORGANISM: Artificial Sequence
<220> FEATURE:
<223> OTHER INFORMATION: CY3W-antiprobe

<400> SEQUENCE: 71
gtcctgagat acattgacct tctc                                         24

<210> SEQ ID NO 72
<211> LENGTH: 23
<212> TYPE: DNA
<213> ORGANISM: Artificial Sequence
<220> FEATURE:
<223> OTHER INFORMATION: CY3M-probe

<400> SEQUENCE: 72
agaaggtcaa ggaatctctg gac                                          23

<210> SEQ ID NO 73
```

```
<211> LENGTH: 23
<212> TYPE: DNA
<213> ORGANISM: Artificial Sequence
<220> FEATURE:
<223> OTHER INFORMATION: CY3m-antiprobe

<400> SEQUENCE: 73
gtcctgagat accttgacct tct                                         23

<210> SEQ ID NO 74
<211> LENGTH: 20
<212> TYPE: DNA
<213> ORGANISM: Artificial Sequence
<220> FEATURE:
<223> OTHER INFORMATION: CY3F-primer

<400> SEQUENCE: 74
ccacatgccc tacacagatg                                             20

<210> SEQ ID NO 75
<211> LENGTH: 25
<212> TYPE: DNA
<213> ORGANISM: Artificial Sequence
<220> FEATURE:
<223> OTHER INFORMATION: CY3R-primer

<400> SEQUENCE: 75
ccttgggaat gagatagttt ctgaa                                       25

<210> SEQ ID NO 76
<211> LENGTH: 58
<212> TYPE: DNA
<213> ORGANISM: Artificial Sequence
<220> FEATURE:
<223> OTHER INFORMATION: PARTIAL MUTANT 858 TEMPLATE

<400> SEQUENCE: 76
gcacccagca gtttggcccg cccaaaatct gtgatcttga catgctcgcc tgttttca    58

<210> SEQ ID NO 77
<211> LENGTH: 58
<212> TYPE: DNA
<213> ORGANISM: Artificial Sequence
<220> FEATURE:
<223> OTHER INFORMATION: PARTIAL WILD 858 TEMPLATE

<400> SEQUENCE: 77
gcacccagca gtttggccag cccaaaatct gtgatcttga catgctcgcc tgttttca    58

<210> SEQ ID NO 78
<211> LENGTH: 20
<212> TYPE: DNA
<213> ORGANISM: Artificial Sequence
<220> FEATURE:
<223> OTHER INFORMATION: EGFR Del-19 forward primer

<400> SEQUENCE: 78
tctggatccc agaaggtgag                                             20

<210> SEQ ID NO 79
<211> LENGTH: 19
<212> TYPE: DNA
<213> ORGANISM: Artificial Sequence
<220> FEATURE:
<223> OTHER INFORMATION: EGFR exon 21 primer-probe
<220> FEATURE:
<221> NAME/KEY: misc_feature
```

<222> LOCATION: (1)..(1)
<223> OTHER INFORMATION: 5'-CalRed610 label attached

<400> SEQUENCE: 79
tgaaaacacc gcagcatgt                                                    19

<210> SEQ ID NO 80
<211> LENGTH: 19
<212> TYPE: DNA
<213> ORGANISM: Artificial Sequence
<220> FEATURE:
<223> OTHER INFORMATION: EGFR exon 21 antiprobe
<220> FEATURE:
<221> NAME/KEY: misc_feature
<222> LOCATION: (19)..(19)
<223> OTHER INFORMATION: 3'-BHQ2 label attached

<400> SEQUENCE: 80
acatgctgtg gtgttttca                                                    19

<210> SEQ ID NO 81
<211> LENGTH: 24
<212> TYPE: DNA
<213> ORGANISM: Artificial Sequence
<220> FEATURE:
<223> OTHER INFORMATION: EGFR Del-19 iDDS probe
<220> FEATURE:
<221> NAME/KEY: misc_feature
<222> LOCATION: (1)..(1)
<223> OTHER INFORMATION: 5'-FAM probe attached

<400> SEQUENCE: 81
caaggaatta agagaagcaa catc                                              24

<210> SEQ ID NO 82
<211> LENGTH: 24
<212> TYPE: DNA
<213> ORGANISM: Artificial Sequence
<220> FEATURE:
<223> OTHER INFORMATION: EGFR Del-19 iDDS antiprobe
<220> FEATURE:
<221> NAME/KEY: misc_feature
<222> LOCATION: (24)..(24)
<223> OTHER INFORMATION: 3'-BHQ1 label attached

<400> SEQUENCE: 82
gatgttgcct ctcttaattc cttg                                              24

<210> SEQ ID NO 83
<211> LENGTH: 19
<212> TYPE: DNA
<213> ORGANISM: Artificial Sequence
<220> FEATURE:
<223> OTHER INFORMATION: EGFR TM790 F-primer

<400> SEQUENCE: 83
gcatctgcct cacctccac                                                    19

<210> SEQ ID NO 84
<211> LENGTH: 20
<212> TYPE: DNA
<213> ORGANISM: Artificial Sequence
<220> FEATURE:
<223> OTHER INFORMATION: EGFR Tm790 R-primer

<400> SEQUENCE: 84
gtctttgtgt tcccggacat                                                   20

```
<210> SEQ ID NO 85
<211> LENGTH: 23
<212> TYPE: DNA
<213> ORGANISM: Artificial Sequence
<220> FEATURE:
<223> OTHER INFORMATION: EGFR TM790 IDDS Probe
<220> FEATURE:
<221> NAME/KEY: misc_feature
<222> LOCATION: (1)..(1)
<223> OTHER INFORMATION: 5'-FAM label attached

<400> SEQUENCE: 85
tgagctccat gatgagttgc acg                                              23

<210> SEQ ID NO 86
<211> LENGTH: 23
<212> TYPE: DNA
<213> ORGANISM: Artificial Sequence
<220> FEATURE:
<223> OTHER INFORMATION: EGFR TM790 IDDS Antiprobe
<220> FEATURE:
<221> NAME/KEY: misc_feature
<222> LOCATION: (23)..(23)
<223> OTHER INFORMATION: 3'-BHQ1 label attached

<400> SEQUENCE: 86
cgtgcaactc ttcatgcagc tca                                              23

<210> SEQ ID NO 87
<211> LENGTH: 23
<212> TYPE: DNA
<213> ORGANISM: Artificial Sequence
<220> FEATURE:
<223> OTHER INFORMATION: Zipr Flu A F-primer

<400> SEQUENCE: 87
cttctaaccg aggtcgaaac gta                                              23

<210> SEQ ID NO 88
<211> LENGTH: 17
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: 5'-FAM label attached

<400> SEQUENCE: 88
gctttgaggg ggcctga                                                     17

<210> SEQ ID NO 89
<211> LENGTH: 17
<212> TYPE: DNA
<213> ORGANISM: Artificial Sequence
<220> FEATURE:
<223> OTHER INFORMATION: Antiprobe
<220> FEATURE:
<221> NAME/KEY: misc_feature
<222> LOCATION: (17)..(17)
<223> OTHER INFORMATION: 3'-BHQ1 label attached

<400> SEQUENCE: 89
tcagcccccc tcaaagc                                                     17

<210> SEQ ID NO 90
<211> LENGTH: 24
```

```
<212> TYPE: DNA
<213> ORGANISM: Artificial Sequence
<220> FEATURE:
<223> OTHER INFORMATION: Zipr Flu B R-primer

<400> SEQUENCE: 90
ctaattgtct ccctcttctg gtga                                        24

<210> SEQ ID NO 91
<211> LENGTH: 20
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (1)..(1)
<223> OTHER INFORMATION: 5'-CalRed610 label attached

<400> SEQUENCE: 91
cccaatttgg tcaagagcac                                             20

<210> SEQ ID NO 92
<211> LENGTH: 20
<212> TYPE: DNA
<213> ORGANISM: Artificial Sequence
<220> FEATURE:
<223> OTHER INFORMATION: Antiprobe
<220> FEATURE:
<221> NAME/KEY: misc_feature
<222> LOCATION: (20)..(20)
<223> OTHER INFORMATION: 3'-BHQ2 label attached

<400> SEQUENCE: 92
gtgctgatga ccaaattggg                                             20

<210> SEQ ID NO 93
<211> LENGTH: 16
<212> TYPE: DNA
<213> ORGANISM: Artificial Sequence
<220> FEATURE:
<223> OTHER INFORMATION: KRAS iDDS P
<220> FEATURE:
<221> NAME/KEY: misc_feature
<222> LOCATION: (1)..(1)
<223> OTHER INFORMATION: 5'-FAM label attached

<400> SEQUENCE: 93
cctacgccac cagctc                                                 16

<210> SEQ ID NO 94
<211> LENGTH: 16
<212> TYPE: DNA
<213> ORGANISM: Artificial Sequence
<220> FEATURE:
<223> OTHER INFORMATION: KRAS iDDS A
<220> FEATURE:
<221> NAME/KEY: misc_feature
<222> LOCATION: (16)..(16)
<223> OTHER INFORMATION: 3'-BHQ1 label attached

<400> SEQUENCE: 94
gaggtggtgg cgtagg                                                 16

<210> SEQ ID NO 95
<211> LENGTH: 22
<212> TYPE: DNA
<213> ORGANISM: Artificial Sequence
<220> FEATURE:
```

```
<223> OTHER INFORMATION: KRAS ZIPR P
<220> FEATURE:
<221> NAME/KEY: misc_feature
<222> LOCATION: (1)..(1)
<223> OTHER INFORMATION: 5'-HEX attached

<400> SEQUENCE: 95
tggatcatat tcgtccacaa aa                                              22

<210> SEQ ID NO 96
<211> LENGTH: 22
<212> TYPE: DNA
<213> ORGANISM: Artificial Sequence
<220> FEATURE:
<223> OTHER INFORMATION: KRAS ZIPR P
<220> FEATURE:
<221> NAME/KEY: misc_feature
<222> LOCATION: (22)..(22)
<223> OTHER INFORMATION: 3'-BHQ1 attached

<400> SEQUENCE: 96
ttttgaggac gaatatgatc ca                                              22

<210> SEQ ID NO 97
<211> LENGTH: 25
<212> TYPE: DNA
<213> ORGANISM: Artificial Sequence
<220> FEATURE:
<223> OTHER INFORMATION: KRAS Flanking primer

<400> SEQUENCE: 97
cctgctgaaa atgactgaat ataaa                                           25

<210> SEQ ID NO 98
<211> LENGTH: 17
<212> TYPE: DNA
<213> ORGANISM: Artificial Sequence
<220> FEATURE:
<223> OTHER INFORMATION: G-Force probe:antiprobe structure
<220> FEATURE:
<221> NAME/KEY: misc_feature
<222> LOCATION: (1)..(1)
<223> OTHER INFORMATION: 5'-FAM label
<220> FEATURE:
<221> NAME/KEY: misc_feature
<222> LOCATION: (8)..(9)
<223> OTHER INFORMATION: spacer 18 which is an 18 atom hexaethylene
      glycol chain is inserted between nucleotides 8 and 9

<400> SEQUENCE: 98
cccctccaag gaggggg                                                    17
```

PROBE:ANTIPROBE COMPOSITIONS FOR HIGH SPECIFICITY DNA OR RNA DETECTION

CROSS-REFERENCE TO RELATED APPLICATIONS

This application is a continuation-in-part under 37 C.F.R. § 1.120 of international application PCT/US2012/055620, filed Sep. 14, 2012, which claims benefit of priority under 37 C.F.R. § 1.119(e) of provisional application U.S. Ser. No. 61/534,925, filed Sep. 15, 2011, the entirety of both of which is hereby incorporated by reference.

BACKGROUND OF THE INVENTION

1. Field of the Invention

This disclosure relates to the field of nucleic acid probe technology, and more specifically to compositions and methods to identify and quantify DNA or RNA sequences. In particular it relates to the labeling and detection of gene targets during or post amplification.

2. Description of the Related Art

The detection of targeted polynucleotide sequences is usually based on methods that hybridize labeled DNA probes to a target sequence of interest. To work effectively, the probe-target hybridization products must be washed after hybridization to remove unbound probes and probes that are weakly bound to non-specific targets. However, under the conditions of real-time PCR (U.S. Pat. Nos. 4,965,188; 5,210,015; 5,487,972; 5,538,848), a wash step is not feasible, and thus novel probes had to be devised that selectively generate signaling when they are bound to a matching target and that have diminished or quenched signaling when they are unbound and floating free in solution. To achieve this end, there has been reliance on probes that employ the excitation and transfer of fluorescent energy between a donor and an acceptor molecule, such as between two fluorophores, or between a fluorophore and a quencher ([Didenko V, (2001) *Biotechniques* 31:1106-1121; Chen et al., (1997) *Proc. Natl. Acad. Sci. USA* 30: 94: 10756-10762). The fluorescence emission spectrum of the donor should overlap the absorption or excitation spectrum of the acceptor. The excited-state energy of the fluorescent donor is then transferred to the acceptor when they are in close proximity (10 to 100 angstroms). However, if the acceptor molecule is fluorescent, it provides an emitted signal at a longer wavelength. If the acceptor molecule is an effective quencher, fluorescent signaling is significantly diminished and may be essentially turned off.

TAQMAN® and molecular beacon probes are common probes of this type for real-time PCR detection. In both cases, they serve as an internal probe that is used in conjunction with a pair of opposing primers that flank the target region of interest. The primers amplify the target segment and the probe selectively binds to an identifying sequence between the primer sites, thereby causing increases in fluorescent signaling relative to increases in target frequency. While these probe systems are similar in effect, they employ different detection mechanisms.

A TAQMAN® probe comprises a synthetic oligonucleotide of about 20 to 30 bases that complements a target sequence, and which is labeled on opposing ends with a fluorescent donor and an acceptor (U.S. Pat. No. 5,538,848). Typically, the 5' end will have a shorter wavelength fluorophore such as fluorescein and the 3' end is labeled with a longer wavelength emitting fluorophore (e.g. TAMRA®) or a non-fluorescent quencher such as BLACK HOLE QUENCHER®. Internal quenchers have also been used. While the TAQMAN:® patent has expired, this technology still remains the dominant probe system for real time PCR.

Molecular beacon probes also use fluorescent interactions to detect and quantify a PCR product, with each probe typically having a 5' fluorescent-labeled end and a 3' quencher-labeled end (U.S. Pat. No. 5,925,517; Tyagi et al., (1996) *Nat. Biotechnology* 14: 303-308). However, molecular beacon probes further include short end segments of about 5 to 7 bases that are complementary and will bind together in solution, forming a stem-loop structure wherein the quencher and fluorophore-labeled ends are brought together and signaling is suppressed.

SCORPION® probes also provide a stem-loop detection mechanism similar to molecular beacons, except that the probe also has a segment attached that serves as an amplification primer (Whitcombe et al., (1999) *Nat. Biotechnol.* 17: 804-807; U.S. Pat. No. 6,326,145). These probes maintain a stem-loop configuration in the unhybridized state with the fluorophore quenched. When denaturation occurs again followed by annealing, the probe segment binds to the template, thereby opening the stem-loop structure and releasing fluorescence.

Similar to SCORPION®, SUNRISE® probes comprise a primer attached to a hairpin probe that is extended during amplification. This separates the internal quencher label from the 5' terminal fluorophore (Nazarenko et al., (1997) *Nucl. Acids Res.* 25: 2516-2521).

Conventional dual-labeled probes require selective design and are costly. Their synthesis is difficult and they require manual post-synthesis addition of at least one label as well as high pressure liquid chromatography purification. TAQMAN® and molecular beacon probes also require two opposing primers that flank the probe. To function effectively during the annealing step, TAQMAN® and molecular beacon probes must be longer and have a Tm (melting temperature) that is 5 to 10 degrees higher than the primers since the probe must bind firmly to the target before extension. This requirement makes it difficult to design or develop dual-labeled probes that can selectively detect SNPs (single nucleotide polymorphisms) or single base mutations, and consequently, false positives are a common problem.

FISH (fluorescent in situ hybridization) techniques require four processing steps: 1) the preparation of labeled probes, 2) probe hybridization to fixed denatured targets, 3) the washing of unbound probes, and 4) fluorescent excitation and detection (Barch M. J, editor. "The ACT Cytogenetics Laboratory Manual" 2nd ed. New York: Raven Press; 1991). Careful washing steps are critical to effective detection since the signal to noise ratio is highly dependent on the stringency of washing. Excessive washing can greatly reduce signaling.

Microarray detection resembles FISH detection. Arrays are typically based on printing glass or silicon substrates with bound oligonucleotide cDNA probes; applying fluorescent-labeled DNA or RNA targets which must be hybridized to the probes; washing the arrays stringently; and then detecting the bound targets, usually by laser scanning (Schena et al., (1995) *Science* 270: 467-470; Heller et al., (1997) *Proc. Natl. Acad. Sci. U.S.A.* 94: 2150-2155). Like FISH probes, the wash steps are again complex and time consuming. However, the preparation and labeling of the targets are costly since each target sample is unique, limiting its usefulness for routine microarray-based assays, especially for clinical diagnostics.

Thus there is a recognized need in the art for improved probe systems to detect a target nucleotide sequence. Particularly, the prior art is deficient in probe systems, methods and compositions that utilize a probe:antiprobe to selectively detect a target-specific RNA or DNA sequence with single base variant discrimination. The present invention fulfills this longstanding need and desire in the art.

SUMMARY OF THE INVENTION

The present disclosure is directed to probe systems suitable for real-time and end-point detection of DNA or RNA sequences with particular emphasis on probes that can discriminate single base variants such as SNPs and point mutations. The present disclosure is especially directed at providing probes suitable for qPCR (real-time PCR) in which small gene segments are exponentially amplified and quantitatively detected. The present disclosure provides a series of probe systems that are structurally and functionally related but which diverge in respective degrees of specificity and or sensitivity, and which can be combined to provide new diagnostic or quantitative capabilities.

Particularly, the disclosure is directed to a probe:antiprobe system comprising two labeled oligonucleotides, a probe and an antiprobe, that can interact together. The probe sequence is complementary to the intended target sequence, and the antiprobe sequence is complementary to the probe except for comprising at least one mismatched base in a non-terminal position. The antiprobe is designed to provide an error checking mechanism for the probe. In some embodiments, the probe is generally labeled with a fluorescent emitter and the antiprobe is generally labeled with a fluorescent modulator, such as a quencher, although such labeling can be reversed and other components, such as a second fluorophore, can serve as a fluorescent modulator. In such embodiments, when probe and antiprobe are bound together, the interacting label moieties are proximate and signaling is diminished, but when the probe binds to a complementary target, fluorophore signaling is released.

This probe:antiprobe system can be configured to enable discrimination of two target sequences that differ by only one base. Accordingly, the probe and antiprobe sequences are engineered to achieve three separate hybridization affinity levels in solution: (i) a first high affinity level between the probe and the intended target, (ii) a second intermediate affinity level between the probe and the antiprobe which is determined by the type and position of the mismatch placed in the antiprobe, and (iii) a third lower affinity level between the probe and an incorrect target that differs by at least one base. The expected hybridization affinity levels are assessed by calculating the Tm and the ΔG of the duplexes expected. The length, sequence and mismatch placement for the components are designed and configured so that the hybridization affinity of the probe:intended target duplex is higher than the affinity of the probe:antiprobe duplex by about 4 or more degrees in Tm and about −2 or more kcal/mol in ΔG, and so that the affinity of the probe:antiprobe duplex is higher than the affinity of the probe:incorrect target duplex by about another 4 or more degrees in Tm and about another −2 or more kcal/mol in ΔG. However, in cases where the inherent thermodynamic difference between the probe:intended target duplex and the probe:incorrect target duplex is limited, the probe may also be modified with an intentional mismatch, advantageously placed about two bases away from the single base variant expected. This probe modification diminishes the hybridization affinity between the probe and the incorrect target due to the proximity of the probe mismatch to the sequence mismatch, the SNP or single base mutant of interest, in the incorrect target. With these various thermodynamic designs, the probe:antiprobe system can achieve discrimination of single base variants and can maintain such discrimination over a range of hybridization conditions and annealing temperatures—particularly when employed for real-time PCR.

The disclosure is directed further to a probe:antiprobe system further comprising alternate compositions where the probe is designed to serve as a primer-probe and it replaces one primer, or where the probe serves as an internal probe in conjunction with two flanking primers. The disclosure is directed further to a modified probe:antiprobe composition in which the antiprobe is structurally joined to one primer, and this change creates linear versus sigmoid amplification curves by real-time PCR.

The disclosure is directed further to a probe:antiprobe system combined with a unlabeled blocking probe to enhance the amplification and detection of rare sequence variants such as mutant cancer cells embedded in normal tissue.

The disclosure is directed further to modified probe: antiprobe compositions for detecting gene segments amplified by an isothermal method, including means for amplification on an array substrate.

The disclosure is directed further to methods for combining two or more probes together, to detect different target sites simultaneously, or in order to separately detect two aspects of the same target.

BRIEF DESCRIPTION OF THE DRAWINGS

FIG. 1A schematically illustrates the general DDS probe structure and mechanism.

FIG. 1B schematically illustrates the internal DDS (iDDS) system according to the disclosure.

FIG. 1C schematically illustrates the terminal ZIPR DDS system.

FIG. 3A schematically illustrates the Two step "Wild Terminator" ("WTx") system of the disclosure.

FIG. 3B schematically illustrates the One step "Wild Terminator" ("WTx") system of the disclosure.

FIG. 4A schematically illustrates terminal DDS probes combined with ISAM isothermal amplification.

FIG. 4B schematically illustrates internal DDS probes combined with ISAM isothermal amplification.

FIG. 4C schematically illustrates DDS probes with on-chip ISAM amplification.

FIG. 7A illustrates the region of exon 21 of the EGFR gene comprising base pair positions 2535-2616 that were amplified to detect the L858R SNP site cancer marker. The mutant template (top) and the wild template (bottom) are shown with the variable 858 SNP site in bold and the common primer sequences in bold.

Figure 2A:
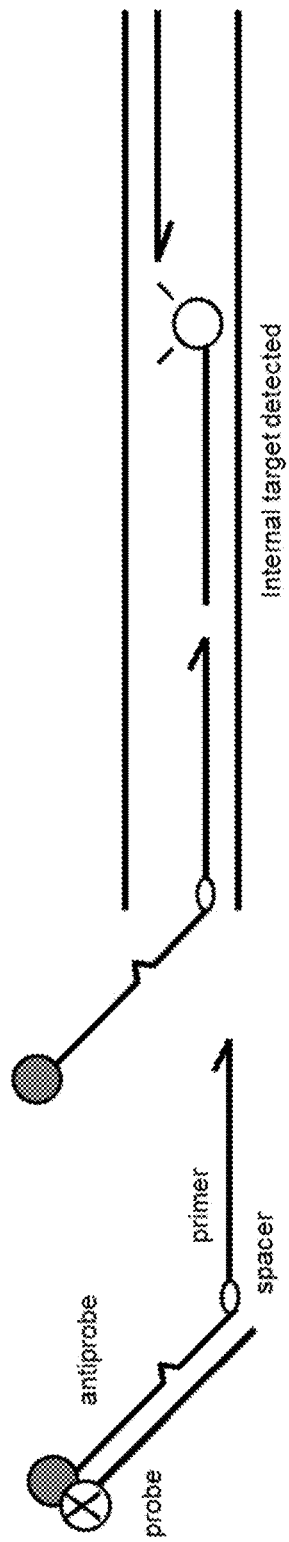
FIG. 2A schematically illustrates the FLIP DDS system.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION OF THE INVENTION

Before the present disclosure is described in greater detail, it is to be understood that this disclosure is not limited to the particular embodiments described. In addition, the terminology employed is for the purpose of describing particular embodiments, and is not intended to be limiting. The scope of the disclosure is limited only by the claims. Unless defined otherwise, all technical and scientific terms used herein have the same meaning as commonly understood by one of ordinary skill in the art in this field. Although methods similar to those described herein can also be used in the practice or testing of the present disclosure, the preferred methods and materials are now described.

As will be apparent to those of skill in the art, each of the individual embodiments described has discrete components and features that may be readily separated from or combined with the features of any of the other several embodiments without departing from the scope or spirit of the present disclosure. Any recited method can be carried out in the order of events recited or in any other order that is logically possible. Embodiments of the present disclosure will employ, unless otherwise indicated, techniques of medicine, organic chemistry, biochemistry, molecular biology, pharmacology, and the like, which are within the skill of the art. Such techniques are explained fully in the literature.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or analogs or derivatives thereof or method steps as discussed above. Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The following abbreviations are used herein: DDS, DNA Detection Switch; iDDS, internal DNA Detection Switch; EGFR, epidermal growth factor receptor; qPCR, quantitative PCR (real-time PCR); LNA, locked nucleic acid; PNA, peptide nucleic acid; FISH, Fluorescent In Situ Hybridization; Tm, melting temperature; ISAM, isothermal amplification method; SNP, single nucleotide polymorphism, ZNA, Zip nucleic acid.

The terms and phrases used herein have their art-recognized meaning which can be found in standard texts known to those skilled in the art. The following definitions are provided.

The term "nucleotide" as used herein refers to a sub-unit of a nucleic acid, and it includes not only natural purine and pyrimidine bases, e.g., adenine (A), thymine (T), cytosine (C), guanine (G), or uracil (U), but also modified or analog bases.

The term "oligonucleotide" as used herein refers to a chain of linked nucleotide residues. Oligonucleotides may be chemically synthesized and may be used as primers or probes. The terms "oligonucleotide" and "polynucleotide" as used herein may also refer to modified or unmodified RNA or DNA.

The term "primer" as used herein refers to an oligonucleotide complementary to a DNA segment to be amplified or replicated. A primer hybridizes or anneals to the template DNA and is used by a polymerase to start the replication/amplification process. By "complementary" is meant that the primer sequence can form a stable hydrogen bond complex with the template.

The term "probe" as used herein refers to oligonucleotides that are nucleic acid sequences of variable length, used in the detection of identical, similar, or complementary nucleic acid sequences by hybridization. An oligonucleotide used as a detection probe may be labeled with a detectable moiety such as fluorescent or chemiluminescent compounds.

The term "label moiety" refers to a label molecule that is incorporated indirectly or directly into an oligonucleotide to facilitate detection. Various fluorescent or quencher molecules are commonly used for probe labeling.

The term "fluorophore" as used herein refers to any reporter group whose presence can be detected by its light emitting properties.

The terms "fluorescence quencher" or "quencher" as used herein refers to molecules that interfere with or absorb the fluorescence emitted by a nearby fluorophore.

The term "quench" as used herein refers to reducing the signal produced by a label molecule to a significantly lower level or to an undetectable level.

The term "modulated detectable signal" as used herein refers to a signal emitted by a label moiety that is reduced in intensity or otherwise changed such as a change in wavelength.

The term "hybridization" as used herein refers to the process of association of two nucleic acid strands to form an anti-parallel duplex stabilized by hydrogen bonding between opposing strands. The hybridized strands are called a "duplex."

The term "hybridization affinity" refers to the degree of chemical attraction between two nucleic acid segments based on the binding of matching base pairs between them. Hybridization affinity varies with the length and sequence of the duplex.

The term "denaturation" refers to the separation of complementary DNA strands forming a duplex, typically by heat treatment.

The term "melting temperature "($T_m$)" refers to a temperature at which hybridized duplexes can denature or dehybridize and return to their single-stranded state. $T_m$ can serve as a measure of hybridization affinity. Similarly, the term delta-G or $\Delta G$ (Gibbs free energy) as measured in –kcal/mol can serve as an alternative indicator of hybridization affinity, with increasing affinity being described with increasingly negative $\Delta G$ values.

The term "complementary" refers to the existence of a sufficient number of matching bases between two sequence segments so that they can specifically bind or hybridize together.

The term "mismatched base position" as used herein refers to a duplex in which one or more opposing nucleotide bases do not pair in a complementary manner. A mismatch can be due to addition, deletion or substitution of a natural or non-natural base, or a spacer.

The term "locked nucleic acid (LNA)" as used herein refers to a modified nucleotide with an extra bridge connecting the 2' oxygen and 4' carbon. LNA and similar modified nucleotides can be incorporated into an oligonucleotide to increase the stability of a nucleic acid duplex.

The term "spacer" as used herein refers to any molecular entity such as, but not limited to, a multi-carbon spacer, at least one artificial abasic nucleotide, a peptide, or any other abasic extended moiety that may be attached to the end of an oligonucleotide or that can attach two oligonucleotides together, providing means to block polymerase progress over the spacer.

The terms "target" and "target nucleotide sequence" refers to a polynucleotide sequence that it is desired to detect. A "target" may refer to any nucleic acid isolated from a plant, an animal or human subject, a bacterial, viral, or unicellular eukaryotic organism, either from the whole organism, a tissue thereof, or from a cultured cell or cells.

The term "signature sequence" refers to a target nucleotide sequence that serves to identify a gene, a species, or an organism of interest.

The term "template" as used herein refers to a target polynucleotide strand, for example, a naturally-occurring DNA strand, which a polymerase uses as a means of recognizing which nucleotide it should next incorporate into a growing strand. Templates may be single or double-stranded. In applications of the present disclosure, the template may become modified or extended by the incorporation of an extended primer in the amplification process.

The terms "DNA amplification" and "amplification" refers to any process that increases the copies of a specific DNA sequence by enzymatic amplification. A commonly used process is the polymerase chain reaction (PCR) as described in U.S. Pat. Nos. 4,683,195 and 4,683,202. PCR involves the use of a thermostable DNA polymerase, primers, and heating cycles, which separate the DNA strands and exponentially amplify a gene region of interest.

The term "Polymerase Chain Reaction" or "PCR" as used herein refers to a thermocyclic, polymerase-mediated, DNA amplification reaction employing template molecules, oligonucleotide primers complementary to the template molecules, a thermostable DNA polymerase, and deoxyribonucleotides, and it involves three repeated processes (denaturation, hybridization, and primer extension) that are performed at distinct temperatures and steps. In many embodiments, the hybridization and extension processes can be performed concurrently. A PCR blocker or blocking sequence may be utilized to block polymerase extension.

The term "polymerase" as used herein refers to an enzyme that catalyzes the sequential addition of monomeric units to a polymeric chain. In embodiments of this disclosure, the "polymerase" will work by adding monomeric units whose identity is determined by a complementary template of a specific sequence.

The term "qPCR" refers to a real-time polymerase chain reaction, also called quantitative real time polymerase chain reaction (Q-PCR/qPCR/qrt-PCR) which is used to amplify and simultaneously detect the quantity of a targeted DNA molecule. The quantity can be expressed as a number of copies or a relative amount normalized to the input DNA. Unlike standard PCR, detection proceeds in real time PCR as the reaction progresses. Two common detection methods for qPCR are: (1) non-specific fluorescent dyes that intercalate double-stranded DNA, and (2) sequence-specific oligonucleotides that are labeled with a fluorescent reporter.

The term "probe:antiprobe" as used herein refers to a pair of oligonucleotides having nearly or exactly the same number of base positions and having sequences substantially complementary such that, in the absence of a third nucleotide sequence hybridizing to the probe or the antiprobe, said oligonucleotides can form a duplex. It is within the scope of the disclosure for the probe and antiprobe oligonucleotides to be separate molecules or be linked as a region of a single molecular entity.

The term "multi-base non-hybridized region" as used herein refers to a region of a duplexed nucleic acid comprising two or more opposing bases that are mismatched, thereby forming a "hybridization bubble" of non-duplexed bases.

The term "selectively detecting" as used herein refers to the ability of oligonucleotide probes of the disclosure to distinguish one nucleotide sequence from another by selectively hybridizing to one sequence under the same or similar hybridizing conditions and, when bound to one sequence and not the other, to provide a detectable signal indicating such binding.

The term "system" as used herein generally refers to a combination of at least two oligonucleotides that cooperate to selectively hybridize to a target nucleotide sequence and generate a detectable signal indicating the presence of the target sequence. The system may further include primer oligonucleotides useful for the polymerase amplification of a nucleotide sequence from a template nucleic acid to form an amplified amplicon, said amplicon comprising a nucleotide sequence suspected of comprising a target sequence.

The term "terminator" probe as used herein refers to a blocking probe, that is typically configured to block the amplification and detection of targets with a wild type sequence, while it allows the amplification and detection of low frequency mutant variants that differs by a single base.

The term "generic sequence" as used herein refers to a sequence that is not complementary to the target sequence and that can serve a universal function that is applicable to multiple oligonucleotide based components. For example, a generic sequence can serve as a complementary binding sequence between two subunits of a probe, or alternatively a generic sequence can serve as a universal primer that can amplify a targeted region by virtue of having appended a matching primer site to the end of the targeted amplicon.

Unless otherwise defined, all technical and scientific terms used herein have the same meaning as commonly understood by one of ordinary skill in the art of molecular biology. Although methods and materials similar or equivalent to those described herein can be used in the practice of the present disclosure, suitable methods and materials are described herein.

In one embodiment of the present invention there is provided a probe system for the selective detection of a target-specific nucleotide sequence, comprising a) a primary probe having a polynucleotide sequence complementary to a first target nucleotide sequence and a first label moiety attached thereto; and b) a secondary antiprobe having a polynucleotide sequence complementary to the probe except for at least one mismatched base in a non-terminal position and a second label moiety that is attached to the antiprobe or is a region of the antiprobe; wherein the probe sequence imparts a hybridization affinity for the first target nucleotide sequence that is greater than the hybridization affinity of the probe for the antiprobe, and wherein the hybridization affinity of the probe and antiprobe is greater than the hybridization affinity of the probe for a second target nucleotide sequence of interest, whereby: (i) in the presence of the first target nucleotide sequence, the probe and the first target nucleotide sequence form a probe:first target nucleotide sequence duplex such that non-interaction between the first and the second label moieties comprises a first detectable signal; (i) in the absence of the first target nucleotide sequence, the probe and the antiprobe form a probe:antiprobe duplex, such that interaction between the first and the second label moieties comprises a modulated detectable signal distinguishable from the first detectable signal; and (iii) in the presence of a second target nucleotide sequence differing from the first target sequence by at least one mismatched base, the probe and the antiprobe preferentially form a duplex.

Further to this embodiment the probe sequence may be further configured with a mismatched base position about two bases away from the mismatch between the second target nucleotide sequence and the probe sequence; wherein the two mismatched bases comprise an internal two or three bases non-hybridized region in a probe:second target nucleotide sequence duplex, wherein said probe:second target nucleotide sequence duplex has a hybridization affinity that is less than the hybridization affinity of the probe:antiprobe duplex.

In a second further embodiment the probe system may comprise a polymerase extension blocking sequence linked to an unlabeled 3' end of the probe or the antiprobe or a pair of flanking primers specific for first target nucleotide sequence amplification or a combination thereof. In this further embodiment the probe sequence may be complementary to an internal target sequence and is about 20 to about 25 nucleotides in length and the antiprobe sequence is about 10 to about 15 nucleotides in length; and wherein one or two of the flanking primers further comprises a 5' RNA polymerase promoter sequence, where the probe system further comprises a RNA polymerase promoter enzyme, a reverse transcriptase enzyme and RNaseH enzyme. Also, in this further embodiment the primer may be attached to a solid substrate.

Further still to this further embodiment the probe system may comprise an unlabeled blocking terminator probe comprising (i) an oligonucleotide complementary to the second target nucleotide sequence, said second target nucleotide sequence comprising a high frequency target and having a sequence substantially similar but not identical to the first target nucleotide sequence comprising a low frequency target, (ii) a modified 5' end resistant to exonuclease digestion, (iii) a modified 3' end resistant to polymerase extension; wherein the unlabeled terminator probe has a Tm and ΔG that differs from the Tm and ΔG of the primers or the probes or both by at least about 5 kcal/mol in ΔG and by at least about 5° C. in Tm. In this further embodiment the blocking terminator probe may comprise one or more non-natural nucleotides or a minor groove binder (MGB) or a combination thereof.

In an aspect of this further embodiment the frequency of the second target nucleotide sequence exceeds the frequency of the first target nucleotide sequence by a ratio of at least 20:1 and wherein said probe system comprises a first pre-amplification subsystem and a second re-amplification and detection subsystem, where the first pre-amplification subsystem may comprise (i) the unlabeled blocking terminator probe, and (ii) a primer pair specific for the first and second target nucleotide sequence regions amplification; and where the second re-amplification and detection subsystem may comprise (i) a dilute aliquot of an amplification product producible by the first subsystem wherein the dilute aliquot comprises about 0.05% or less of the amplification product; (ii) a first probe:antiprobe complementary to the first target nucleotide sequence or the first probe:antiprobe and a second probe:antiprobe complementary to the second target nucleotide sequence, and (iii) a primer pair specific for the first and second target nucleotide sequence regions amplification.

Particularly in this second further embodiment and aspects thereof the first target nucleotide sequence is a variable nucleotide base position of exon 21 of the EGFR gene and wherein the probe sequences are shown in SEQ ID NOS: 7 and 9, the antiprobe sequences are shown in SEQ ID NOS: 8 and 10, the primer sequences are shown in SEQ ID NOS: 11-12 and 39-40, and the blocking sequence is shown is SEQ ID NO: 41.

In a third further embodiment the probe system may comprise a first primer sequence at a 3' end of the antiprobe and a second primer, wherein the antiprobe is linked to the first primer by an abasic spacer region, and wherein said first and second primer sequences are configured to amplify a region comprising the first target nucleotide sequence.

In a fourth further embodiment the labeled probe comprises a primer sequence, where the probe system further comprises a second primer, wherein the labeled primer-probe and the second primer are configured to enable target sequence amplification such that, upon incorporation of the labeled primer-probe into a target sequence amplicon, a detectable signal is enabled. In this further embodiment the labeled primer probe may comprise (i) a 5' fluorescent-labeled probe segment comprising a cytosine-rich sequence of about 7 to 9 bases, (ii) an abasic spacer, (iii) a guanine-rich antiprobe sequence complementary to the cytosine-rich sequence region, and, (iv) the primer sequence. Further still the probe system may comprise an RNA polymerase promoter sequence at the 5' end of one or both primers, and comprising an RNA polymerase promoter enzyme, a reverse transcriptase enzyme and RNaseH enzyme; wherein the labeled primer-probe or a labeled primer-probe comprising a 5' RNA polymerase promoter sequence and the second primer enable target sequence amplification such that a target sequence amplicon has an emittable signal at one or both ends thereof and RNA transcription is enabled at one or both ends thereof. In these further embodiments an antiprobe may comprise a sequence matching the primer-probe sequence or a sequence complementary to the RNA polymerase promoter sequence. Also the 5' end of one or both primers may be attached to a solid substrate.

In this fourth further embodiment the labeled primer-probe may comprise a 3' primer sequence and a 5' generic sequence not complementary to the target sequence and the antiprobe comprises a sequence complementary to the generic sequence of the labeled primer-probe. Alternatively, the labeled primer-probe comprise a generic primer sequence not complementary to the target sequence and wherein the antiprobe may comprise a sequence complementary to the labeled primer-probe, where the probe system further comprises an unlabeled linker-primer oligonucleotide having a 3' primer sequence complementary to the target sequence and a 5' linker sequence that partially or fully comprises the primer sequence of the primer-probe.

In a fifth further embodiment the probe system may comprise one or more additional probes each having a label moiety attached thereto and each comprising a polynucleotide sequence selectively hybridizable to a different target nucleotide sequence; and wherein the label moieties have two or more different detectable signals or the same detectable signal; and wherein the two or more target nucleotide sequences are flanked by one common primer pair or by two or more primer pairs. In one aspect of this further embodiment a first probe may be a labeled primer-probe, where the probe system further comprises a second primer such that the first probe and the second primer enable amplification of a first amplicon comprising a first label having an emittable signal relative to amplicon frequency and wherein a second probe is a second labeled primer-probe or an internal probe comprising a second label and a sequence complementary to a target sequence that comprises a variable sequence segment of the first amplicon or a variable sequence elsewhere in a nucleic acid template such that a difference in signaling between the first primer-probe and the second probe is an indicator of the frequency of the variable sequence relative to the frequency of the first amplicon. In this aspect the variable sequence may be a multi-base deletion within codons 746 to 753 of exon 19 of the EGFR gene, where the probe system comprises at least one unlabeled primer, and two probe:antiprobe sets with different labeling; wherein the first probe:antiprobe set comprises a primer-probe complementary to a non-specific first sequence and the second probe set is complementary to a wild sequence at the exon 19 deletion site and inhibits or excludes detection of target templates comprising a multi-base deletion within codons 746 to 753 of exon 19 of the EGFR gene such that a comparison of relative signaling of the two probe:antiprobe sets is an indicator of the presence and frequency of an exon 19 deletion. In a representative example the non-specific probe:antiprobe-primer set is SEQ ID NOS.: 56, 57 and 53, or SEQ ID NOS.: 79, 80 and 12; and wherein the deletion-19 wild-only probe:antiprobe-primer set is SEQ ID NOS.: 81, 82, and 53, or SEQ ID NOS.: 54, 55 and 53 or wherein each non-specific probe:antiprobe-primer set and the deletion-19 wild-only probe:antiprobe-primer set further comprise SEQ ID NO.: 78.

In all embodiments and aspects thereof the probe:first target nucleotide sequence duplex and probe:antiprobe duplex may differ in hybridization affinity by at least about 2 kcal/mol in ΔG and by at least about 4° C. in $T_m$; and wherein the probe:second target nucleotide sequence duplex and probe:first target nucleotide sequence duplex differ in hybridization affinity by at least about 4 kcal/mol in ΔG and at least about 8° C. in $T_m$. Also, in all embodiments and aspects the probe or antiprobe comprises one or more non-natural nucleotides or a minor groove binder (MGB) or a combination thereof. In addition one of the first and second label moieties is a fluorescence emitter and the other of the label moieties may comprise a fluorescence modulator selected from the group consisting of a quencher compound, a fluorescent compound, a metallic particle, and a guanine-rich conjugate. Alternatively, the probe may comprise a fluorescence emitter and either a fluorescence modulator or a second fluorescent emitter, and wherein the antiprobe comprises a fluorescence modulator, a fluorescence modulator and a fluorescence emitter or two fluorescence modulators. Furthermore the probe may be attached to a solid substrate.

In all embodiments and aspects thereof the probe and antiprobe may comprise the nucleic acid sequences selected from the group consisting of: SEQ ID NOS.: 1 and 2, SEQ ID NOS.: 3 and 4, SEQ ID NOS.: 7 and 8, SEQ ID NOS.: 9 and 10, SEQ ID NOS.: 13 and 14, SEQ ID NOS.: 17 and 18, SEQ ID NOS.: 19 and 20, SEQ ID NOS.: 23 and 24, SEQ ID NOS.: 36 and 37, SEQ ID NOS.: 54 and 55, SEQ ID NOS.: 56 and 57, SEQ ID NOS.: 64 and 65, SEQ ID NOS.: 66 and 67, SEQ ID NOS.: 70 and 71, SEQ ID NOS.: 72 and 73, SEQ ID NOS.: 79 and 80, SEQ ID NOS.: 81 and 82, SEQ ID NOS.: 85 and 86, SEQ ID NOS.: 88 and 89, and SEQ ID NOS.: 91 and 92.

In another embodiment of the present invention there is provided a method for selectively detecting a target nucleotide sequence, comprising the steps of obtaining a biological sample from a human, an animal or an organism; contacting the biological sample with the labeled probe and labeled anti-probe comprising the probe system as described supra; and detecting a signal emitted by the duplex formed upon contacting the biological sample; wherein a type of the signal emitted is dependent on the duplex formed, thereby selectively detecting the target nucleotide sequence. Further to this embodiment the method comprises adding one or more primers to the probe system; and pre-amplifying the target nucleotide sequence.

The probe systems, compositions and methods of the present disclosure provide sensitive and specific detection of DNA or RNA target sequences, particularly for assessing PCR products that are amplified and detected by real-time PCR (qPCR). Several embodiments of the present disclosure facilitate the discrimination of single base variants (single nucleotide polymorphisms-SNPs) that distinguish bacterial and viral pathogens, cancers and genetic conditions, including drug resistant or drug sensitive variants or mutants that defy detection with ordinary real-time PCR probe systems or with hybridization-based microarray probes. Other embodiments facilitate the detection of two aspects of the same amplicon, such as a primer sequence in common and an internal SNP that may be variant, in order to determine the relative frequency of such variant sequences in a sample.

A particularly useful application of the probe:antiprobe systems according to the present disclosure are particular embodiments that selectively enhance the amplification and detection of a specific target sequence in the presence of a significantly greater proportion of a similar sequence differing from the target by just one mismatched base. For example, a biological sample may be obtained from a human or animal patient having a cancer, where the population of cells in a biopsy sample consists of a much greater percentage of normal cells than cancer cells. It is important, therefore, to provide a detectable signal corresponding to the small number of cancerous cells while avoiding false positive signals from the normal cells. Importantly, in such situations, the cancerous cell may differ from the normal cells by a single nucleotide polymorphism. The systems of the present disclosure, therefore, are advantageous in selectively amplifying and detecting target nucleotide sequences from the minority of cells having the single base change of interest such as a cancer-associated SNP and not the dominant normal (wild-type) sequence. The systems of the disclosure, for example, can detect at least as low as 0.2% of a target species containing a single base mutant in the midst of about 99.8% of a non-mutant target species.

The present disclosure encompasses embodiments of a probe:antiprobe composition, herein termed a DNA Detection Switch (DDS) probe, comprising two labeled oligonucleotides, a probe oligonucleotide and an antiprobe oligonucleotide, that are complementary in sequence and identical in length and that, in the absence of a target nucleotide sequence complementary to the probe, interact to form a duplex. The probe comprises a sequence complementary to a target sequence desired to be detected and further includes a first label moiety attached. The antiprobe of the present disclosure comprises a nucleotide sequence complementary to, and typically the same length as, the probe, and a second label moiety attached. It is contemplated that the nucleotide sequence of the antiprobe will include at least one base mismatched with a base of the probe. It is further contemplated that while the probe and antiprobe sequences that are complementary are also the same length, it is within the scope of the disclosure that other nucleotide sequences may be attached to either the probe or antiprobe. These attached sequences, while extending the probe or antiprobe in length, do not themselves hybridize and interact with the probe or antiprobe, but preferably are selected to complement, for example, a region of an amplicon other than a target sequence of the probe oligonucleotide.

The systems of the disclosure will exhibit either: (i) a modulated signaling state when the probe oligonucleotide binds to the antiprobe and their interacting labeling components are brought together, or (ii) a detectably distinguishable signaling state when the probe oligonucleotide binds to a target nucleotide sequence and the labeling components are separated.

In the various embodiments of the probe:antiprobe systems of the disclosure, and in particular when the systems are used in real-time PCR analyses, the probe oligonucleotide will have a first labeling moiety at the 5' end thereof, wherein the labeling moiety can be, for example, a fluorescence donor (a fluorophore), and the opposing 3' end is blocked to prevent extension of the oligonucleotide by a 5'-3' polymerase. In these embodiments, the antiprobe can have attached at the 3' end a second labeling moiety that is a fluorescence quencher compound. Accordingly, as shown for example in FIGS. 1, 2, 5-7, in these embodiments, when the probe and the antiprobe are associated to form a duplex nucleic acid, the first labeling moiety, i.e. the fluorophore, and the second labeling moiety, i.e. the fluorescence quenching compound, are brought into close proximity, whereupon the fluorescence emission from the fluorophore is modulated, thereby reducing or eliminating any detectable fluorescence. In the event that the probe is preferentially bound to a target nucleotide sequence and not to the antiprobe, the fluorescence quencher compound and the fluorophore are spatially separated, the fluorescence emission is no longer quenched, and is, therefore, detectable, indicating the presence of the target nucleotide sequence.

Figure 7B:
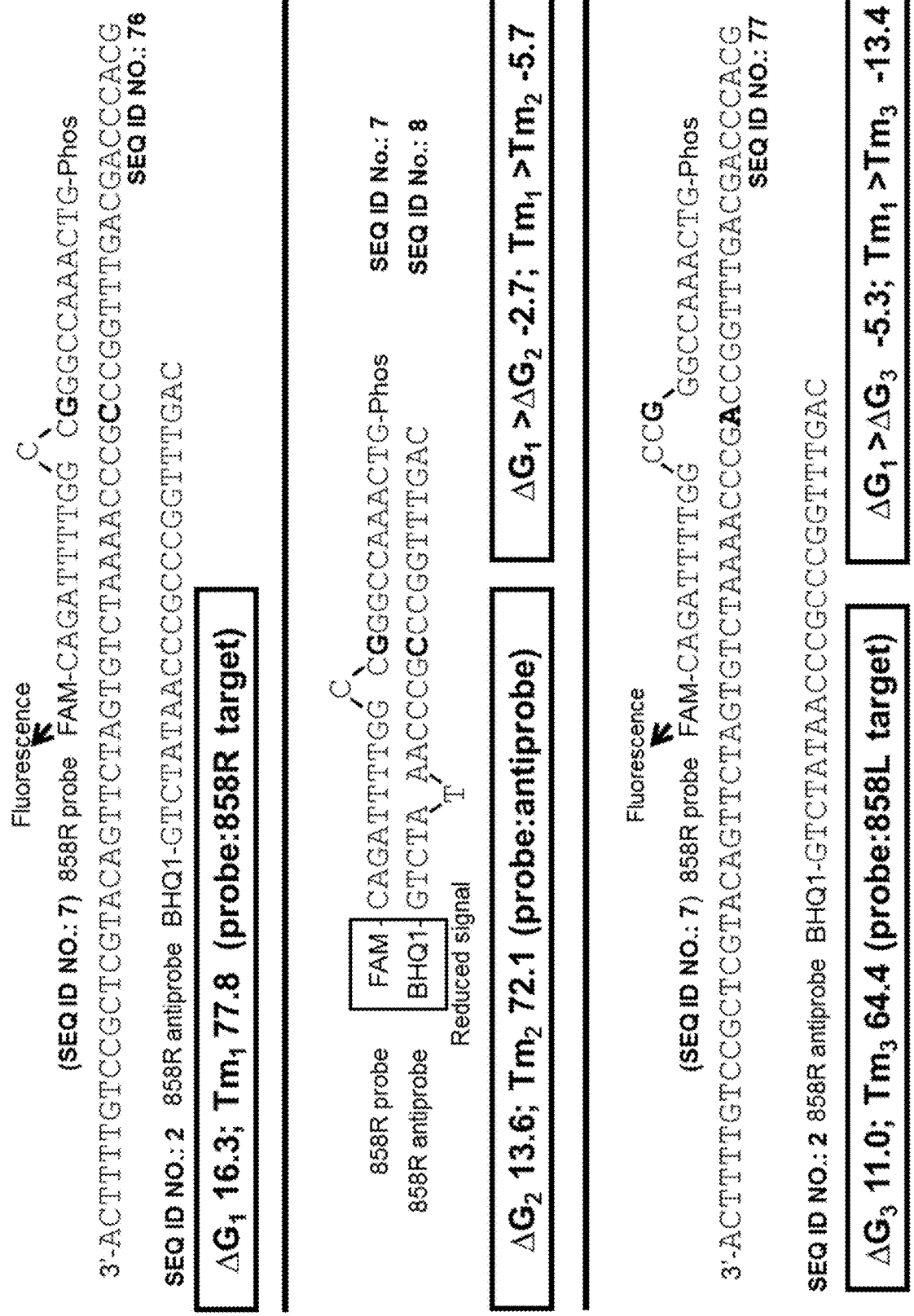
FIG. 7B illustrates the 858R probe:antiprobe components to detect the mutant variant of EGFR by qPCR wherein both the probe and the antiprobe are engineered with a mismatched base. The mismatch inserted in the antiprobe (T-T) brings down the thermal affinity of the probe:antiprobe duplex relative to the probe:mutant target duplex. The helper mismatch engineered into the probe (C-C) anticipates a wild target with the 858L SNP variant that is positioned two bases away from the helper mismatch. When the mutant probe encounters such a target, a 3 base "hybridization bubble" occurs as shown (CCG), dropping thermal affinity and preventing false target detection. With effective design, these thermodynamic interactions result in three distinct hybridization levels that differ from one another by about 5-6 degrees in Tm and about 2-2.5 kcal/mol in ΔG. Consequently, as the temperature descends during the annealing step of qPCR, the mutant probe preferentially hybridizes to the mutant target sequence if present due to the higher Tm and more negative ΔG for that duplex as shown (top). In contrast, the probe:antiprobe duplex has a significantly lower Tm and higher ΔG. However, these levels are still much higher in Tm and lower in ΔG than the mutant probe:wild target duplex (bottom) due to the SNP mismatch (G-A) and the helper mismatch (C-C) working together to create a multi-base "hybridization bubble". Calculated Tm and ΔG values are depicted in the figure for each hybridization level and for the differences between these levels, based on the Two-State Melting (Hybridization) Analysis program of the DINAMelt Web Server (run at 58 degrees) [N. R. Markham & M. Zuker. DINAMelt Web Server for Nucleic Acid Melting Prediction. *Nucleic Acids Res.* 33, W577-W581, 2005] It should be noted that the Tm levels for this system are high relative to other commonly employed Tm analysis sources (eg. Operon and IDT websites).

In the case of a matching target sequence, the probe binds more firmly to the target sequence rather than to the antiprobe sequence, triggering a detectable signal and, in the case of an incorrectly, mismatched target, the probe will bind more firmly to the antiprobe, thereby inhibiting or preventing probe:mismatched target duplex formation and detection of an mismatched target even when hybridization temperatures are suboptimal. The probe sequence may optionally comprise a helper mismatched base that is positioned about 2 bases away from a targeted variant base position desired to be detected, such that if the variant base position does not match the corresponding base in the probe oligonucleotide, a "hybridization bubble" is formed, as shown in FIG. 7B, to improve single base discrimination, and any unlabeled 3' end is optionally blocked to prevent polymerase extension.

In other embodiments of this system of the disclosure, the first labeling moiety of the probe can be the fluorescence quenching compound, and the second labeling moiety of the antiprobe can be the fluorophore. It is further contemplated that the first labeling moiety can be a first fluorophore that upon stimulation emits a fluorescence having a first wavelength. When the probe and antiprobe are in close proximity due to their hybridization to each other, the emitted fluorescence of the first labeling moiety can serve as a stimulation radiation for the second labeling moiety that is also a fluorophore (i.e. a FRET-based system). The stimulated second labeling moiety then can emit fluorescence at a longer wavelength than that of the first fluorescence. Accordingly, there is a difference between (i) the fluorescence wavelength detected when the probe and antiprobe are in association and (ii) the fluorescence wavelength of the probe label moiety that is detectable only when the probe and antiprobe oligonucleotides are dissociated, as when the probe oligonucleotide complexes with a target nucleotide sequence.

With the appropriate selection of the length and sequence of the probe:antiprobe system intended for a particular target of interest, the system includes an inherent error-checking mechanism that thermodynamically favors one of two binding and detection states. State one, which occurs when a target nucleotide sequence is present that matches the probe sequence, is where the probe preferentially binds to the complementary target sequence rather than to the antiprobe, thereby triggering positive detection. State two occurs when no target, or a target having at least one base mismatch with the probe sequence, is present, so that the probe preferentially binds to the antiprobe, thereby blocking or preventing detection of a mismatched target, even under suboptimal hybridization or PCR annealing temperatures. Examples of such probe:antiprobe systems according to the disclosure have achieved single base discrimination at qPCR annealing temperatures of between about 52° C. to about 62° C., as shown, for example in FIGS. 6-11.

Figure 6:
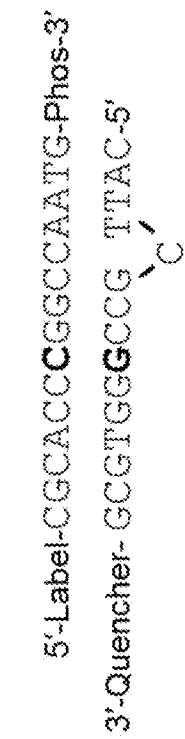
FIG. 6 illustrates an iDDS probe:antiprobe system according to the disclosure for the detection of the wild-type SNP variant of VKORC1 (Vitamin K epoxide reductase gene). As qPCR descends each cycle from denaturing at 95° C. to annealing/detection at about 52-62° C., the probe binds first to the matching target (top) due to correct matching at the SNP site (bold G) and thus higher thermodynamic affinity (measured by ΔG and Tm). If no matching target is available, the probe will then bind secondly to the antiprobe at a less negative ΔG and lower Tm (middle) due to the mismatch engineered in the antiprobe to bring the Tm down about 5-6 degrees and raise the ΔG by about 2-2.5 kcal/mol. In this case and in most cases, the thermodynamic affinity between the probe and the second target with a non-matching SNP (bold A) is significantly lower than the affinity of the probe to the antiprobe, about 5-6 degrees lower in Tm and 2-2.5 kcal/mol higher in ΔG (bottom). Thus, the probe:antiprobe system selectively detects the correct target and inhibits or prevents binding and detection of an incorrect target.
Figure 6:

It was further found that such discrimination was maintained, even when the same assays were run at much lower annealing temperatures (i.e. below 50° C.). The antiprobe binding and blocking mechanism, therefore, provides a unique multi-temperature mechanism to prevent or reduce the likelihood of obtaining false positive results. This capability occurs because the differences in competitive binding between probe, antiprobe and target sequences creates three thermodynamic binding levels: 1) a first high level based on strong complementary binding between the probe and a fully matching target; 2) a second intermediate level based on the weaker binding between probe and antiprobe that results from at least one mismatched base position engineered within the antiprobe; and 3) a third lower level based on the strongly reduced thermodynamic binding that generally occurs between the probe and an non-matching target (FIG. 6). The systems of the disclosure, therefore, comprise a probe that binds first to a fully matched target if such a target is present and that binds secondarily to the antiprobe if no correct target is present. Probe binding to an incorrect target, therefore, is effectively avoided or blocked.

When two potential target nucleotide sequences differ by two or more bases, such differences will cause a large divergence in thermodynamic binding between the probe oligonucleotide and correct (matched) target sequence versus the probe oligonucleotide and the incorrect (i.e. mismatched) target sequence. In such cases, almost any mismatch inserted in the antiprobe will result in probe to antiprobe binding that is thermodynamically intermediate between (a) probe to matched target binding and (b) probe to mismatched target binding.

However, when the goal is to discriminate a single base difference between a target and another, similar, sequence, and thermodynamic analysis indicates that the expected variants would not create a significant thermodynamic shift, it may be necessary to further modify the probe:antiprobe system by including a helper mismatch in the probe sequence, typically within two bases of the single base variant site desired to be detected so that probe binding to the non-matching target opens a multi-base "hybridization bubble" that accentuates thermodynamic differences (FIG. 7B). This modification of the probe can increase single base discrimination where the non-matching base variant of interest has limited effect on either the Tm or $\Delta G$. Sometimes the non-matching base variant will only drop the Tm about 5° C. or less, and the $\Delta G$ might also increase by only 2 kcal/mol or less. However, when a helper mismatch is introduced, the Tm can drop at least about 10° C.-15° C. and/or the $\Delta G$ can increase by at least about 4 to 5 kcal/mol, relative to the Tm and $\Delta G$ characteristics of binding between the probe and the desired target.

It has been found that single base discrimination can be expected if: (i) the antiprobe mismatch with the probe is placed where it will reduce the $T_m$ by at least about 5° C. and/or increase the $\Delta G$ by at least about 2 kcal/mol compared to probe binding to a correctly matching target, and (ii) the non-matching single base mutant or variant further reduces probe to mismatched-target binding by at least about 5° C. more in Tm, and/or increases the $\Delta G$ by at least about 2 kcal/mol or more, relative to probe to antiprobe binding. These thermodynamic parameters are generally achieved by selecting a mismatch site lying between the second base from each end and the central 2 or 3 bases of the probe oligonucleotide, and by inserting a mismatched base in a position that otherwise comprises an A, T or C, wherein an T base is typically inserted in an A site, an A base is typically inserted in a T site, or a T base is inserted in a C site (making a weak G-T mismatch). When the system according to the disclosure is used as an internal probe between flanking primers during an amplification procedure such as real-time PCR, any unmodified 3' ends of probe or antiprobe should also be blocked to prevent polymerase extension.

The present disclosure further encompasses embodiments of methods for utilizing the probe:antiprobe system for single base discrimination. One method may comprise the following steps: (a) obtaining (i) a probe oligonucleotide complementary to an intended target nucleotide sequence, and (ii) an antiprobe oligonucleotide that has the same number of nucleotide positions as the probe oligonucleotide and a sequence that is complementary to the probe except for at least one mismatched or deficient base position, and where the probe and the antiprobe each have a labeling moiety attached thereto, the labeling moieties being selected as cooperating when the probe is bound to the antiprobe to provide a modulated, i.e. negative or reduced signaling state, and when the probe is bound to a target nucleotide sequence provides a signaling state indicating probe:target duplex formation; (b) determining by thermodynamic analysis the hybridization binding forces between the probe, the antiprobe, and the target sequences; (c) measuring the binding forces between the probe sequence and the desired target sequence, the probe sequence and the antiprobe sequence, and the probe sequence and a mismatched target sequence, wherein binding forces are defined as $\Delta G$ and/or Tm; (d) determining if the probe to antiprobe binding forces are lower than the probe to matching target binding forces, wherein a difference of at least about −2 kcal/mol in $\Delta G$ levels and/or at least about 5° C. in Tm levels indicates that the probe will preferentially bind to the matching target sequence and not to the antiprobe; (e) determining if the probe to the non-matching target binding forces are lower than the probe to antiprobe binding forces, a difference of at least about −2 kcal/mol in $\Delta G$ levels and/or at least about 5° C. in Tm levels indicating that the probe will preferentially bind to the antiprobe and not to the non-matching target; (f) determining if the differences in binding forces between probe and the matching target versus the probe and the antiprobe versus the probe and the non-matching target comprise descending levels of thermodynamic binding whereby the probe will bind to a correct target, if available, and secondarily to the antiprobe, whereupon probe binding to an incorrect non-matching target would be avoided or prevented; (g) optionally modifying the antiprobe at one or more base positions to decrease or increase the binding forces between the probe and the antiprobe oligonucleotides; (h) optionally modifying the probe at one or more base positions and within about 2 base positions of a base position corresponding to a single base polymorphism of the target sequence thereby providing a "hybridization bubble" when the probe hybridizes to a region of the target sequence having an SNP variant and thereby decreasing the binding forces between the probe oligonucleotide and the mismatching target; (i) assessing the probe:antiprobe composition by testing with a target sequence having an SNP within the region complementary to the probe oligonucleotide and with a target not having the SNP; and (j) repeating steps (c)-(i), thereby obtaining a probe:antiprobe system identifying a target nucleotide sequence from a similar sequence having at least one nucleotide difference.

Embodiments of the probe:antiprobe systems of the disclosure may include probe or antiprobe oligonucleotides modified by having one or more components that can increase the specificity of the probe with its corresponding target sequence by increasing complementary binding, such as, but not limited to nucleotides other than adenosine, cytosine, guanine, and thymidine, various non-natural nucleotides, including but not limited to, LNA (locked nucleic acid) or PNA (peptide nucleic acid) or BNA (bridged nucleic acid), and or the structural modifications MGB (minor groove binder), ZNA (Zip nucleic acid) and the like.

This modification of the probe can increase single base discrimination where the non-matching base variant of interest has limited effect on either the Tm or ΔG. Sometimes the non-matching base variant will only drop the Tm about 5° C. or less, and the ΔG might also increase by only 2 kcal/mol or less. However, with the introduced mismatched base and the "hybridization bubble" the Tm can drop about 10° C. to 15° C. and/or the ΔG can increase by 4-5 kcal/mol, relative to the Tm and ΔG characteristics of binding between the probe and the desired target.

The probe:antiprobe systems of the disclosure may further include a mismatched base position in the probe or antiprobe selected from a natural non-complementary base, a universal base, an artificial base, an extra non-matching base, a missing base, an abasic site, a spacer, a linker or any structural means that can diminish the complementary binding between the probe oligonucleotide and the antiprobe oligonucleotide, or between the probe oligonucleotide and the desired target sequence.

To enhance signaling or quenching, embodiments of the probe:antiprobe systems may further include probe oligonucleotides and or antiprobe oligonucleotides that are labeled on both ends, wherein a probe can comprise a fluorescence emitter and a fluorescence modulator, and an antiprobe can comprise a fluorescence modulator and optionally a fluorescence emitter, or alternatively, a probe may comprise two fluorescence emitters and an antiprobe may comprise two fluorescence modulators. If the probe oligonucleotide comprises a 3' fluorescent emitter, that end may be optionally modified with a spacer in between the probe oligonucleotide and the 3' fluorophore.

Embodiments of the present disclosure further encompass systems that incorporate the probe:antiprobe system into real time PCR assays. These embodiments include, but are not necessarily limited to:

1. iDDS probes: For qPCR as illustrated in FIG. 1B, wherein the probe oligonucleotide is selected to be complementary to a target sequence lying between two flanking PCR primers; and wherein any unlabeled 3' end of the probe or antiprobe oligonucleotide is blocked to prevent polymerase extension therefrom. iDDS probes are especially suited for detecting a desired target nucleotide sequence in the presence of related sequences that differ from the desired sequence by a single nucleotide polymorphism (SNP).

2. The probe:antiprobe composition may also comprise labeled probe and antiprobe components that are terminally joined to comprise one molecule, wherein the antiprobe component comprises a sequence that is deficient in complementary binding to the probe component, compared to the affinity of the probe for a target nucleotide sequence.

3. ZIPR probes: For use in qPCR as illustrated in FIG. 1C, the labeled probe, herein called a "ZIPR probe", comprises a probe oligonucleotide that comprises a primer sequence and that thereby allows amplification and simultaneous detection of a targeted segment at the terminal end of a PCR amplified product rather than at an internal sequence located between the PCR primer sites, wherein the 3' end of the ZIPR probe oligonucleotide is not blocked to prevent polymerase extension. The paired antiprobe oligonucleotide also serves to diminish false target detection. Two such primer-probes can be used at the opposite ends of a target desired to be amplified, where they both can comprise the same labeling to provide double signaling. Alternatively, they can each be differently labeled to provide two color signaling.

4. FLIP probes: For use in high specificity real-time detection or end-point detection of amplified targets, as illustrated in FIG. 2A, the antiprobe component of the probe:antiprobe system can comprise a labeled segment conjugated to the 5' end of a primer oligonucleotide by an abasic connector such as a spacer. This modification of the probe:antiprobe structure alters primer kinetics so that the detected signaling exhibits linear amplification curves versus normal sigmoid amplification curves so that detection and quantitative assessment of a sample can be accurately achieved at the end-point as well as by real-time monitoring during amplification, as shown, for example, in FIG. 13A. The probe and antiprobe sequences can also be fully complementary, without a mismatch, except that the probe is made slightly longer than the antiprobe sequence, by one or more bases. The linear amplification curves produced by this probe:antiprobe composition are comparable to the linear curves produced by LATE PCR. In LATE-PCR, however, linear amplification is achieved by providing primers with unequal concentrations with one primer severely limited in amount resulting in asymmetrical amplification (Sanchez et al. (2004) 101: 1933-1938; Wangh et al. U.S. Pat. No. 7,632,642).

Figure 2B:
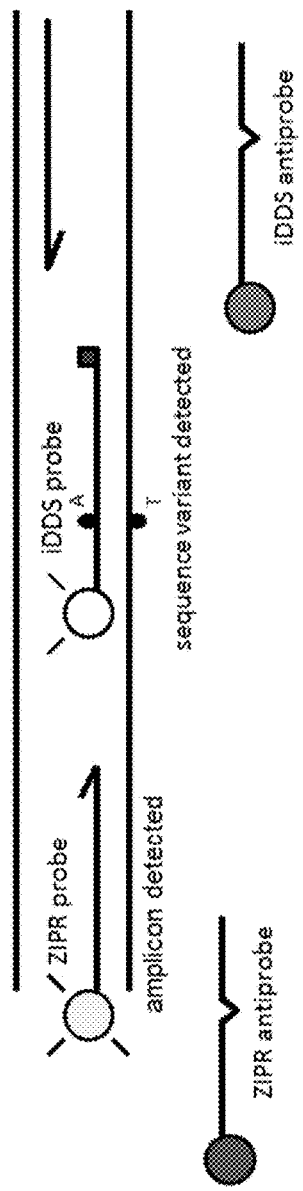
FIG. 2B schematically illustrates the ZIPR DDS:iDDS two probe system to quantify total amplicons and the proportion thereof of a particular variant.
Figure 2C:
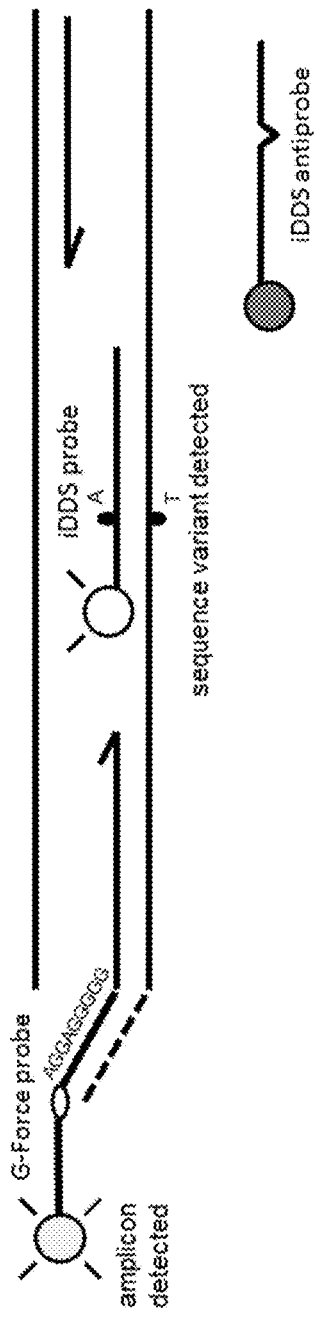
FIG. 2C schematically illustrates the G-Force DDS:iDDS two probe system to quantify total amplicons and the proportion thereof of a particular variant.
Figure 5:
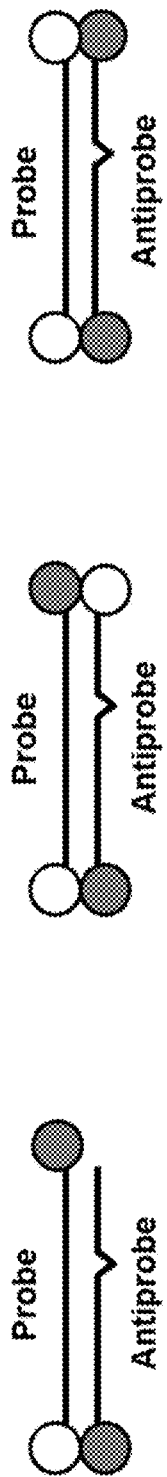
FIG. 5 illustrates alternate labeling configurations to improve signaling with DDS probe:antiprobe systems: (left) where the probe has both a fluorescence emitter and a fluorescence modulator and the antiprobe has a fluorescence modulator, (middle) where the probe has a fluorescence emitter and a fluorescence modulator and the antiprobe has a fluorescence emitter and a fluorescence modulator, and (right) where the probe has two fluorescence emitters and the antiprobe has two fluorescence modulators.

5. G-Force probes: For use in real-time PCR, as illustrated in FIG. 2C, is a primer-probe oligonucleotide, herein called "G-Force" probe, having three segments: a labeled probe segment, an antiprobe segment that can fold together with the probe segment, and a target-specific primer segment at the 3' end. The probe segment is 5' labeled with a fluorophore and includes a C-rich sequence of about 6 to about 9 bases. The antiprobe segment is G-rich and complementary to the C-rich segment and comprises about 6 to about 10 bases. When these segments fold and hybridize together due to their complementary sequences, the guanines in the antiprobe segment serve as a quencher to absorb the fluorescent emissions of the probe. The probe and antiprobe segments are joined by an abasic connector such as a spacer that facilitates the folding and binding of these segments together and that prevents copying of the probe segment when the primer-probe is incorporated into an amplicon. The abasic connector can be flanked by one or more A or T bases to facilitate folding and probe to antiprobe binding.

This G-Force probe:antiprobe system exhibits two structural and signaling states: (i) a folded structure and signaling state that occurs when the primer-probe is not associated with another hybridized nucleic acid, where the cytidine-rich segment folds over and binds to the guanine-rich segment, bringing the fluorescence-emitting label next to fluorescence-absorbing guanines, and (ii) a second structure and signaling state when the primer-probe is incorporated into an amplified target, whereupon the signaling unit is unfolded and fluorescent emissions are released. However, after the first amplification cycle, the target template is permanently extended with a sequence complementary to the guanine-rich antiprobe segment, thus facilitating probe binding and signaling in subsequent amplification cycles. Amplified targets are thereby labeled and detected quantitatively with one fluorophore per amplicon. A similar primer-probe with the same or different labeling can be used on the other end of the amplicon to provide double signaling or two-color signaling.

In one preferred embodiment of this system, the G-Force primer-probe has a 5'-3' probe:antiprobe structure comprising FAM-CCCCTCCA-spacer$_{18}$-AGGAGGGGG (SEQ ID NO: 98) plus the 3' primer. Due to the extra G on the antiprobe segment, when the C-rich probe segment binds to the G-rich antiprobe segment, the fluorophore will be in the vicinity of at least two G bases. Alternatively, the probe can have complementary sequences containing about two or more C's near the 5' end of the probe segment and about two or more G's near the 3' end of the antiprobe segment.

6. Double DDS probes: It is contemplated that two DDS probe systems according to the present disclosure can be used simultaneously to detect different parts of the same amplified target, as schematically shown in FIGS. 2B and 2C. Such a system can comprise a labeled primer-probe such as, but not limited to, a ZIPR probe, a G-Force probe, and the like, to detect and quantify amplified targets, and combined with an internal iDDS probe that is differently labeled, to detect and quantify those amplified targets that have a specific internal sequence such as a SNP variation. Alternatively, two internal iDDS probes with different labeling can be employed to detect different sequences within the same targeted nucleotide region, thereby providing instant confirmation that the targeted gene or species is present.

It is further contemplated that the embodiments of the disclosure may incorporate a plurality of probe:antiprobe systems according to the disclosure that can selectively detect a plurality of target sequences, wherein a positive signal with the first probe relative to a negative or weak signal from the second probe confirms the presence of a variant or mutant sequence comprising the first target sequence.

A suitable internal probe for use in this embodiment can comprise an iDDS probe:antiprobe system. A useful, but not limiting, primer-probe can be the G-Force primer-probe, where the primer-probe quantifies the amplified targets, and the internal probe:antiprobe composition quantifies the frequency of a specific internal target sequence. The use of both probes allows the measuring of the relative frequency of the variant sequence of interest. In real-time PCR, the primer-probe can exhibit a high curve and the internal probe will exhibit a curve with a lower angle proportionate to the mutant or variant frequency, as shown, for example, in FIGS. 16A and 16B.

A common issue in molecular diagnostics is the occurrence of diverse, closely related small mutations that all may have a similar effect on the structure and function of a gene product or on gene expression. For example, lung cancer diagnostics and treatment can be determined by the analysis of a few mutational biomarkers in the EGFR gene and or the KRAS gene. However, while some of these important disease-specific mutants can comprise one single base substitution, such as the EGFR Exon 21 mutation L858R 2573T>G, other cancer biomarkers are more variable although they are confined to a small sequence region. Clinically, knowing which specific deletion or which base substitution is not all that important since the clinical outcomes of any one of a series of such mutations are effectively the same. While sequencing can be performed to determine if any of such closely related mutations are present, sequencing is not effective when the mutant frequency is less than about 10 percent. One way to overcome this problem is to employ two probes directed to the same template, one detecting the wild sequence if present and the other being non-specific and detecting any wild or mutant sequence, whereupon the differences in signaling can indicate the presence of a mutant variant without specifying which mutant variant is present. This two probe strategy can be applied with an iDDS probe or a primer probe specific to the wild type, and a non-specific primer-probe detecting any variants in the same target region.

7. iDDS and Terminator probes: Another aspect of the disclosure is that the probe:antiprobe system may be suitably adapted for a two probe target enhancement system suitable for real-time PCR or other amplification-detection methods to selectively amplify and detect a first target nucleotide sequence that differs by one or more bases from a closely related second target nucleotide sequence. In general, the first target sequence is a mutant variant of interest and the second target sequence can be the wild type ("normal") sequence. This two probe system includes a first labeled internal probe:antiprobe system such as an iDDS probe, and a second unlabeled internal "Terminator" probe (termed "Wild Terminator" if specific for a wild-type nucleotide sequence variant) that has a PCR polymerase blocking function, as shown in FIGS. 3A and 3B.

The first probe includes a first target sequence, or the complement thereof, and has at least one base position that only matches the first target sequence, but not the second target sequence. The terminator probe comprises the second target sequence, or the complement thereof, and includes at least one base position found in the second target sequence but not in the first target sequence. The terminator probe is further modified at the 5' end to inhibit or prevent 5' nuclease digestion thereof, and modified at the 3' end to inhibit or prevent 3' polymerase extension therefrom.

The length and/or position of the terminator probe can be selected such that the affinity of the Terminator probe and the second target sequence is substantially greater than the affinity of the first probe and the first target sequence. Preferably, the affinity of the first probe and the terminator probe for the second target nucleotide sequence can differ by at least about 6° C. in Tm and/or at least about −4 or more kcal/mol in ΔG. In addition, the terminator probe may optionally be modified to further enhance binding to its matching target sequence by using one or more artificial nucleotides such as an LNA, a chemical modification such as ZNA or MGB, or a combination thereof.

As a consequence of the thermodynamic differences between the two probes, the Terminator probe will bind more strongly to the second target sequence, and it will inhibit or prevent the amplification of the second target sequence. It will also inhibit or prevent the binding of the first probe to the second target sequence. Therefore, this system will selectively amplify and or detect the first target sequence, thereby providing a target enhancement system useful for detecting rare or low frequency mutants or variants such as in cancer diagnostics, drug resistance or pre-natal genetic screening.

The terminator probe can be modified at the 5' end by the attachment of a molecule such as biotin, ZNA, MGB, BHQ, and the like, incorporation of 2'-O-Methyl RNA bases, attachment of a stretch of randomly selected non-complementary bases. The Terminator probe may be modified at the 3' end by the attachment of a blocking molecule (e.g. a phosphate, a spacer, an amino group, and the like), or a string of randomly selected non-complementary bases.

Accordingly, the two probe target enhancement system of the disclosure may be used in a method to selectively amplify and detect a first target sequence that differs by one or more bases from a second target sequence, even if the amount of the second target sequence is significantly greater than that of the first target sequence. Embodiments of this method, therefore, can comprise the following steps: (a) obtaining a detection probe:antiprobe system, an unlabeled Terminator probe, and a pair of flanking primers; wherein: the detection probe:antiprobe system comprises a labeled probe:antiprobe system where the labeled probe includes a first target nucleotide sequence or the complement thereof; the Terminator probe characterized as: (i) including the second target nucleotide sequence or the complement thereof, wherein the binding affinity of the Terminator probe for the second target sequence is greater than the binding affinity of the labeled probe for the first target sequence, (ii) having a 5' end modified to inhibit or prevent 5' nuclease digestion, (iii) having a 3' end modified to inhibit or prevent 3' polymerase extension, and (iv) having a length greater than that of the labeled probe, and optionally includes internal or terminal modifications to enhance binding such as an LNA or BNA, a ZNA, or a MGB; (b) obtaining a biological sample suspected of comprising the first or second target sequence, or a mixture thereof; (c) pre-amplifying the first target sequence while blocking amplification of the second target sequence with the Terminator probe; wherein this step optionally comprises between about 30 to about 75 cycles of PCR with low temperature annealing at about 48° C. to about 57° C. and wherein each denaturing, annealing or extension step is limited to about 5 seconds or less; (d) combining an aliquot, or a dilute aliquot of the pre-amplified sample, with the pair of flanking primers, and the probe: antiprobe system, said aliquot being about 5 percent or less of the amplification reaction, and a dilute aliquot is a dilution of the aliquot of at least 1:100 and typically in the range of about 1:300 to about 1:1000; and (e) amplifying and detecting the presence of the first target sequence by real-time PCR or other means.

The two probe target enhancement system of the disclosure provides real-time PCR analysis of samples suspected of containing a low frequency of a first target sequence, typically, but not limited to, the mutant sequence of interest, mixed with a relatively high frequency of the second target sequence, such as, but not limited to, a wild-type sequence. Since both target templates are amplified by the same primers, the PCR reaction components, primers, enzymes, etc., will be exhausted for the more abundant template, to the extent that amplification and detection of the first target sequence will be inhibited or prevented. It has been found, for example, that low frequency mutants in the range of about 2 percent to about 0.002 percent of mutant content were effectively detected. In addition, it is contemplated that this method will be useful in screening for low frequency mutants or variants in blood or other tissues remote from the source.

The method may be further modified by providing another probe:antiprobe composition specific to the second target sequence in step (e) above to confirm the inhibition or blocking of the second target sequence. This modified method can produce two amplification curves: a first curve that indicates the enhanced presence of the first target sequence which is typically positive indicating the mutant of interest, and a second curve that indicates the diminished presence of the second target sequence which is typically negative indicating the wild or normal sequence of interest.

8. DDS primer-probes and Terminator probes: The two probe target enhancement system of the disclosure can be further modified by replacing one PCR primer with a primer-probe composition that can non-specifically amplify and detect at least part of the sequence region targeted by the Terminator probe. To achieve this end, the primer-probe comprises a primer sequence that precedes all or part of the target region of the Terminator probe. Since the primer-probe can amplify any wild or mutant sequences within that region, including base substitutions, deletions or insertions, and if the wild sequence has been specifically blocked by the Terminator probe, then a positive signal with the primer-probe indicates that a mutant sequence is present in that target region. Therefore, one assay system can detect multiple sequence variants of interest, and multiple sequence-specific assays are not required. With this system, the primer-probe can be the ZIPR probe, the G-Force probe, the Half-Universal probe, the Universal probe, a SUNRISE® probe or any other primer-probe suitable for real-time PCR detection. This system can be used with a two-step or a one-step procedure, as shown in FIGS. 3A and 3B.

To confirm non-specific mutant detection, a second probe: antiprobe composition can be used that comprises the second target sequence or its complement. With this modification, a negative or diminished signal with the second probe: antiprobe and a positive signal with the primer-probe can confirm the presence of a variant or mutant sequence in the sample.

Any of the probes of the probe:antiprobe systems of the disclosure can be anchored to a substrate, preferably by a covalent linker, using methods well-known in the art, and the antiprobe is applied in solution along with the unlabeled targets. Single base discrimination can be achieved with multiple targets when using one common hybridization temperature, even though each probe may have been optimized for somewhat different hybridization temperatures. This temperature tolerant feature enables easier design and more reliable performance when detecting multiple high specificity targets such as SNPs or single base mutants.

9. DDS probes and Isothermal Amplification Method (ISAM): The present disclosure further provides an isothermal amplification method (ISAM) incorporating the probe: antiprobe system disclosed herein to exponentially amplify a DNA or RNA target and to detect the products in real-time or at the end-point, the method comprising the steps: (a) obtaining a sample containing an RNA or DNA target sequence; (b) adding to said sample (i) a pair of primer oligonucleotides that can amplify a target sequence isothermally, wherein either one primer or both primers includes a RNA polymerase promoter sequence, (ii) a primer-probe oligonucleotide that comprises a first primer sequence, and a matching antiprobe or, optionally a two segment primer-probe including a RNA polymerase promoter sequence and the first primer sequence, and an antiprobe complementary to the RNA polymerase promoter sequence, (iii) a modified primer comprising an RNA polymerase promoter sequence and a second primer sequence or, optionally, a two segment primer-probe comprising an RNA polymerase promoter sequence and a second primer sequence, and an antiprobe complementary to the RNA polymerase promoter sequence, and (iv) a reaction mix comprising a reaction buffer, a RNA polymerase promoter, a reverse transcriptase, and RNase H; (c) amplifying the target sequence under isothermal or near isothermal conditions, said conditions comprising a single temperature in the range of about 35° C. to about 50° C., optionally in the range of about 40° C. to about 42° C., or comprising two alternating temperatures, each of said temperatures in the range of about 35° C. to about 50° C., optionally alternating between about 40° C. and about 45° C.; and (d) determining the fluorescent signaling periodically during amplification or at a defined end-point to determine the presence and frequency of the amplified target sequence.

Figure 18:
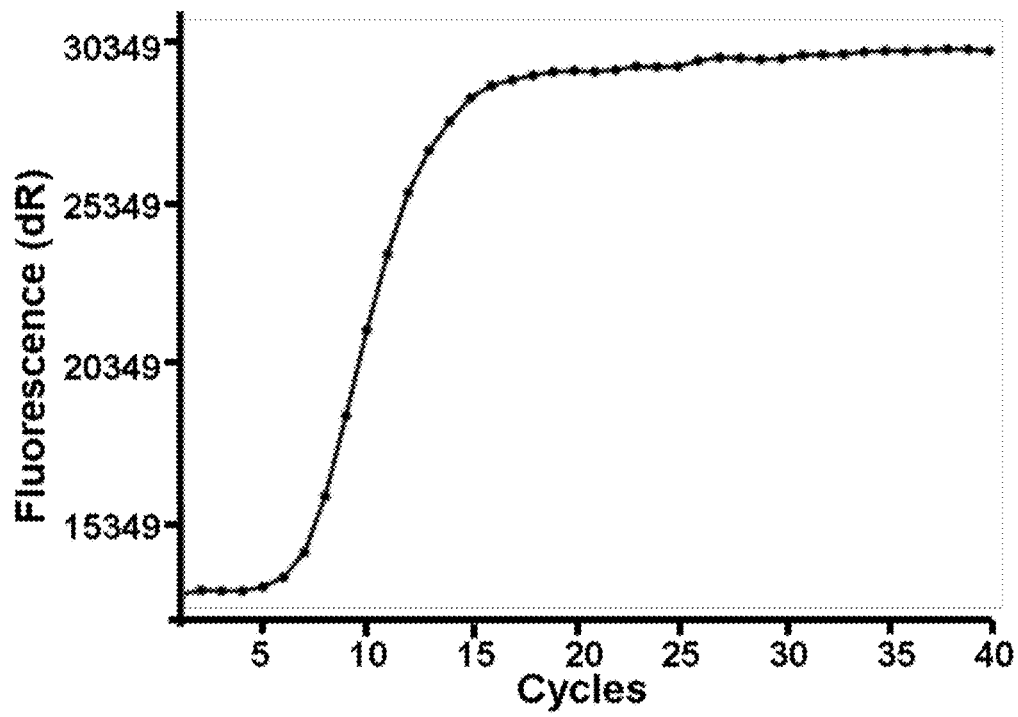
FIG. 18 is a graph showing the fluorescent signal generated by ZIPR and ISAM.

With the above probe:antiprobe compositions and amplification method, an RNA target sequence can be amplified directly to generate an amplified DNA product that is appended with an RNA polymerase promoter sequence on one or both ends and a fluorescent donor label on one or both ends. A DNA target product can be similarly amplified, modified and labeled. With this method, maximal exponential amplification can occur quickly in about 20 to 30 minutes, a rate that is faster than typical PCR or real-time PCR methods where each step is rate limited by the cycling conditions used (FIGS. 4A, 18). Although ISAM amplification can be difficult to achieve with some sequence conditions, ISAM target amplification is more robust (producing 20 to 50% more product) when both primers are appended with an RNA polymerase promoter sequence.

In another embodiment of this method of the disclosure, the probe:antiprobe components can be directed to an internal sequence between the primer sites. In this embodiment, the probe can comprise the first labeling component of a fluorescent donor-acceptor pair and a sequence internal to the primer sequences. The antiprobe can comprise the second labeling component of the fluorescent donor-acceptor pair, and a sequence that is partially deficient in complementary binding to the probe. (FIGS. 4B, 19) The antiprobe can further comprise multiple base positions that are mismatched or lacking in complementary binding to the probe. This structurally modified antiprobe sequence is required for the low temperature isothermal amplification conditions.

In another embodiment of the above probe:antiprobe compositions, coupled with the ISAM isothermal amplification method, the 5' end of a primer or primer-probe can be anchored to an array substrate, optimally by a covalent linker, and the RNA or DNA targets are isothermally amplified while attached to the chip substrate. (FIGS. 4C, 20) With this method multiple targets can be detected as they amplify in real-time or at the end-point and no wash step is required to remove unbound labeled probes.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Cycling Conditions

Real-time PCR was conducted with a Mx4000 instrument (Stratagene, Inc) using HOTSTART-IT PROBE® qPCR master mix (USB, Inc.) (2×) supplemented with 1 ml of 25 mM MgCl$_2$ in a 20 ml reaction. To initiate hot start conditions, the tube was heated to 95° C. for 5 mins followed by 40 cycles of two-step PCR (denaturation at 95° C. for 15 sec, annealing/extension at 58° C. for 1 min). The templates used were ULTRAMER® oligonucleotides (Integrated DNA Technologies, Iowa, USA) comprising the targeted EGFR gene segment with or without the T>G transversion.

Example 2

Internal DDS (iDDS) Probe:Antiprobe Compositions to Detect VKORC1 SNP Variants

An important SNP variant related to warfarin dosing is located in the VKORC1 gene encoding vitamin K epoxide reductase, subunit 1, at the site −1639 thereof, comprising a G>A change in the mutant versus the wild type. To detect these two SNP variants by real-time PCR, the probes, antiprobes and primers below were used at the following final concentrations:

```
VK-1639G-Probe:
                                        (SEQ ID NO.: 1)
5'-FAM-CGCACCCGGCCAATG-Phos-3'
at 200 nM;

VK-1639G-Antiprobe:
                                        (SEQ ID NO.: 2)
5'-CATCGGCCGGGTGCG-BHQ1-3'
at 400 nM;

VK-1639A-Probe:
                                        (SEQ ID NO.: 3)
5'-FAM-ATTGGCCAGGTGCG-Phos-3'
at 200 nM;

VK-1639A-Antiprobe:
                                        (SEQ ID NO.: 4)
5'-CGCACCTGGCCTAT-BHQ1-3'
at 400 nM;

VK-Forward primer:
                                        (SEQ ID NO.: 5)
5'-CCTCTGGGAAGTCAAGCAAG-3'
at 200 nM;
and VK-Reverse primer:
                                        (SEQ ID NO.: 6)
5'-AAATGCTAGGATTATAGGCGTGA-3'
at 200 nM
```

While the probes and antiprobes contain the targeted single base variants for VKORC1, each antiprobe was modified with a mismatched base (wild antiprobe position 4, mutant antiprobe position 12) to reduce the binding of the probe to the antiprobe relative to the binding of the probe to a correctly matching target. The intended mismatch in probe:antiprobe structure was to achieve an affinity between probe and antiprobe that is intermediate between the affinity between the probe and the correct target vs. the probe and an incorrect target.

FIG. 6 shows how the sequence of the wild probe interacts: (1) with the intended wild target sequence, (2) with the selected antiprobe sequence, and (3) with an incorrect target sequence (in this case the mutant sequence) to create three different levels of thermodynamic affinity as measured by Tm and ΔG. These probes, antiprobes and targets are then subjected to real-time PCR cycling and detection wherein the temperature repeatedly descends from denaturing at 95 degrees to an annealing temperature of about 58° C., and then back to 95° C. (with or without an extension step at about 72° C.).

Fluorescent signaling was assessed at each annealing step. Probe to correct target binding occurs first at about 5° C. above the annealing temperature, and then, probe to antiprobe binding occurs second at about the annealing temperature. Correct target binding turns on signaling while antiprobe binding turns off signaling. Thermodynamically, probe to incorrect target binding can only occur last, or not at all, since it can only occur effectively at about 5° C. lower than the temperature at which probe to antiprobe binding is occurring. Moreover, since a two to one excess of antiprobes is provided, probe to incorrect target binding is effectively blocked. Typically, primer binding is also optimized for the PCR annealing temperature. Because of these structural and thermodynamic features of iDDS probe:antiprobe based assays, there is little or no opportunity for a probe to bind to an incorrect target that differs by a single base from the intended target.

Cycling conditions: Real-time PCR was conducted with a Mx4000 instrument (Stratagene, Inc) using HOTSTART-IT PROBE® qPCR master mix (USB, Inc.) (2×) supplemented with 1 ml of 25 mM MgCl$_2$ in a 20 ml reaction. To initiate hot start conditions, the tube was heated to 95° C. for 5 min. Then followed 40 cycles of two-step PCR (denaturation at 95° C. 15 sec, annealing/extension at 58° C. for 1 min). The templates used were Ultramers synthesized by IDT comprising the targeted gene segment, with or without the mutant base, and the flanking primer sites.

Figure 8A:
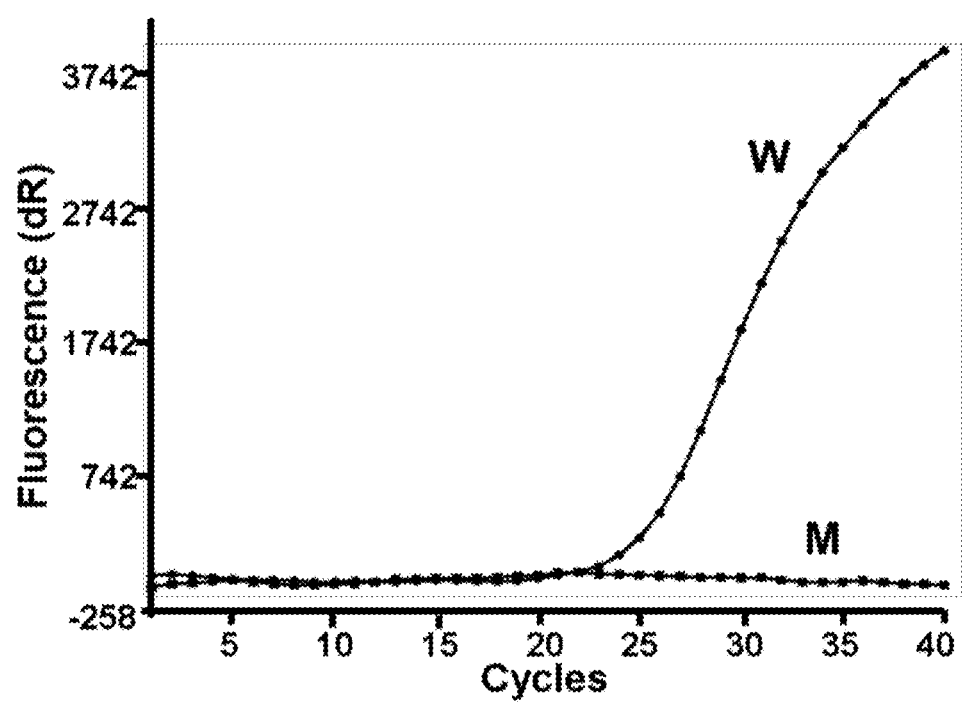
FIG. 8A is a graph showing the fluorescent signal generated by qPCR by using iDDS with a probe oligonucleotide specific for the wild-type SNP variant of VKORC1 with wild-type (W) and mutant variant (M) target nucleotide sequences.
Figure 8B:
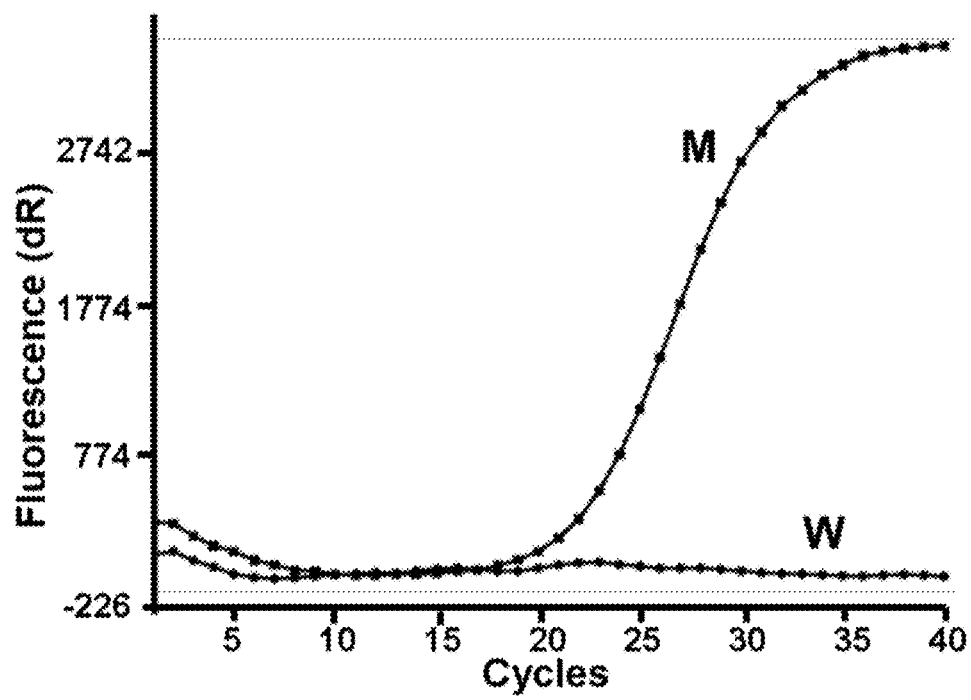
FIG. 8B is a graph showing the fluorescent signal generated by qPCR by using iDDS with a probe oligonucleotide specific for the mutant SNP variant of VKORC1 with wild-type (W) and mutant variant (M) target nucleotide sequences.

FIGS. 8A and 8B show the amplification curves from four tubes that contained 1,000 copies of the wild or mutant template and that used either the wild or mutant probe. The positive (upward) curves reflect either detection of the mutant template with the mutant probe (FIG. 8B), or detection of the wild template with the wild probe (FIG. 8A). The flat curves reflect the wild probe with the mutant template or the mutant probe with the wild template. Similar wild and mutant iDDS probe:antiprobe sets for two related diagnostic SNPs, CYP2C9*2 and CYP2C9*3, were also fabricated and they performed with similar results.

CY2-W-probe:
(SEQ ID NO.: 64)
FAM-CATTGAGGACCGTGTTCAAGA-Phos at 200 nM;

CY2-W-antiprobe:
(SEQ ID NO.: 65)
TCTTGAACACGGTCCTCTATG-BHQ1 at 400 nM;

CY2-M-probe:
(SEQ ID NO.: 66)
FAM-CTCTTGAACACAGACCTCAATGC-Phos at 200 nM;

CY2M-antiprobe:
(SEQ ID NO.: 67)
GCATTGAGGACTGTGTTCATGAG-BHQ1 at 400 nM;

CY2Fprimer:
(SEQ ID NO.: 68)
AATTTTGGGATGGGGAAGAG at 200 nM;

CY2R-primer:
(SEQ ID NO.: 69)
GTTTTTCTCAACTCCTCCACAAGG at 200 nM;

CY3W-probe:
(SEQ ID NO.: 70)
FAM-GAGAAGGTCAATGAATCTCTGGAC-Phos at 200 nM;

CY3W-antiprobe:
(SEQ ID NO.: 71)
GTCCTGAGATACATTGACCTTCTC-BHQ1 at 400 nM;

CY3M-probe:
(SEQ ID NO.: 72)
FAM-AGAAGGTCAAGGAATCTCTGGAC-Phos at 200 nM;

CY3M-antiprobe:
(SEQ ID NO.: 73)
GTCCTGAGATACCTTGACCTTCT-BHQ1 at 400 nM;

CY3F-primer:
(SEQ ID NO.: 74)
CCACATGCCCTACACAGATG at 200 nM;
and

CY3R-primer:
(SEQ ID NO.: 75)
CCTTGGGAATGAGATAGTTTCTGAA at 200 nM.

Example 3

Internal DDS (iDDS) Probes for Real Time PCR Detection of a Single Base Variant of the EGFR Gene (at Exon 21 L858R) Associated with Lung Cancer Diagnosis and Therapy To detect the EGFR Exon 21 mutant codon L858R suspected of being present in a nucleic acid sample, and possibly in the presence of the 858L wild-type (normal) codon sequence, the following oligonucleotide probes, antiprobes and PCR primers were synthesized and used at the indicated final concentrations:

EGFR 858R probe:
(SEQ ID NO.: 7)
FAM-CAGATTTTGGCCGGGCCAAACTG-Phos at 200 nM;

EGFR 858R antiprobe:
(SEQ ID NO.: 8)
CAGTTTGGCCCGCCCAATATCTG-BHQ1 at 400 nM;

EGFR 858L probe:
(SEQ ID NO. 9)
CalRed610-CAGATTTTGGGCTGACCAAACTG-Phos at 200 nM;

EGFR 858L antiprobe:
(SEQ ID NO.: 10)
CAGTTTGGCCAGCCCATAATCTG-BHQ2 at 400 nM;

Forward primer:
(SEQ ID NO.: 11)
GAAAACACCGCAGCATGTC at 200 nM;
and

Reverse primer:
(SEQ ID NO.: 12)
CTGCATGGTATTCTTTCTCTTCC at 200 nM.

While the above probes and antiprobes contain the targeted single base variants at codon 858, each antiprobe also includes an additional mismatched base relative to the corresponding probe sequences at mutant 858R antiprobe position 18 (from the 5' terminus) and at the wild 858L antiprobe position 18 (from the 5' terminus) that reduces the binding affinities of the antiprobes to their matching probes (shown in FIG. 7B).

For these particular targets, the thermodynamic difference between (i) the binding of the probe and the correct target and (ii) the probe and the incorrect target was low. The probes, therefore, were each designed to include an additional helper mismatch located two bases away from the variant base site desired to be detected (at variant 858R probe position 11, and at wild 858L probe position 15, respectively). In the event of hybridization of a probe to an incorrect target, a three-base "hybridization bubble" is formed (CCG), preventing formation of the duplex and favoring hybridization to the correct target sequence or to its corresponding antiprobe oligonucleotide.

Figure 9:
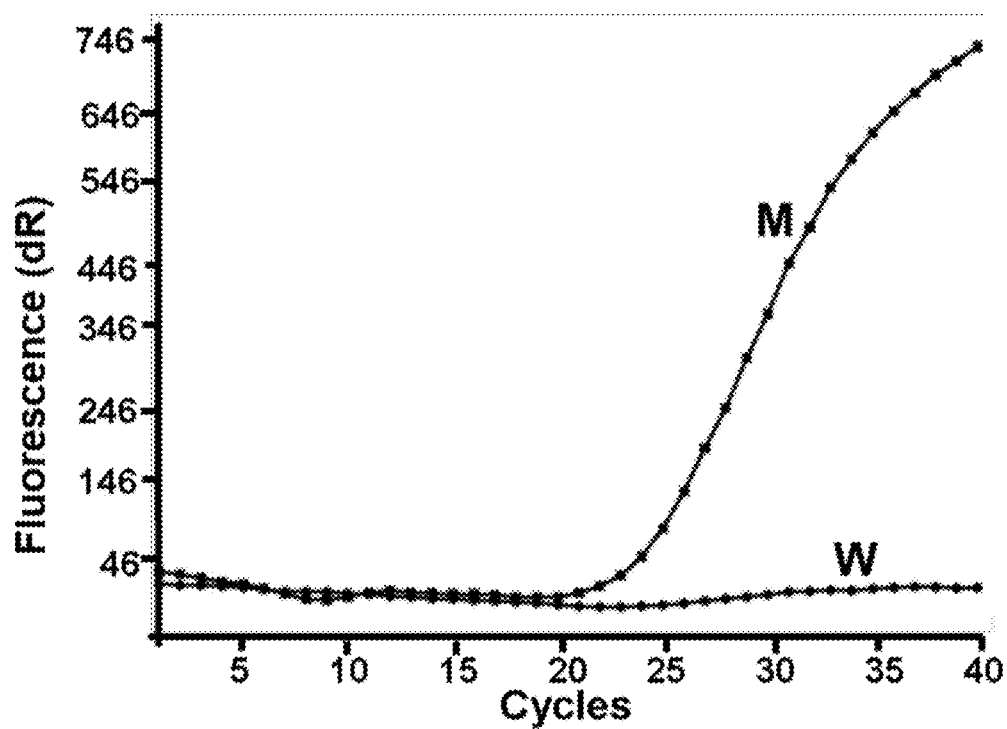
FIG. 9 is a graph showing the fluorescent signal generated by qPCR by using iDDS with a probe oligonucleotide specific for the mutant 858R SNP variant of EGFR with wild-type (W) and mutant variant (M) target nucleotide sequences.

FIG. 9 shows amplification curves from two tubes that contain 1,000 copies of the mutant template. The positive (upward) curve reflected detection of the single base mutant with the 858R variant probe. The flat curve reflected using the wild probe, which does not detect the mutant template.

Example 4

Real Time PCR Using iDDS Probes for the Detection of Pathogenic O157:H7 *E. coli* Based on Detecting the uidA +93 and Comparison with a TaqMan-MGB Probe The probe, antiprobe, and primers were fabricated with the following sequences and labeling, and were used at the indicated final concentrations:

```
Mutant O157 uidA probe:
                                    (SEQ ID NO.: 13)
FAM-CACCAACGCTGCTCAATTC-Phos at 200 nM;

Mutant antiprobe:
                                    (SEQ ID NO.: 14)
GAA TTGAGCTGCGTTGGTG-BHQ1 at 400 nM;

uidA-Forward primer:
                                    (SEQ ID NO.: 15)
CAGTCTGGATCGCGAAAACTG at 200 nM;
and udiA-Reverse primer:
                                    (SEQ ID NO.: 16)
ACCAGACGTTGCCCACATAATT at 200 nM.
```

Cycling conditions: Real-time PCR was conducted as described in Example 1 except that qPCR was run for 60 cycles and the annealing/extension step was at 60° C. for 1 min.

Figure 10A:
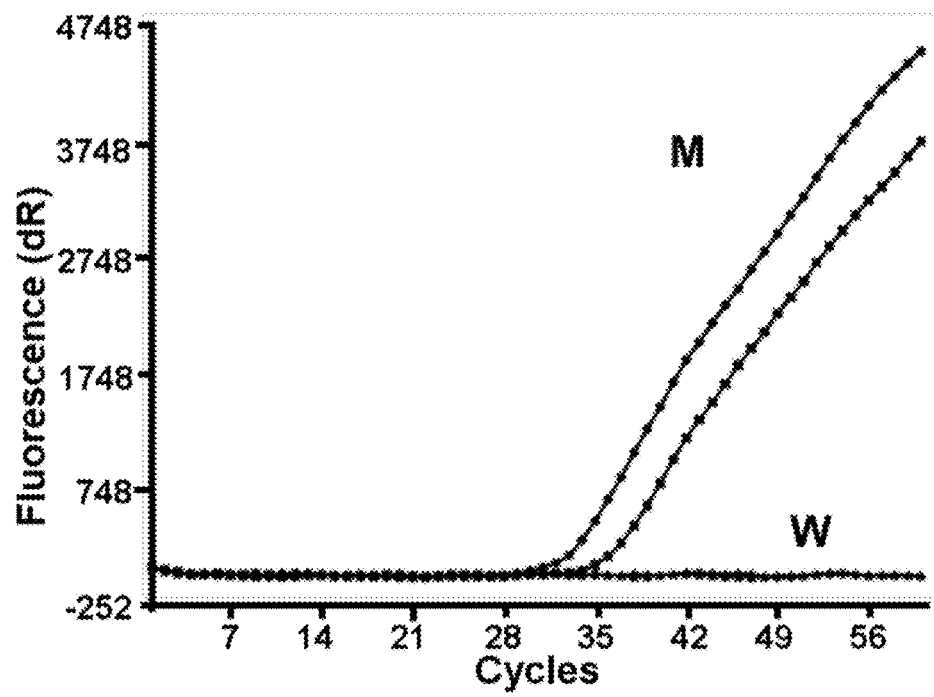
FIG. 10A is a graph showing the fluorescent signal generated by qPCR by using iDDS with a probe oligonucleotide specific for the mutant SNP of *E. coli* O157:H7 with wild-type (W) and (two concentrations) mutant variant (M) target nucleotide sequences.
Figure 10B:
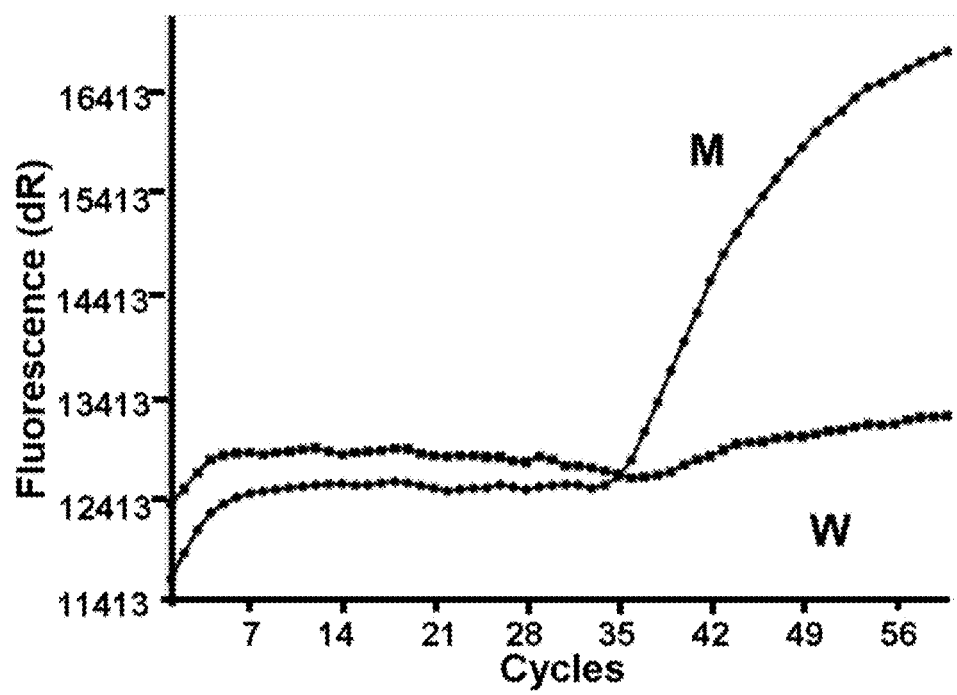
FIG. 10B is a graph showing the fluorescent signal generated by qPCR by using TaqManMGB with a probe oligonucleotide specific for the mutant SNP of *E. coli* O157:H7 with wild-type (W) and mutant variant (M) target nucleotide sequences.

FIG. 10A shows raw amplification curves from four tubes using the O157 mutant probe to detect two concentrations (50 copies and 5 copies) of the *E. coli* mutant template (positive curves) versus 50 and 5 copies of the *E. coli* negative template (flat curves). No false positive detection is seen with the wild template for 60 cycles. In comparison, FIG. 10B shows amplification curves from two tubes using a commercially available Taqman-MGB probe specific for the O157 mutant to detect 50 copies of the mutant template (positive (upward) curve) versus 50 copies of the control template (predominantly flat curve). The control template, not having the pathogen-associated polymorphism, yielded a number of false positive results (curve angling up) with the Taqman-MGB probe at 38 cycles.

Example 5

Real Time PCR Using iDDS Probes for the Detection of Gram Negative (GN) Vs. Gram Positive (GP) Bacteria The probe, antiprobe, and primers were fabricated with the following sequences and labeling, and were used at the indicated final concentrations:

```
GP probe:
                                    (SEQ ID NO.: 17)
FAM-AAGGGGCTTGATGATTTGACGT-Phos at 200 nM;

GP antiprobe:
                                    (SEQ ID NO.: 18)
ACGTCAAATCTTCATGCCCCTT-BHQ1 at 400 nM;

GN probe:
                                    (SEQ ID NO.: 19)
CalRed610-AAGGGCCATGATGACTTGA-Phos at 200 nM;

GN antiprobe:
                                    (SEQ ID NO.: 20)
TCAAGTCTTCATGGCCCTT-BHQ2 at 400 nM;

Forward primer:
                                    (SEQ ID NO.: 21)
TCCCGCAACGAGCGCAAC at 200 nM;
and Reverse primer:
                                    (SEQ ID NO.: 22)
CAGCCATTGTAGCACGTGTGT at 200 nM.
```

Cycling conditions: Real-time PCR was conducted as described in Example 1 with the annealing/extension step at 58° C. for 1 min. Both probes were used together in the same tube and each tube contained a different template.

Figure 11A:
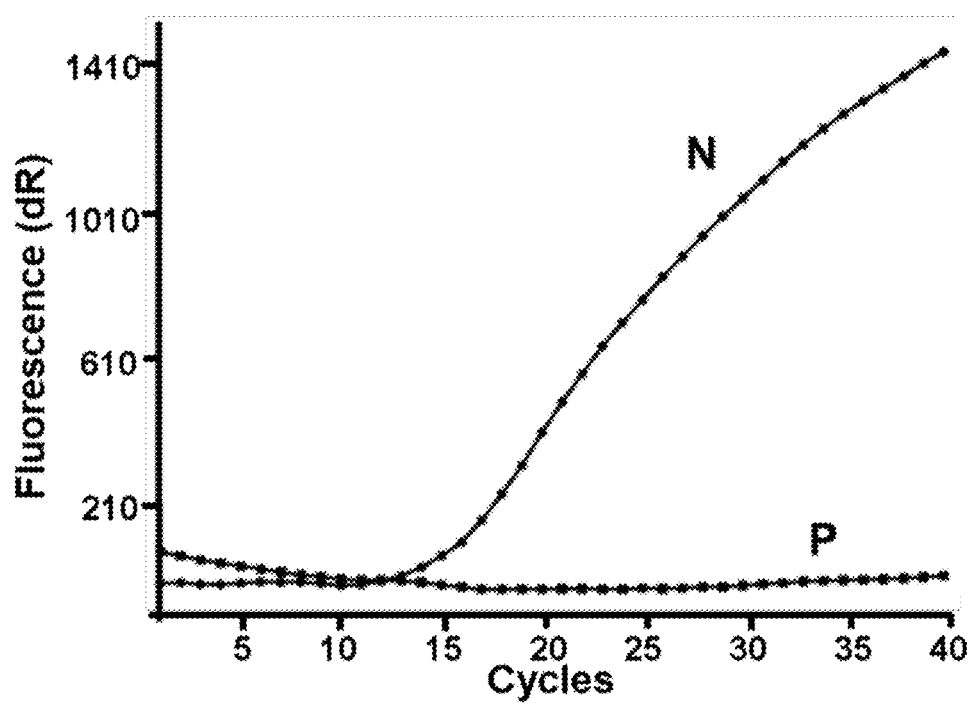
FIG. 11A is a graph showing the fluorescent signal generated by qPCR by using iDDS oligonucleotides specific for a gram positive (P) and gram negative (N) bacteria with a gram positive target nucleotide sequence.
Figure 11B:
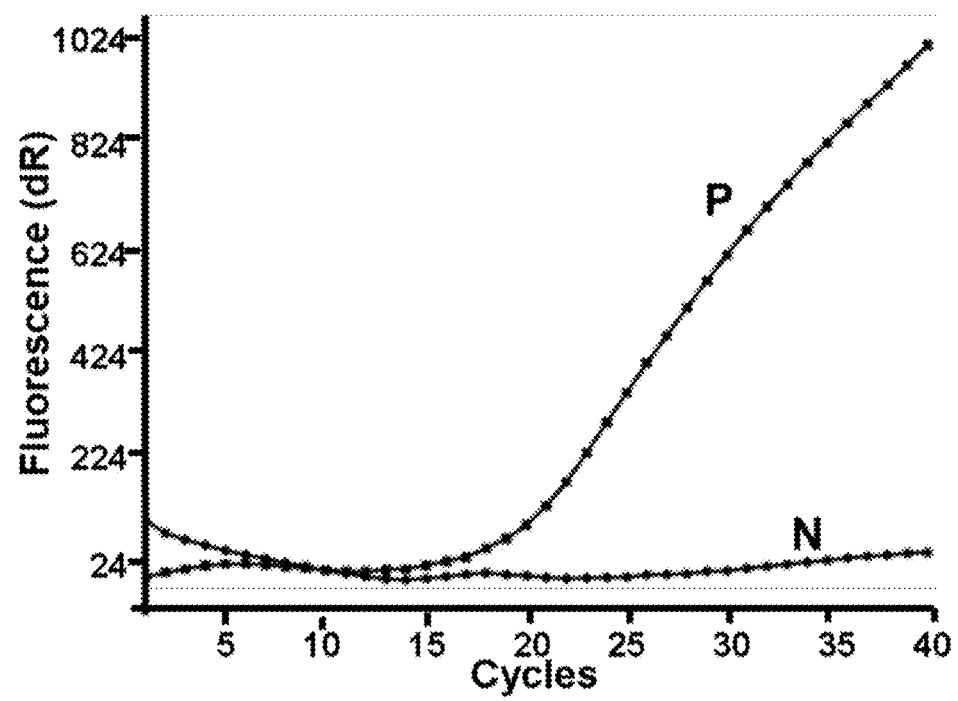
FIG. 11B is a graph showing the fluorescent signal generated by qPCR by using iDDS oligonucleotides specific for a gram positive (P) and gram negative (N) bacteria with a gram negative target nucleotide sequence.

FIG. 11A shows two curves in one tube with both the gram positive and the gram negative probe. The positive (upward) curve indicates the gram positive probe detecting gram positive templates from about $1.3\times10^4$ cells, and the flat curve reflects that the gram negative probe shows no false positive detection with the same template. Alternatively, FIG. 11B shows two curves in one tube wherein the positive curve reflects the gram negative-specific probe detecting the gram negative template from about $2.6\times10^5$ cells. The flat curve reflects the gram positive probe showing no false positive detection with those same templates.

In additional experiments, the Gram Negative probe (SEQ ID NO.: 19) was modified with FAM fluorescent labeling at the 5' end and with BHQ1 quencher labeling at the 3' end, and the Gram Negative antiprobe (SEQ ID NO.: 20) was labeled with BHQ1 at the 3' end, and optionally with FAM at the 5' end. Both modifications improved detection by qPCR, producing higher levels of exponential fluorescent signaling and lower background levels.

Example 6

Real Time PCR Using ZIPR DDS Probes for the Detection of H3N2 Influenza

The ZIPR H3N2 probe was targeted to a site in the hemagglutinin (HA) segment of H3N2 influenza genomes and was FAM labeled. The probe comprised a target-specific primer sequence. The antiprobe is BHQ1-labeled and is largely complementary to the probe. The primer was used in conjunction with the probe and antiprobe to amplify and detect H3N2 samples, and they were used at the following final concentrations:

```
ZIPR H3 Probe:
                                    (SEQ ID NO.: 23)
FAM-CTGGTTCAGAGTTCCTCAACA at 200 nM;

ZIPR H3 antiprobe:
                                    (SEQ ID NO.: 24)
TGTTGATGAACTCTGAACCAG-BHQ1 at 400 nM;
and H3 primer:
                                    (SEQ ID NO.: 25)
CCATCAAGGATCTGATGAGGA at 200 nM.
```

Cycling conditions: Real-time PCR was conducted as described in Example 1.

Figure 12:
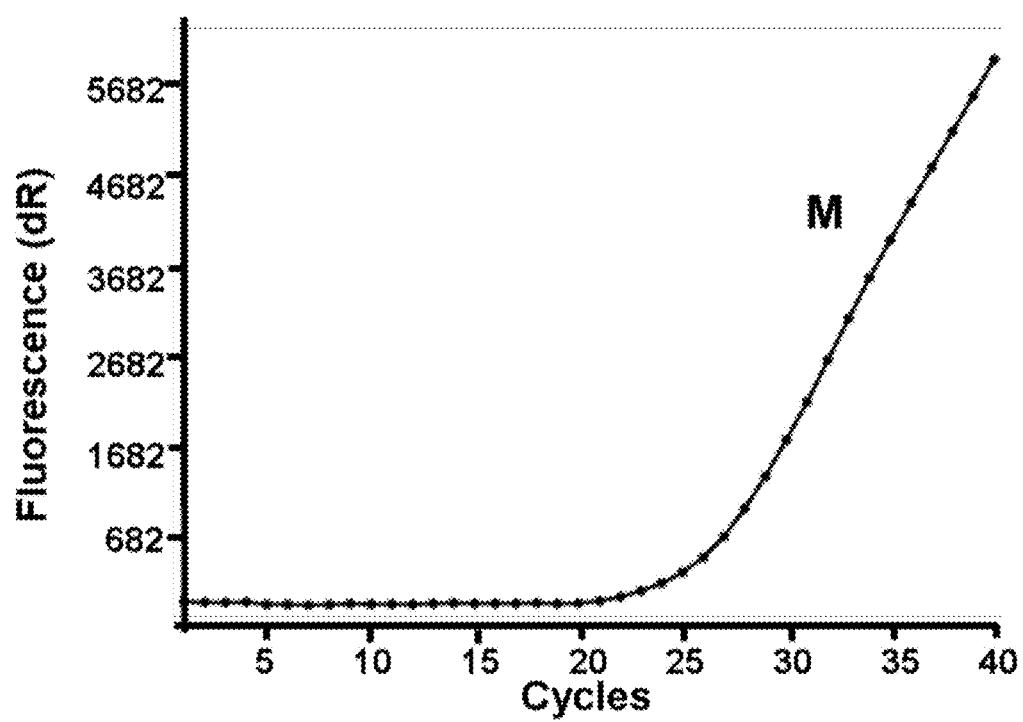
FIG. 12 is a graph showing the fluorescent signal generated by qPCR by using ZIPR DDS with a probe oligonucleotide specific for a H3 influenza virus gene target nucleotide sequence.

FIG. 12 shows an amplification curve from an H3N2 infected patient sample using the ZIPR H3 probe above.

Example 7

Real Time PCR Using FLIP DDS Probes for the Detection of 16S of *Mycobacterium tuberculosis* Versus 16S of *Mycobacterium paratuberculosis*

The following FLIP DDS probe for the specific detection of *Mycobacterium tuberculosis* species was targeted to a site in the 16S gene that differs by one base from the 16S gene of *Mycobacterium paratuberculosis*. The probe was 3'-FAM-labeled and comprised an internal target sequence. The antiprobe component was 5'-BHQ1-labeled and was conjugated to a 3' primer sequence, in this example to the forward primer.

Only one flanking primer was used in conjunction with the FLIP probe components. During target amplification, the probe bound to the target sequence, leaving the antiprobe behind since it was attached to one primer that is incorporated into the amplicon. Thus the probe could flip forward to its target site, triggering fluorescent detection. The assay used a second primer that was not encumbered with an antiprobe. Comparison was made with a Taqman probe for the same target site, using both the forward and reverse primer and the same test samples. The primer and probe components and final concentrations were as follows:

```
FLIP probe:
                                        (SEQ ID NO.: 26)
TAGGACCACGGGATGCATGTCTT-FAM  at 125 nM;

FLIP antiprobe-primer:
                                        (SEQ ID NO.: 27)
dT-BHQ1-AAGACATGCATCCCGTGGT-spacer9-GGGATAAGCCTG
GGAAACTG at 200 nM;

Taqman probe:
                                        (SEQ ID NO.: 28)
FAM-CATGTCTTGTGGTGGAAAGC-BHQ1  at 100 nM;

For. primer:
                                        (SEQ ID NO.: 29)
GGGATAAGCCTGGGAAACTG at 200 nM;
and Rev. primer:
                                        (SEQ ID NO.: 30)
ACCCCACCAACAAGCTGATA at 200 nM.
```

Cycling conditions: Real-time PCR was conducted as described in Example 1.

Figure 13A:
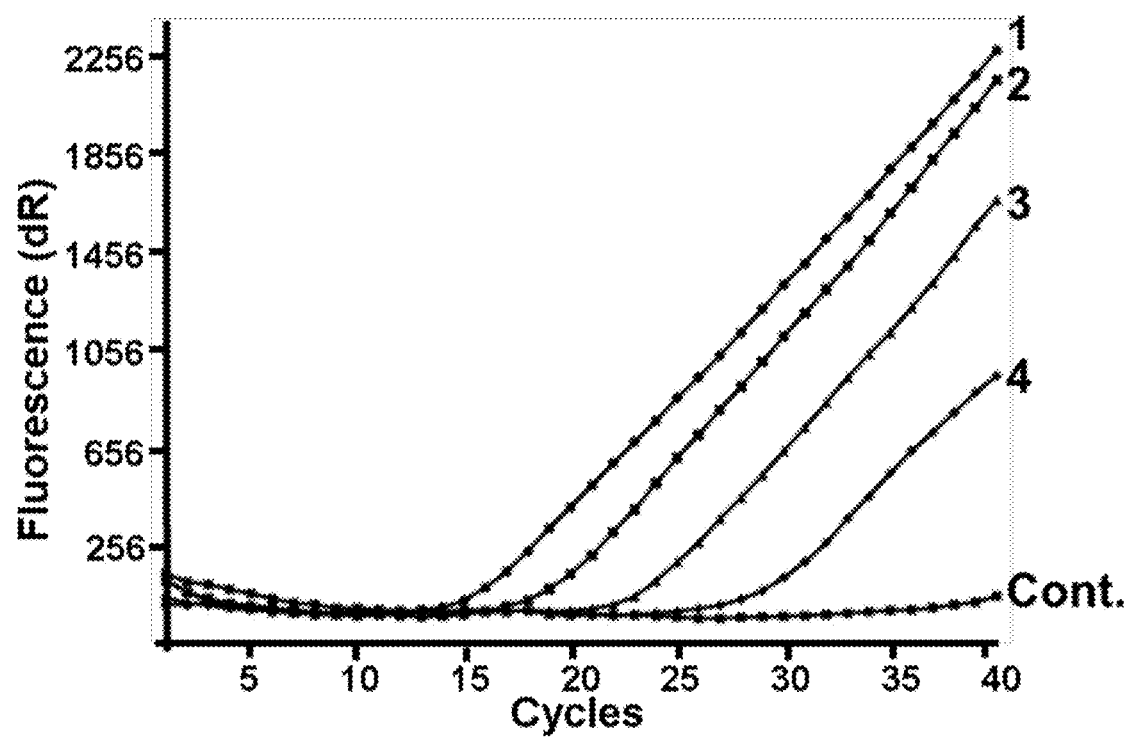
FIG. 13A is a graph showing the fluorescent signals generated by qPCR by using FLIP DDS probe oligonucleotides specific for a target region in the 16S gene of *Mycobacterium tuberculosis* that differs from the same target region in *Mycobacterium paratuberculosis* by a single base, using four concentrations of the *M. tuberculosis* target nucleotide sequence and a *M. paratuberculosis* control target nucleotide sequence.
Figure 13B:
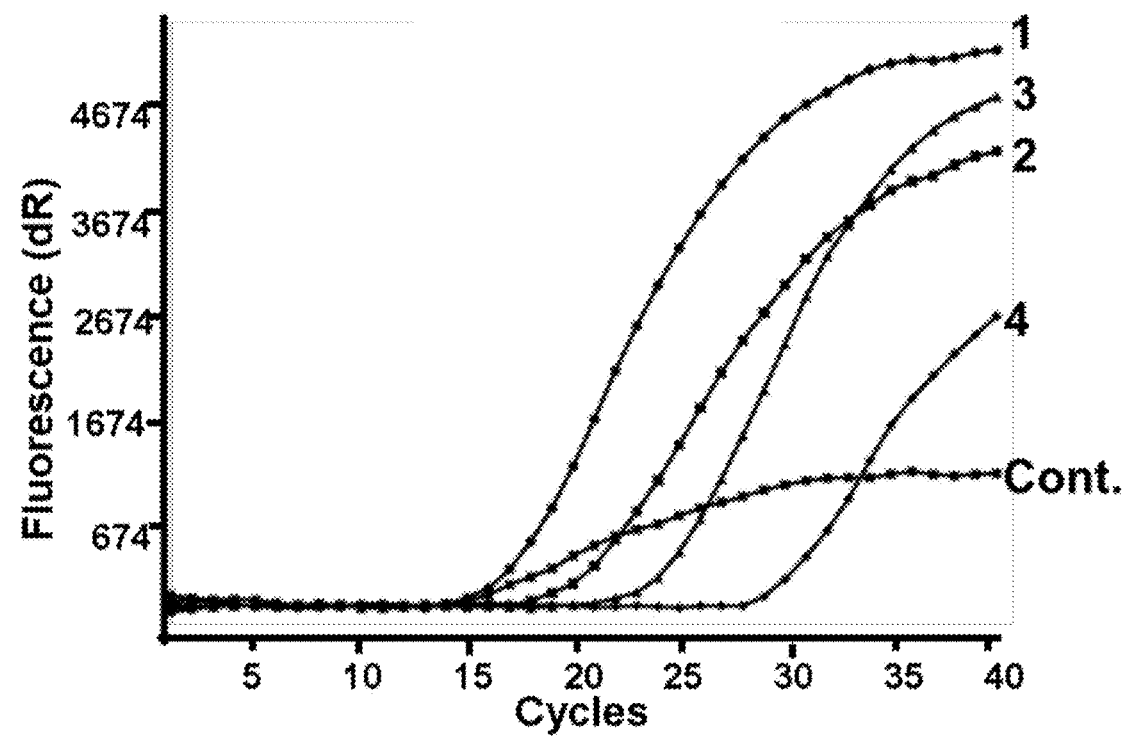
FIG. 13B is a graph showing the fluorescent signals generated by qPCR by using a TaqMan probe specific for a target region in the 16S gene of *Mycobacterium tuberculosis* that differs from the same target region in *Mycobacterium paratuberculosis* by a single base, using four concentrations of the *M. tuberculosis* target nucleotide sequence and a *M. paratuberculosis* control target nucleotide sequence.

FIG. 13A shows amplification curves from five tubes using the FLIP DDS probe specific for 16S *M. tuberculosis*. The four positive (upward) curves reflect detection of four samples of *M. tuberculosis* serially diluted 10:1. The negative curve reflects a sample of *M. paratuberculosis* that differs by one base in the probe region. FIG. 13B shows curves from five tubes using a Taqman probe specific for 16S *M. tuberculosis* at the same target region as the FLIP probe shown in FIG. 13A. The four high positive curves are from the same four serial dilutions of *M. tuberculosis* as shown above. The low positive curve overlapping the other curves is from the same *M. paratuberculosis* control sample as in FIG. 13A. This illustrates false positive detection occurring with the Taqman probe. The FLIP probe is more stringent and avoids such false positive detection.

Example 8

Real Time PCR Using G-Force DDS Probe for the Detection of the *M. tuberculosis* rpoB Gene A G-Force DDS probe for tuberculosis was designed to detect a region in the rpoB gene that encompasses codons 526 to 533. A generic probe:antiprobe signaling unit was joined to one primer and functioned in conjunction with the other flanking primer to amplify and detect the target site. The G-Force signaling unit comprised a FAM-labeled cytidine-rich probe segment, a spacer flanked by A's, and a guanine-rich antiprobe segment (as shown in SEQ ID NO.: 31).

In the absence of a target sequence, the probe and antiprobe segments fold together, with the spacer in between, due to the binding of complementary sequences. Since this brings the fluorophore next to a string of guanines, fluorescence was significantly diminished. But when the primer/probe unit was incorporated into the product, the antiprobe segment is copied, thereby preventing the probe segment from folding next to the antiprobe segment, and therefore signaling is released.

The G-Force probe and primer sequence and final concentrations are:

```
GF primer/probe:
                                        (SEQ ID NO.: 31)
FAM-CCCCTCCA-spacer18-AGGAGGGGG-CCGCTGTCGGGGTTGAC
at 100 nM;
and Reverse primer:
                                        (SEQ ID NO.: 32)
CACGCTCATGTGACAGACC at 200 nM.
```

The G-Force probe was used with two templates. One containing a single base mutant at codon 526 (tac), the other the wild sequence. The G-Force probe did not differentiate these two templates.

Cycling conditions: Real-time PCR was conducted as described in Example 1.

Figure 15:
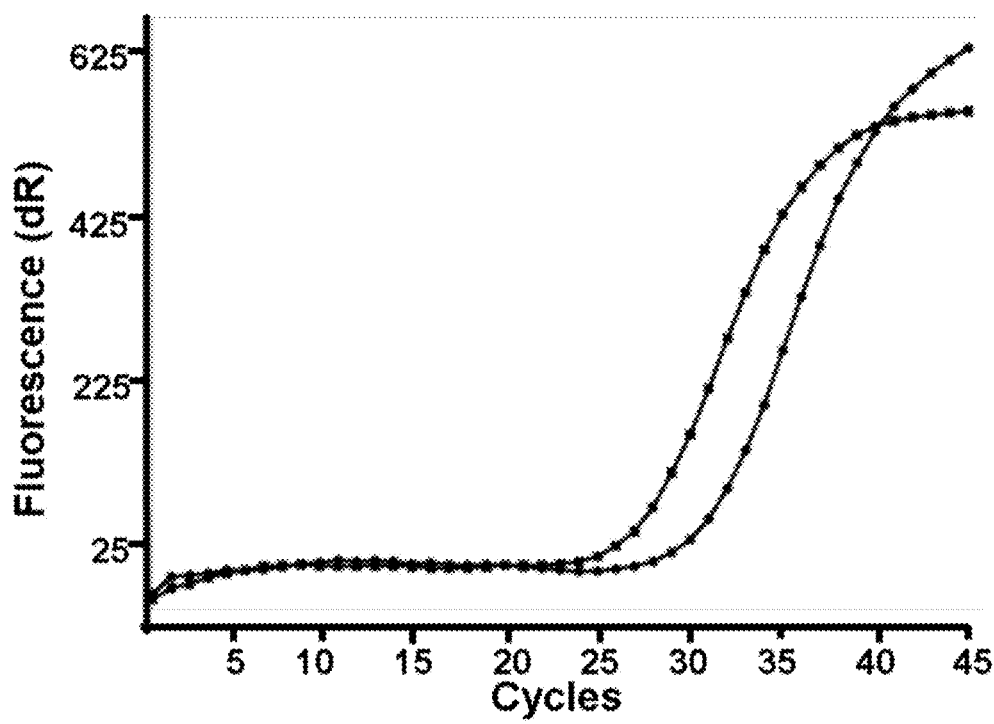
FIG. 15 is a graph showing the fluorescent signals generated by qPCR by using a G-Force primer-probe with either *M. tuberculosis* wild (W) or mutant (M) templates that do not differ in their primer sequences.

FIG. 15 shows the results from two tubes with the probe above showing positive curves with both the wild and mutant template.

Example 9

G-Force DDS Probe Combined with an iDDS Probe for Detection of a Single Base Mutant in the rpoB Gene of *M. tuberculosis*

The G-Force DDS probe from Example 8 above was used in conjunction with an iDDS probe targeting the wild sequence for the 526 codon of rpoB. The iDDS probe components and concentrations are below. This assay was intended to detect if a mutant is present at codon 526, the primary site for rifampicin resistant mutants, without having to detect each specific mutant with a different iDDS probe. Thus the iDDS probe gives a flat curve if a 526 mutant is present, while the G-Force probe will still give a positive curve. This positive/negative result confirms that the 526 itself codon is present, and then shows that it contains a mutant base, regardless of which base variant is present. While this positive/negative result confirms that only a resistant mutant is present, the assay can be ambiguous if the sample contains significant quantities of both wild and mutant templates and two positive curves are detected.

```
iDDS probe:
                                        (SEQ ID NO.: 33)
CalFluorRed610-CGGGGTTGACCCACTAGCG-phos at 200 nM
```

-continued

```
Antiprobe:
                                          (SEQ ID NO.: 34)
CGCTTGTGGGTCTACCCCG-BHQ2 at 400 nM.
```

Cycling conditions: Real-time PCR was conducted as described in Example 1.

Figure 16A:
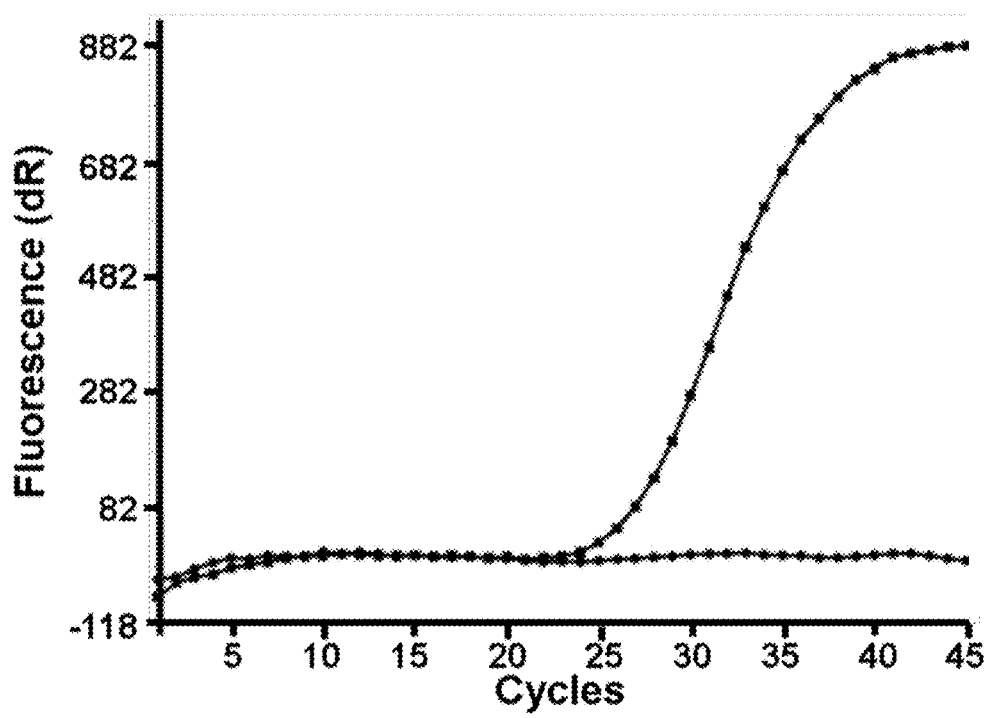
FIG. 16A is a graph showing the fluorescent signals generated by qPCR by using both a non-discriminatory G-Force probe and an iDDS probe that is specific for the wild sequence and using a *M. tuberculosis* mutant (M) template.

FIG. 16A shows one tube with the two probes above and with a mutant template for the 526 site. The G-Force probe showed a positive curve detecting the 526-533 region, but the more specific wild iDDS probe for the 526 site did not show a positive curve since the 526 site is mutant. This assay thus provides an index of rpoB 526 mutant status without detecting a specific mutant.

A G-Force probe can be combined with a iDDS probe to quantify the frequency of a specific mutant in a sample. The G-Force probe detects all amplicons of the target region while the iDDS probe only detects those amplicons that comprise the mutant sequence. Thus the signal is consistently high for the G-Force probe with either wild or mutant templates, while the signal height of the iDDS probe is in proportion to the frequency of the mutant template versus the wild template, and provides an indication of the relative proportions of wild versus mutant cells in a population of cells. The same would be true in reverse if the iDDS probe detected the wild and not the mutant sequence.

This capacity is shown with a G-Force probe for the inhA gene of *M. tuberculosis* combined with an iDDS probe for the wild inhA sequence at the site of a common drug resistant mutant using the following probes and primers:

```
Forward primer:
                                          (SEQ ID NO.: 35)
GCTCGTGGACATACCGATTT at 200nM;

inhA iDDS probe:
                                          (SEQ ID NO.: 36)
CalRed610-CCGACAACCTATCGTCTCGCC-Phos at 200 nM;

inhA antiprobe:
                                          (SEQ ID NO.: 37)
CGAGACGATAGGTTGTCGG-BHQ2 at 400 nM;
and InhA G-Force primer-probe:
                                          (SEQ ID NO.: 38)
CCCCTCCA-spacer18-AGGAGGGGGTCCGGTAACCAGGACTGAAC
at 100 nM.
```

Figure 16B:
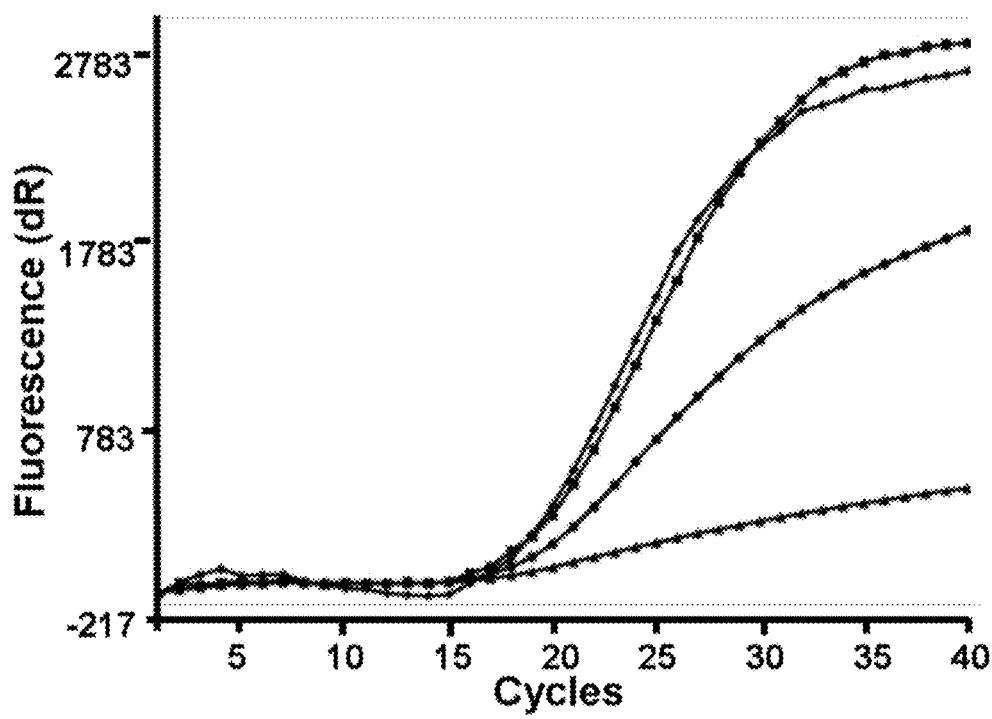
FIG. 16B is a graph showing the fluorescent signals generated by qPCR by using both a non-discriminatory G-Force probe and wild-type-specific iDDS probe with differing amounts of *M. tuberculosis* wild (W) versus mutant (M) template.

FIG. 16B shows a test where two tubes were run with the wild and mutant template mixed at either 75% wild:25% mutant or 25% wild:75% mutant. While the curves for the G-Force probe were the same for either template, the curves for the iDDS probe differed in height proportional to the percent wild template present.

Example 10 iDDS Probe-Based Mutant Detection Enhanced with "Wild Terminator" Method

Mutant detection with iDDS probes could be enhanced by a pre-amplification step that selectively amplified the targeted mutant templates and blocked the amplification of wild templates. After the pre-amp step, the reaction product was diluted and a small dilute sample was transferred to a real-time PCR reaction. Because of this process, wild type templates were almost eliminated and the qPCR reaction started with an amplified quantity of mutant templates. The result was that a sample with a low frequency of mutant templates could be efficiently detected by qPCR with an iDDS probe even if the original sample contained an abundance of wild templates that would otherwise obscure mutant detection.

The pre-amplification reaction used a set of primers flanking the targeted region, and the final reaction used a primer set that was partially or fully between the outer primers. The first, pre-amplification procedure was run in a standard PCR machine for 30 to 70 short cycles. One microliter of the first reaction was generally diluted with 100 to 500 microliters of water or buffer, and then a one microliter sample was transferred to a second reaction in a real-time PCR machine.

The first step used a Wild Terminator blocking probe comprising an unlabeled oligonucleotide that was complementary to the wild sequence and about 22 to 28 bases long—about 2 to 5 bases longer than the iDDS probe. The 5' end was modified to prevent 5'-nuclease digestion the attachment of a blocking moiety such as a biotin molecule, a ZNA, a MGB, or an arbitrary string of non-complementary bases (about 5-10). The 3'-end was modified with a molecule that prevents extension of the probe using such as a phosphate, an amino group, or a spacer. The Tm of the blocking probe was typically at least 5° C. higher than the iDDS probe so that any wild templates would bind to it strongly.

The blocking "Wild Terminator" probe, thus acted like an antiprobe in reverse, blocking wild templates while allowing iDDS probes for the mutant sequence to bind to, and detect, mutant templates. This example illustrates enhanced detection of the EGFR Exon 21 mutant site L858R (T>G) using the same iDDS probes described in Example 2 but providing mixed templates with a low frequency (0.2%) of the mutant sequence variant relative to the wild sequence variant.

The first pre-amplification step used the following templates and components: Templates: 10,000 copies wild EGFR Exon 21 858L; 20 copies mutant EGFR Exon 21 858R (0.2%). Outer forward primer: AGCCAGGAACGTACTGGTGA (SEQ ID NO.: 39) at 100 nM; Outer reverse primer: TGCCTCCTTCTGCATGGTAT (SEQ ID NO.: 40) at 100 nM; and Terminator blocking probe: Biotin-CTTTCCCACCAACGCAGATCAATTCCA-phos (SEQ ID NO.: 41) at 200 nM.

This first step comprised a 20 ml reaction using USB PCR master mix (2×). The reaction was started by heating to 95° C. for 3 minutes followed by 40 cycles of PCR at 95° C. for 2 sec, 50° C. for 2 sec, and 72° C. at 2 sec. This step inhibited or prevented wild template amplification while the mutant templates were amplified. From step 1 dilute 1/500, 1 ml was transferred to step 2.

The second qPCR step uses the following components and conditions:

```
Internal forward primer:
                                          (SEQ ID NO.: 11)
GAAAACACCGCAGCATGTC at 200 nM Internal reverse primer:
                                          (SEQ ID NO.: 12)
CTGCATGGTATTCTTTCTCTTCC at 200 nM;

Mutant probe 858R:
                                          (SEQ ID NO.: 7)
FAM-CAGATTTTGGCC GGGCCAAACTG-Phos at 200 nM;

Mutant antiprobe:
                                          (SEQ ID NO.: 8)
CAGTTTGGCCCGCCCAATATCTG-BHQ1 at 400 nM;
```

-continued

Wild probe 858L:
(SEQ ID NO.: 9)
CalRed610-CAGATTTTGGGCTGACCAAACTG-Phos at 200 nM;
and Wild antiprobe:
(SEQ ID NO.: 10)
GCAGTTTGGCCAGCCCATAATCTG-BHQ2 at 400 nM.

Cycling conditions: Real-time PCR was conducted as described in Example 1 except that the annealing/extension step was at 52° C. for 1 min.

Figure 14:
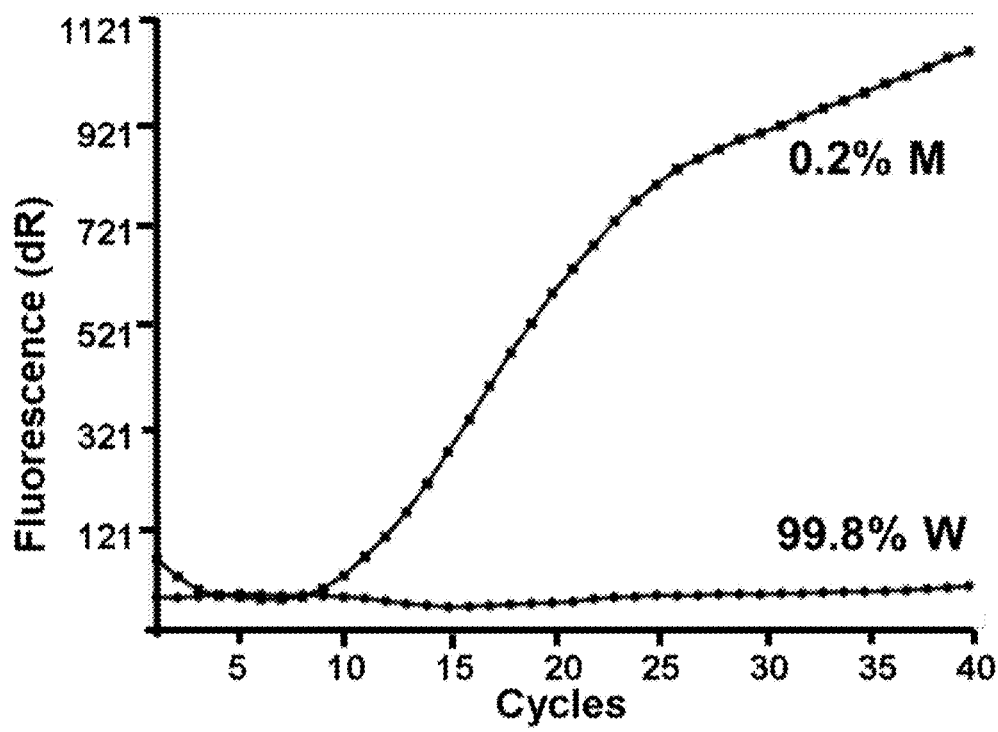
FIG. 14 is a graph showing the fluorescent signals generated by qPCR by using two-step target enhancement with a "Wild Terminator" blocking probe and an iDDS probe specific for the 858R variant EGFR with a mixed sample of 0.2% 858R target nucleotide sequence and 99.8% wild-type variant target nucleotide sequence.

FIG. 14 shows qPCR curves from two tubes containing the same reaction product from the first pre-amp step but with different probes, wild and mutant, in each tube. The positive (upward) curve shows the mutant detecting very early with exponential amplification starting at 9 cycles. The negative curve shows no detection of the wild template that originally was in abundance.

Example 11

One Step iDDS and "Wild Terminator" Method Detecting EGFR Exon 21 Mutants

The "Wild Terminator" probe and the iDDS probe were used together in a single real-time PCR reaction, the "Wild Terminator" probe inhibiting or blocking amplification of the wild templates and the iDDS probe detecting the mutant templates. The procedure would only work if the mutant frequency is about 1% or higher. In this example, 200 copies of the mutant template were used with 10,000 copies of the wild template (2% mutant). All primers and probes were the same as in Example 10 above, except the internal primers were used at 400 nM. The "Wild Terminator" probe was used at 150 nM, but similar results were seen with the "Wild Terminator" probe at 100 or 200 nM.

Cycling conditions: Real-time PCR was conducted as described in Example 1 with the annealing/extension step at 52° C. for 1 min.

Figure 17:
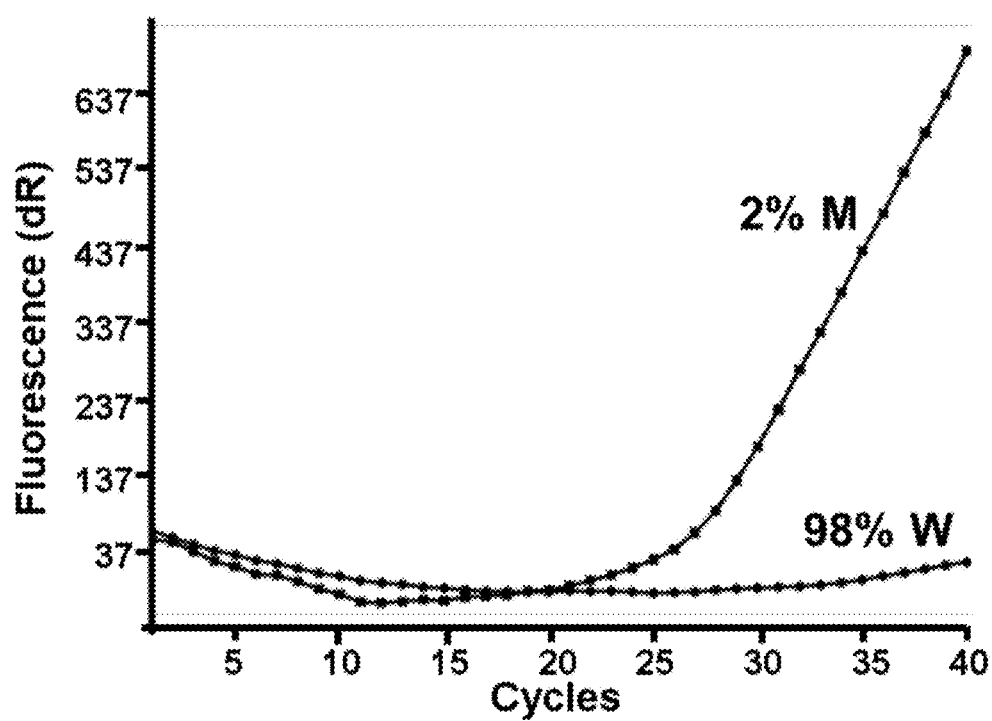
FIG. 17 is a graph showing the fluorescent signals generated by qPCR by using one-step target enhancement with a "Wild Terminator" blocking probe and an iDDS probe specific for the 858R mutant variant EGFR with a mixed sample of 2% 858R target nucleotide sequence and 98% wild-type variant target nucleotide sequence.

FIG. 17 shows two curves from one tube containing the "Wild Terminator" probe and the wild and mutant iDDS probes for the L858R site in EGFR.

Example 12

ISAM Isothermal Amplification with ZIPR DDS Probes and qPCR Detection

DNA or RNA target sequences can be isothermally amplified and detected with a DDS primer-probe at one end and a primer with a 5' RNA polymerase promoter sequence at the other end. In this example, a T7 RNA polymerase promoter sequence was used. This method employs a reverse transcriptase to create a cDNA copy of the target region with the T7 site appended to the 5' end. Then a ZIPR DDS primer-probe served as a primer to copy the cDNA including the T7 site, thereby creating a double stranded product with a T7 promoter recognition sequence. A RNA polymerase, in this case a T7 RNA polymerase, then made RNA copies of the product that served as template for further amplification cycles, alternating between DNA and RNA products generated. RNaseH facilitated this process by degrading the RNA strand of an RNA:DNA hybrid. RNaseH can be provided separately, or as a reverse transcriptase enzyme with RNase function, to make cDNA copies of the RNA products.

A NUCLISENS® Basic Kit (BioMerieux, Inc) was used. During amplification, the fluorescent-labeled ZIPR primer-probes were incorporated into the DNA products and were separated from any quencher-labeled antiprobes available, thereby providing qPCR detection. Due to the low temperature amplification, the antiprobes were made shorter. The probe and primer components were used as follows:

GAPDH-Cy3F1:
(SEQ ID NO.: 42)
Cy3-GAGTCAACGGATTTGGTCGT at 200 nM;

GAPDH-BHQ2:
(SEQ ID NO.: 43)
ATCCGTTGACTC-BHQ2 at 400 nM;
and

GAPDH-T7R1:
(SEQ ID NO.: 44)
AATTCTAATACGACTCACTATAGGGAGAAGGGACAAGCTTCCCGTTCT
CAG at 200 nM.

This test was performed with 1 ng of GAPDH RNA as the starting template. The initial RT step was performed at 65° C. for 5 mins, and then 41° C. for 5 mins. Exponential ISAM was then performed using such as a qPCR machine or a water bath between 37 and 45 degrees, most typically at 40° C. to 42° C. In one example, the qPCR step was run with two slightly different temperatures, cycling back and forth between 42° C. for 30 sec, and 40° C. for 30 sec, for 80 cycles. Fluorescent emissions were assessed at the second step per cycle (40° C. step).

In FIG. 18, the positive amplification curve shows detection of the ISAM qPCR DNA products with the ZIPR DDS primer-probe. The RNA products were not detected. Most of the exponential amplification phase was completed in the first 20 mins.

Example 13

ISAM Isothermal Amplification with Internal DDS (iDDS) Probes

ISAM amplification and qPCR detection can be performed as in Example 12 above, but using an internal DDS probe instead of a terminal primer-probe. In addition, both the forward and reverse primers could have a T7 sequence appended, a modification that increases the quantity of products generated about 20 to 50 percent. However, due to the low temperature used, the DDS probe and antiprobe were modified by using a long probe (24 bp) and a shorter antiprobe (15 bp).

GAPDH-T7F1:
(SEQ ID NO.: 45)
AATTCTAATACGACTCACTATAGGGAGAAGGGAGTCAACGGATTTGGT
CGT at 300 nM;

GAPDH-R1:
(SEQ ID NO.: 46)
AATTCTAATACGACTCACTATAGGGAGAAGGGACAAGCTTCCCGTTCT
CAG at 300 nM;

GDH iDDS probe:
(SEQ ID NO.: 47)
FAM-CCTTCATTGACCTCAACTACATGG-amino at 150 nM;
and GDH iDDS antiprobe:
(SEQ ID NO.: 48)
TGAGGTCAATGAAGG-BHQ1 at 300 nM.

Figure 19:
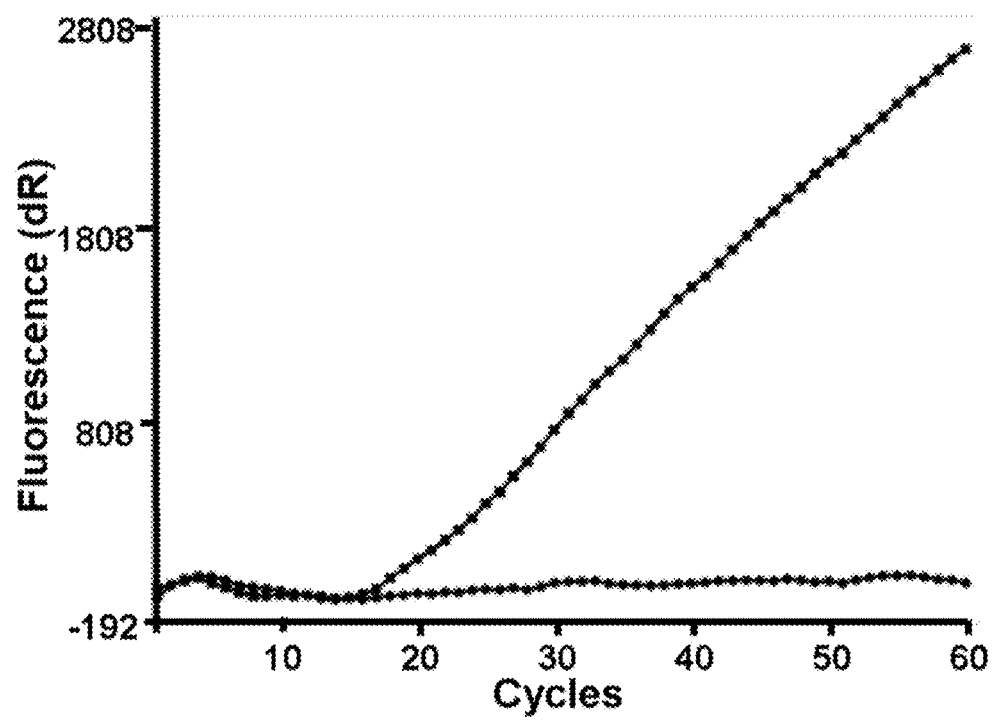
FIG. 19 is a graph showing the fluorescent signal generated by iDDS and ISAM.

The testing templates were GAPDH RNA and HIV RNA. Both the RT-PCR and the qPCR steps were performed as described in Example 13 except that qPCR cycling was for 60 one-minute cycles at one temperature, 41° C., with fluorescent detection assessed every cycle. In FIG. 19, the positive amplification curve shows ISAM qPCR detection of the GAPDH DNA products with an internal DDS probe and antiprobe. The flat curve was from the HIV control template. With the internal DDS probe, detection was more stringent and thus the amplification curve rose more gradually.

Example 14

On-Chip ISAM Isothermal Amplification and Fluorescent Detection

A chip array was hand-printed on CODELINK® slides (GE Healthcare) with multiple spots that contained primers for either the GAPDH gene or the Rab9 gene. Those primers comprised from the 5' end: an amino modification, a spacer, a T7 sequence, and a gene-specific reverse primer sequence. Following the CODELINK® protocol, the primers were covalently joined to the printed slides via their 5' amino modification. They were then treated to block non-specific binding, washed and dried. The spots were arranged in a semi-checker board pattern alternating between GAPDH and Rab9 primer spotting. The ISAM reaction was done on the chip, adding 150 ng each of GAPDH RNA and Rab9 RNA, plus a Cy3-labeled GAPDH probe comprising a forward primer sequence, and a FAM-labeled Rab9 probe comprising a T7 sequence and a forward primer sequence.

The reaction was run under a coverslip, but in a sealed chamber, and maintained at 41° C. for at least 2 hrs in a water-bath. Chips were then washed with: 2×SSC/0.1% SDS, 0.1×SSC/0.1% SDS, 1×SSC, then 0.01×SSC, then spun dry. Detection was made with a Perkin Elmer microarray scanner. The GDH and Rab9 specific primers and probes are:

GDH-R1s:
(SEQ ID NO. 49)
amino-spacer18-ATTTCTAATACGACTCACTATAGGGAGAAGGGAC
AAGCTCCCGTTCTCAG;

Rab9-R1s:
(SEQ ID NO. 50)
amino-spacer18-ATTTCTAATACGACTCACTATAGGGAGAAGGAAA
TGGTGTCCTCAGGCTTC;

GDHCy3F1:
(SEQ ID NO. 51)
Cy3-GAGTCAACGGATTTGGTCGT at 900 nM;
and

Rab9-FAM-T7F1:
(SEQ ID NO. 52)
FAM-AATTCTAATACGACTCACTATAGGGAGAAGGCAATGGCAGGAAAA
TC at 900 nM.

Figure 20:
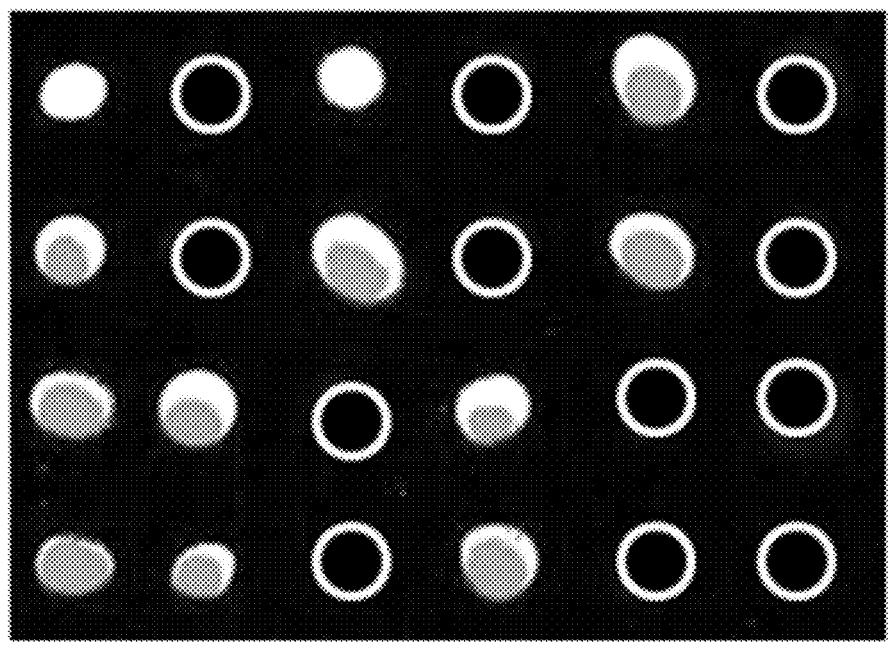
FIG. 20 is a digital image of an array detection of ISAM on chip, Cy3 dots, FAM circles.

In FIG. 20, a pattern of green and blue spots was observed on the array indicating that on-chip ISAM gene specific amplification and detection could be performed with one primer attached to the chip. Due to low shading differences between the black background and the blue FAM-labeled Rab9 specific spots, those gene specific fluorescent dots were represented as white circles in the black/white figure shown. The green Cy3-labeled GAPDH specific spots can be more easily seen in the black/white figure as either solid white dots or white dots with a gray center. Amplification and detection was exclusive to each gene.

Example 15

Detecting a Variable Deletion Mutant of EGFR Exon 19 Using Two Probe:Antiprobe Compositions on the Same Amplicon In lung cancer and related disease, variable deletion mutants commonly occur in exon 19 of the EGFR gene involving the loss of 9 to 24 bases in the region comprising codons 746 to 753, and such deletions are the most common biomarker for responsiveness to tyrosine kinase inhibitors. These diagnostic deletions in exon 19 (known as Del-19) have generally been detected by sequencing methods. Dahse et al. 2008 has developed a PCR and gel-based assay that uses a special primer to bridge and amplify the most common 15 bp Del-19 mutant, however, this assay fails with other exon 19 deletion mutants. The example reported here overcomes this limitation using a pair of probe:antiprobe compositions in a qPCR assay to detect two aspects of an EGFR exon 19 amplicon. A primer-probe with one label is used to amplify and detect the terminal end of all amplicons of the targeted segment with or without a Del-19 mutant, and a second iDDS probe with a different label will detect an internal segment comprising codons 746 to 753 only if the wild type sequences are present. By subtraction, this two probe system thus discerns the relative proportion of Del-19 mutants to wild type.

The primer-probe employed is a ZIPR probe:antiprobe that also serves as a forward primer: CalRed610-TCTG-GATCCCAGAAGGTGAG (SEQ ID NO: 56) at 200 nM; and CTCACC TTCTGGGTTCCAGA-BHQ2 (SEQ ID NO: 57) at 400 nM. The internal iDDS probe:antiprobe comprises: Fam-CAAGGAATTAAGAGAAGCAACATC-Phos (SEQ ID NO: 81) at 200 nM; and GATGTTGCCTCTCT-TAATTCCTTG-BHQ1 (SEQ ID NO: 82) at 400 nM. The flanking reverse primer comprises: CGTAGGCTT-CATCGAGGATT (SEQ ID NO: 53) at 200 nM. Sometimes a small quantity (~100 nM) of an unlabeled forward primer (TCTGGATCCCAGAAGGTGAG, SEQ ID NO: 78) is also provided to reduce a strong ZIPR signal and bring it in balance with the iDDS signal to facilitate diagnostic interpretation of the Del-19 mutant frequency.

Real time PCR was conducted as described in Example 1 using artificial gene targets with and without a 9 bp or a 15 bp deletion or using patient samples with or without a known Del-19 mutant. If all templates are wild, the iDDS signal should be relatively equivalent to the ZIPR probe signal, but if Del-19 mutants are present, the iDDS signal, compared to the ZIPR probe signal, should drop significantly relative to mutant frequency. This expected result was observed in the templates and samples tested.

Figure 21:
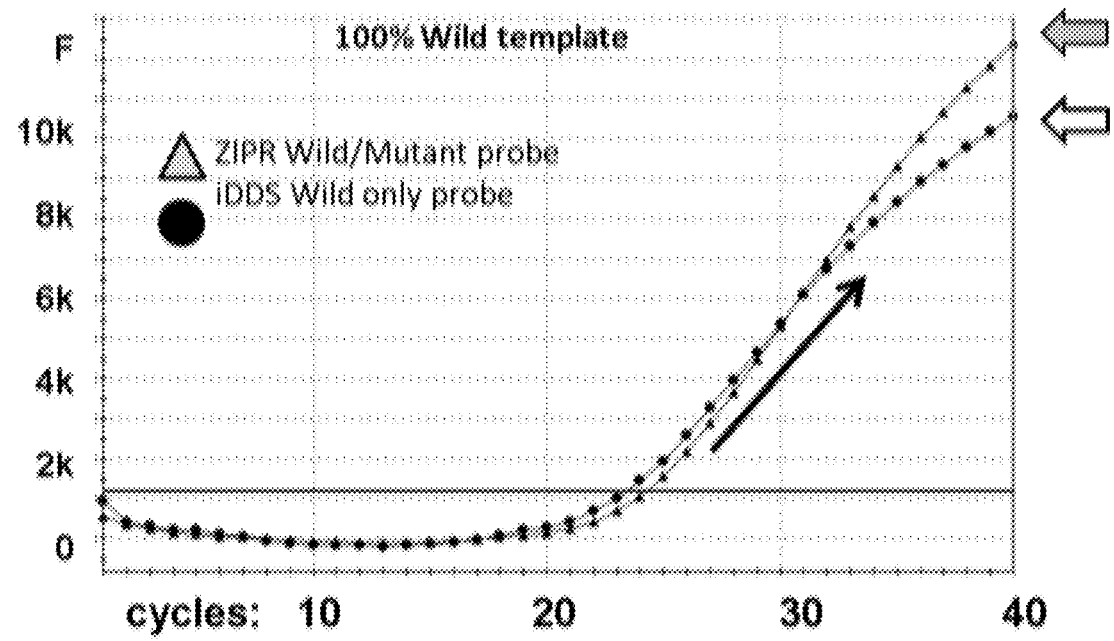
FIG. 21 is a graph showing the detection of a EGFR Del-19 mutant with a wild only iDDS probe and a non-specific ZIPR probe wherein the curves show two signals in parallel with a 100% wild template, and a flat iDDS signal with a 100% mutant template.
Figure 22:
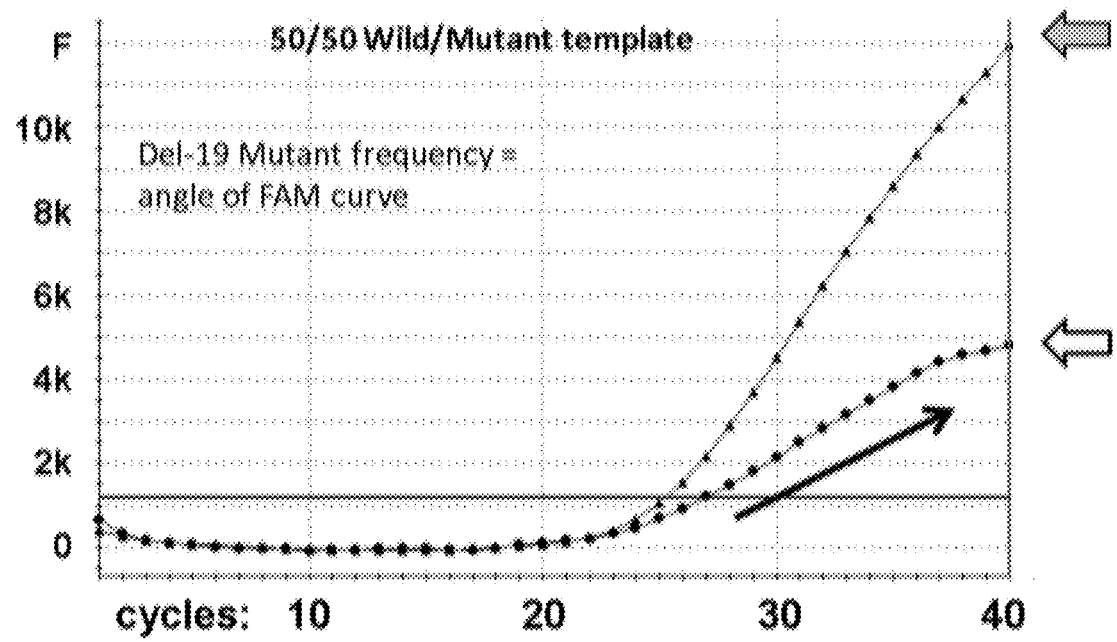
FIG. 22 is a graph showing the detection of EGFR Del-19 mutants with a wild only iDDS probe and a non-specific ZIPR probe wherein the curves show two signals in parallel with a lower iDDS signal with a 50/50 wild/mutant template, and a flat iDDS signal with a 100% mutant template.
Figure 23:
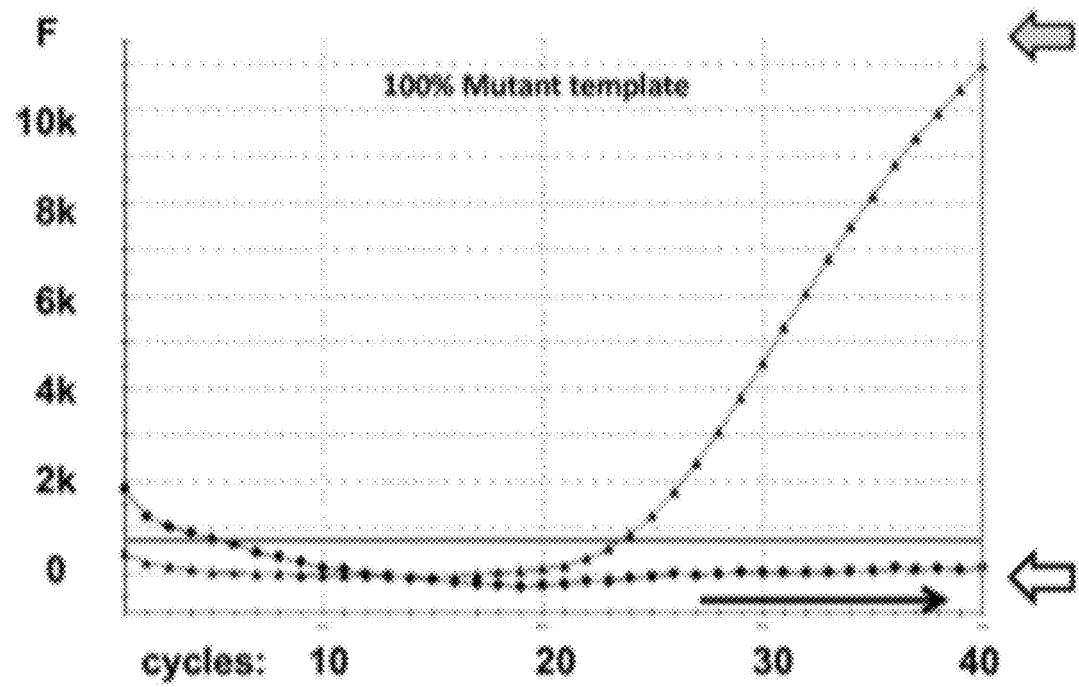
FIG. 23 is a graph showing the detection of EGFR Del-19 mutants with a wild only iDDS probe and a non-specific ZIPR probe with a 100% mutant template with a flat iDDS signal with a 100% mutant template.
Figure 24:
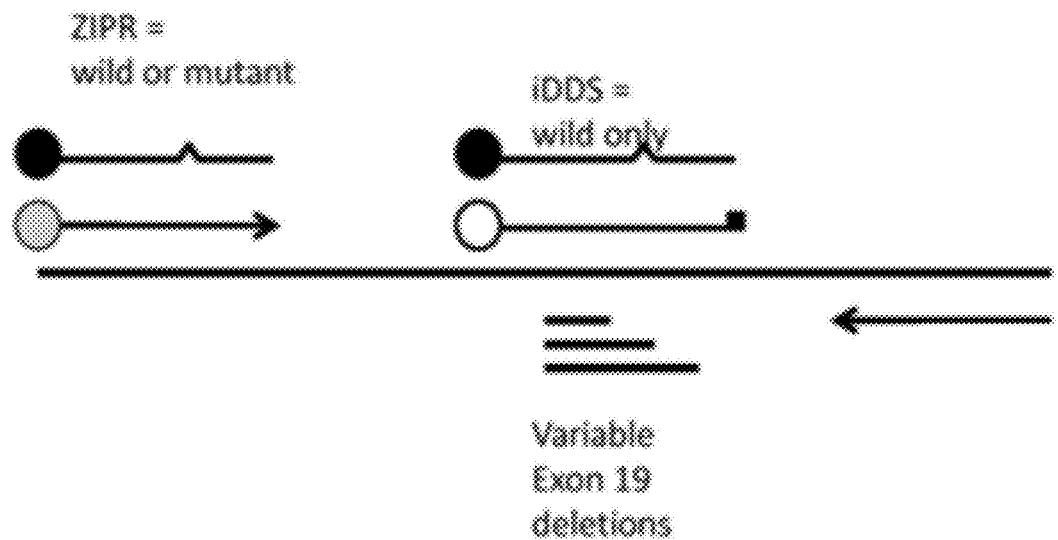
FIG. 24 shows the detection scheme for the EGFR Del-19 mutant assay.

FIG. 21 shows curves from one tube using the two probes above and with 100% wild template. The ZIPR probe shows a positive curve detecting the targeted amplicon, and the iDDS probe shows an equivalent positive curve since all templates are wild. FIG. 22 shows a diminished iDDS curve relative to the ZIPR probe curve since the template is 50% mutant. FIG. 23 shows a positive ZIPR probe curve and a flat iDDS curve since the wild sequence is absent at the Del-19 target site. This assay thus provides an index of the Del-19 mutant frequency without detecting a specific mutant sequence. The ZIPR signal is consistently high with either wild or mutant templates, while the signal height of the iDDS probe varies in proportion to the frequency of the wild vs. mutant template regardless of the size or sequence of the mutant present.

Example 16

An iDDS Probe:Antiprobe Assay to Detect a Single Base Mutant of EGFR Exon 20 at Codon 790 Associated with Acquired Resistance to Tyrosine Kinase Inhibitors Used for Cancer Therapy Patients with non-small cell lung cancer that are responsive to tyrosine kinase inhibitors typically relapse after one year due to an EGFR mutation T790M in exon 20. This mutation is due to a C to T base pair change in the second letter of codon 790, causing a threonine to methionine missense substitution (ACG>ATG). Detecting such single base mutants thus provides a diagnostic indicator for a change in therapy. In this example, a qPCR assay employs an iDDS probe:antiprobe to detect the presence of the 790M mutant sequence in an amplified EGFR template. The primers and probes comprise:

F-primer:
(SEQ ID NO: 83)
GCATCTGCCTCACCTCCAC at 200 nM;

R-primer:
(SEQ ID NO: 84)
GTCTTTGTGTTCCCGGACAT at 200 nM;

Probe:
(SEQ ID NO: 85)
FAM-TGAGCTCCATGATGAGTTGCACG-Phos at 200 nM;
and

Antiprobe:
(SEQ ID NO: 86)
CGTGCAACTCTTCATGCAGCTCA-BHQ1 at 400 nM.

Cycling conditions: Real-time PCR was conducted as described in Example 1. A positive curve indicates the 790M sequence is present.

Example 17

Multiplex Assay to Detect Influenza A or B Based on Two ZIPR Probe:Antiprobe Compositions This assay employs two ZIPR probes with different fluorescent labeling to detect either influenza A or influenza B in a sample comprising:

F-primer:
(SEQ ID NO: 87)
CTTCTAACCGAGGTCGAAACGTA at 200 nM;

A-Probe:
(SEQ ID NO: 88)
Fam-GCTTTGAGGGGGCCTGA at 200 nM;

A-Antiprobe:
(SEQ ID NO: 89)
TCAGCCCCCCTCAAAGC-BHQ-1 at 400 nM;

R-primer:
(SEQ ID NO: 90)
CTAATTGTCTCCCTCTTCTGGTGA at 200 nM;

B-Probe:
(SEQ ID NO: 91)
CalRed610-CCCAATTTGGTCAAGAGCAC at 200 nM;
and

B-Antiprobe:
(SEQ ID NO: 92)
GTGCTGATGACCAAATTGGG-BHQ-2 at 400 nM.

Cycling conditions: Real-time PCR was conducted as described in Example 1. A FAM-positive curve indicates flu A is present and a CalRed610 positive curve indicates flu B is present.

Example 18

Multiplex Assay to Detect Variable Mutations in KRAS Exon 1, Codons 12 and 13, Associated with Reduced Response to EGFR Targeted Therapies in Lung and Colon Cancer Patients This assay is similar to the Del-19 detection scheme and employs a non-specific ZIPR probe system with HEX fluorescent labeling and a wild type iDDS probe system with FAM labeling. The iDDS probe comprises FAM-CC-TACGCCACCAGCTC-Phos (SEQ ID NO. 93) at 200 nM; and GAGGTGGTGGCGTAGG-BHQ1 (SEQ ID NO. 94) at 400 nM. The ZIPR probe comprises HEX-TGGATCATAT-TCGTCCACAAAA (SEQ ID NO. 95) at 200 nM and TTTTGAG GACGAATATGATCCA-BHQ1 (SEQ ID NO. 96) at 400 nM. The flanking primer is CCTGCT-GAAAATGACTGAATATAAA (SEQ ID NO. 97) at 200 nM.

What is claimed is:

1. A DNA Detection Switch (DDS) probe system for concurrent amplification and selective detection of a target nucleotide sequence of interest in a sample comprising:

a first probe:antiprobe detection system for a liquid-phase hybridization comprising:

a) a probe oligonucleotide comprising:

a nucleotide sequence consisting of 14 bases to 24 bases that is complementary to a first target nucleotide sequence and a second target nucleotide sequence, said first target nucleotide sequence and the second target nucleotide sequence differing by at least one mismatched base; and a fluorescence emitter attached thereto at its 5' end or at its 3' end; and b) an antiprobe oligonucleotide in an excess amount over the amount of the probe oligonucleotide, said antiprobe oligonucleotide comprising:

a fluorescence modulator attached to an end of the antiprobe oligonucleotide that is opposite the 5' end or the 3' end of the probe oligonucleotide to which the fluorescence emitter is attached;

a nucleotide sequence that has an equal length of the nucleotide sequence of the probe oligonucleotide and fully complementary to the nucleotide sequence of the probe oligonucleotide sequence except for at least one mismatched base that is selected from A, T, G and C and located in a non-terminal, non-central position of the antiprobe oligonucleotide in a duplex formed by the probe oligonucleotide and the antiprobe oligonucleotide and said fluorescence modulator of the antiprobe oligonucleotide diminishes a fluorescent signal of the fluorescence emitter of the probe oligonucleotide when the antiprobe oligonucleotide hybridizes to the probe oligonucleotide, a duplex formed by the probe oligonucleotide and the first target nucleotide sequence and the duplex formed by the probe oligonucleotide and the antiprobe oligonucleotide differ by at least 2 kcal/mol in Gibbs free energy (G) and at least 4° C. in melting temperature (Tm), and a duplex formed by the probe oligonucleotide and the second target nucleotide sequence, and the duplex formed by the probe oligonucleotide and the first target nucleotide sequence differ by at least 4 kcal/mol in G and at least 8° C. in Tm such that in a solution, an affinity of the probe oligonucleotide to the antiprobe oligonucleotide is higher than an affinity of the probe oligonucleotide to the second target nucleotide sequence, and, an affinity of the probe oligonucleotide to the first target nucleotide sequence is higher than the affinity of the probe oligonucleotide to the antiprobe oligonucleotide and under solution hybridization conditions, 1) when the first target nucleotide sequence is present in the sample, after adding the probe oligonucleotide and the antiprobe oligonucleotide into the sample, the probe oligonucleotide preferentially forms a first duplex with the first target nucleotide sequence in the solution and the probe oligonucleotide not duplexed with the first target nucleotide sequence forms a second duplex with the antiprobe oligonucleotide in the solution thereby generating:

a first fluorescent intensity from the first duplex, said first fluorescent intensity from the first duplex proportional to an amount of the first target nucleotide sequence in the sample; and a baseline second fluorescent intensity from the second duplex, said baseline second fluorescent intensity of the second duplex diminished relative to the first fluorescent intensity from the first duplex due to an interaction between the fluorescence emitter and the fluorescence modulator in the second duplex; or 2) when the first target nucleotide sequence and the second target nucleotide sequence are absent in the sample, after adding the probe oligonucleotide and the antiprobe oligonucleotide into the sample, the probe oligonucleotide preferentially forms the second duplex with the antiprobe oligonucleotide in the solution, thereby generating the baseline second fluorescent intensity from the second duplex; or 3) when the first target nucleotide sequence is absent in the sample and the second target nucleotide sequence is present in the sample, after adding the probe oligonucleotide and the antiprobe oligonucleotide into the sample, the probe oligonucleotide preferentially forms the second duplex with the antiprobe oligonucleotide in the solution and does not form a third duplex with the second target nucleotide sequence in the solution, thereby generating the baseline second fluorescent intensity from the second duplex.

2. The DDS probe system of claim 1, wherein, if the third duplex is formed by hybridizing the second target nucleotide sequence to the nucleotide sequence of the probe oligonucleotide, the third duplex has an internal two or three base non-hybridized region and has a G and T less than the G and T of the second duplex.

3. The DDS probe system of claim 1, further comprising a Taqman probe or a Molecular Beacon probe comprising a sequence partially complementary to the nucleotide sequence in the antiprobe oligonucleotide.

4. The DDS probe system of claim 1, wherein the fluorescence modulator is a fluorescence quencher compound, or a fluorescent compound having an excitation wavelength overlapping with an emission wavelength of the fluorescence emitter and an emission wavelength greater than the emission wavelength of the fluorescent emitter.

5. The DDS probe system of claim 1, wherein the probe system is selected from the group consisting of:

(i) an iDDS probe system comprising the probe oligonucleotide and the antiprobe oligonucleotide of claim 1, wherein the 3' end of the probe oligonucleotide, and optionally, the 3' end of the antiprobe oligonucleotide, is/are blocked to prevent a polymerase extension reaction; and a pair of flanking primers used for amplifying a nucleic acid region comprising the first target nucleotide sequence;

(ii) a Flip probe system comprising the probe oligonucleotide and the antiprobe oligonucleotide of claim 1, wherein the 3' end of the antiprobe oligonucleotide is attached to a first primer oligonucleotide via an optional abasic spacer; and a second primer oligonucleotide, wherein the first primer oligonucleotide and the second primer oligonucleotides are used for amplifying a nucleic acid region comprising the first target nucleotide sequence; and (iii) a ZIPR probe system comprising the probe oligonucleotide and the antiprobe oligonucleotide of claim 1, wherein the nucleotide sequence of the probe oligonucleotide also comprises a primer sequence and is used to cooperate with a second primer oligonucleotide to amplify the first target nucleotide sequence.

6. The DDS probe system of claim 5, further comprising a second probe:antiprobe detection system, wherein the probe oligonucleotide from the first probe:antiprobe detection system is a first probe oligonucleotide with a first fluorescence emitter attached thereto and a probe oligonucleotide from the second probe:antiprobe detection system is a second probe oligonucleotide with a second fluorescence emitter attached thereto, said first probe oligonucleotide and said second probe oligonucleotide selectively hybridize to specific target nucleotide sequences of a nucleic acid template; and wherein the first fluorescence emitter is different from the second fluorescence emitter, wherein:

(i) the first probe oligonucleotide is a first primer-probe that is used for cooperating with a primer oligonucleotide to amplify the first target nucleotide sequence in the nucleic acid template and produce a first amplificon comprising a first amplicon sequence labeled with the first fluorescence emitter such that a first fluorescent signal intensity of the first amplicon sequence is proportional to an amount of the first amplicons, and (ii) the second probe oligonucleotide is either a second primer-probe or an internal probe with a sequence complementary to the second target nucleotide sequence that is used to amplifying a second amplicon comprising a second amplicon sequence labeled with the second fluorescence emitter such that second fluorescence signal intensity of the second amplicon sequence is proportional to an amount of the second amplicon.

7. The DDS probe system of claim 1, further comprising a one-component G-Force primer-probe for amplifying and labeling a segment of the first target nucleotide sequence, said one-component G-Force primer-probe comprising, in a sequential order: (1) a fluorescence emitter attached to the probe oligonucleotide at its 5' end, (2) a cytidine-rich oligonucleotide segment with a length of 7 to 9 bases, (3) an abasic spacer, (4) an antiprobe oligonucleotide comprising a guanine-rich segment complementary to the cytidine-rich oligonucleotide segment, and (5) a 3' primer sequence complementary to one end of the first target nucleotide sequence such that, when said one-component G-Force primer-probe is not hybridized with the first target nucleotide sequence, the cytidine-rich oligonucleotide segment folds over and hybridizes to the guanine-rich segment whereby the fluorescence emitter of the one-component G-Force primer probe is juxtaposed to guanine bases in the guanine-rich oligonucleotide segment, thereby the guanine bases in the guanine-rich oligonucleotide segment quenches a fluorescent signal from the fluorescence emitter of said one-component G-Force primer-probe; and when the first target nucleotide sequence is amplified with said one-component G-Force primer-probe and a second primer oligonucleotide, the primer sequence in said one-component G-Force primer-probe hybridizes to the one end of the first target nucleotide sequence such that the cytidine-rich oligonucleotide segment and the guanine-rich oligonucleotide segment in said one-component G-Force primer-probe cannot hybridize to each other and thereby the fluorescent signal from the fluorescence emitter of said one-component G-Force primer-probe is detected.

8. The DDS probe system of claim 1, further comprising: an isothermal amplification system suitable for amplifying and detecting the first target nucleotide sequence from an RNA or a DNA, said isothermal amplification system comprising a RNA polymerase promoter enzyme, a reverse transcriptase enzyme, an RNase H enzyme, a primer-probe oligonucleotide and a flanking primer wherein:

the primer-probe oligonucleotide is used to cooperate with the flanking primer to amplify the first target nucleotide sequence;

the flanking primer further comprising a 5' RNA polymerase promoter sequence;

the primer-probe oligonucleotide optionally comprising the 5' RNA polymerase promoter sequence; and one of the primer-probe oligonucleotide and the flanking primer is optionally affixed to a solid substrate.

9. The DDS probe system of claim 1, further comprising an isothermal amplification system suitable for amplifying and detecting a RNA or DNA target sequence, said isothermal amplification system comprising a RNA polymerase promoter enzyme, a reverse transcriptase enzyme, a RNase H enzyme and a pair of flanking primers wherein one or two of the flanking primers in the pair further comprises a 5' RNA polymerase promoter sequence and one of the flanking primers in the pair optionally is affixed to a solid substrate; wherein the probe oligonucleotide of the first probe:antiprobe detection system is complementary to an internal target sequence with a length of 20 to 25 nucleotides and the antiprobe oligonucleotide has a length of 10 to 15 nucleotides.

10. The DDS probe system of claim 1, wherein the first target nucleotide sequence is a nucleotide variant of exon 19, 20 or 21 of the EGFR gene, a vitamin K epoxide reductase complex subunit 1 (VKORC71) gene, a cytochrome P450 2C9 (CYP2C9) gene, a beta-D-glucuronidase (uidA) gene of E. coli, 16S gene of a gram positive bacterium, 16S gene of a gram negative bacterium, a mycobacterium nicotinamide adenine dinucleotide-dependent enoyl-acyl carrier protein reductase (inhA) gene, a mycobacterium DNA-directed RNA polymerase subunit beta (rpoB) gene, 16S gene of a mycobacterium, a hemagglutinin (HA) gene of influenza virus, a matrix (M) gene of influenza A virus, a nonstructural (NS) gene of influenza B virus, and a Kirsten rat sarcoma viral oncogene (KRAS) gene.

11. The DDS probe system of claim 1, wherein the probe oligonucleotide and the antiprobe oligonucleotide consists of the nucleic acid sequences selected from the group consisting of: SEQ ID NOS: 1 and 2, SEQ ID NOS: 3 and 4, SEQ ID NOS: 7 and 8, SEQ ID NOS: 9 and 10, SEQ ID NOS: 13 and 14, SEQ ID NOS: 17 and 18, SEQ ID NOS: 19 and 20, SEQ ID NOS: 23 and 24, SEQ ID NOS: 36 and 37, SEQ ID NOS: 56 and 57, SEQ ID NOS: 64 and 65, SEQ ID NOS: 66 and 67, SEQ ID NOS: 70 and 71, SEQ ID NOS: 72 and 73, SEQ ID NOS: 79 and 80, SEQ ID NOS: 81 and 82, SEQ ID NOS: 85 and 86, SEQ ID NOS: 88 and 89, and SEQ ID NOS: 91 and 92.

12. A system for selectively amplifying and detecting a low frequency first target nucleotide sequence in a sample that is mixed with a high frequency second target nucleotide sequence, wherein the low frequency first target nucleotide sequence in the sample is in a range of 2 percent to 0.002 percent, wherein the low frequency first target nucleotide sequence and the high frequency second target nucleotide sequence are amplified with identical primers, said system for selectively amplifying and detecting a low frequency first target nucleotide sequence in a sample that is mixed with a high frequency second target nucleotide sequence comprising:

(a) the first probe:antiprobe detection system as defined in claim 1, wherein the probe oligonucleotide is complementary to the low frequency first target nucleotide sequence; and (b) an unlabeled terminator probe with an affinity for the high frequency second target nucleotide sequence that is higher than an affinity of the probe oligonucleotide for the low frequency first target nucleotide sequence and used to enhance amplification of the low frequency target nucleotide sequence by blocking or inhibiting amplification of the high frequency second target nucleotide sequence; wherein the unlabeled terminator probe comprises:

(i) an unlabeled oligonucleotide sequence complementary to the high frequency second target sequence, (ii) a 5' end modified to resist an exonuclease digestion, (iii) a 3' end modified to resist a polymerase extension reaction, (iv) a Tm that differs from the Tm of the probe oligonucleotide by at least 5° C., (v) a G that differs from the G of the probe oligonucleotide by at least 5 kcal/mol, and (vi) optionally, at least one of a non-natural nucleotide, a minor groove binder (MGB) and a Zip nucleic acid (ZNA).

13. The system of claim 12, further comprising a pair of flanking primers, PCR amplification reagents, an amplification product of a first subsystem, qPCR (quantitative PCR) amplification reagents, and a second probe:antiprobe system and dividing the system for selectively amplifying and detecting a low frequency first target nucleotide sequence in a sample that is mixed with a high frequency second target nucleotide sequence into two subsystems comprising:

(a) the first subsystem to selectively amplify templates comprising the low frequency first target sequence, comprising:
(i) the unlabeled terminator probe;
(ii) the pair of flanking primers; and
(iii) the PCR amplification reagents; and
(b) a second subsystem for reamplifying the amplification product of the first subsystem and for detecting the low frequency first target sequence, comprising:
(i) a dilute aliquot of the amplification product of the first subsystem;
(ii) the first probe:antiprobe detection system;
(iii) the pair of flanking primers;
(iv) the qPCR amplification reagents; and
(v) optionally, the second probe:antiprobe system.

14. The system of claim 12, wherein
the low frequency first target nucleotide sequence is a mutant sequence.

15. A method for selectively detecting a target nucleotide sequence of interest in a biological sample from a human, an animal or an organism, comprising the steps of:
obtaining the biological sample;
contacting the target nucleotide sequence of interest in the biological sample with the probe oligonucleotide and anti-probe oligonucleotide from the DDS probe system of claim 1 wherein the probe oligonucleotide is complementary to the target nucleotide sequence of interest; and detecting a fluorescent signal from a duplex formed by the target nucleotide sequence and the probe oligonucleotide, thereby selectively detecting the target nucleotide sequence of interest in the biological sample.

16. The method of claim 15, further comprising adding one or more primers to the biological sample and amplifying the target nucleotide sequence of interest.

* * * * *